United States Patent
Boyle et al.

(10) Patent No.: US 8,716,473 B2
(45) Date of Patent: May 6, 2014

(54) SUBSTITUTED BENZOTRIAZINES AND QUINOXALINES AS INHIBITORS OF P70S6 KINASE

(75) Inventors: Robert George Boyle, Cambridge (GB); David Winter Walker, Cambridge (GB)

(73) Assignee: Sentinel Oncology Limited (GB)

( * ) Notice: Subject to any disclaimer, the term of this patent is extended or adjusted under 35 U.S.C. 154(b) by 227 days.

(21) Appl. No.: 13/322,775

(22) PCT Filed: May 26, 2010

(86) PCT No.: PCT/GB2010/001036
§ 371 (c)(1),
(2), (4) Date: Nov. 28, 2011

(87) PCT Pub. No.: WO2010/136755
PCT Pub. Date: Dec. 2, 2010

(65) Prior Publication Data
US 2012/0071478 A1    Mar. 22, 2012

(30) Foreign Application Priority Data
May 26, 2009    (GB) .................................. 0908905.3

(51) Int. Cl.
C07D 401/14    (2006.01)
C07D 403/04    (2006.01)
C07D 403/14    (2006.01)
C07D 409/14    (2006.01)
A61K 31/53    (2006.01)
A61K 31/498    (2006.01)
A61P 35/00    (2006.01)

(52) U.S. Cl.
USPC ............ 544/183; 544/353; 514/243; 514/249

(58) Field of Classification Search
USPC ............................ 544/183, 353; 514/243, 249
See application file for complete search history.

(56) References Cited

U.S. PATENT DOCUMENTS
2003/0130285 A1    7/2003    Myers et al.

FOREIGN PATENT DOCUMENTS

| WO | 00/31050 | 6/2000 |
| WO | 2005096784 A1 | 10/2005 |
| WO | 2006131835 A2 | 12/2006 |
| WO | 2008141065 A1 | 11/2008 |
| WO | 2009021083 A1 | 2/2009 |

OTHER PUBLICATIONS

Yee D. J Natl Cancer Inst. 2012,104(13):975-81.*
Cecil Textbook of Medicine, edited by Bennet, J.C., and Plum F., 20th edition,vol. 1, 1004-1010, 1996.*
Mass, R. D., Int. J. Radiation ©ncology Bio. Phys.vol. 58(3): 932-940,201.*
Fabbro et al. Pharmacology & therapeutics 93, 79-98, 2002.*
Freshney et al.,Culture of Animal Cells, A Manual of Basic Technique, Alan R. Liss, Inc., 1983, New York, p4.*
Dermer et al., Bio/Technology, 1994, 12:320.*
Cohen et al., Current Opinion in Chemical Biology, 3,459-465, 1999.*
Golub et al., Science, 286, 531-537, 1999.*
International Search Report for PCT/GB2010/001036 dated Sep. 27, 2010.
United Kingdom Intellectual Property Office Search Report for GB 0908905.3 dated Jul. 17, 2009.
Gueto et al. Three-dimensional quantitative structure-activity relationship studies on novel series of benzotriazine based compounds acting as Src inhibitors using CoMFA and CoMSIA. Bioorganic & Medicinal Chemistry, 16, pp. 2439-2447 (2008).
Noronha et al. Discovery of [7-2,6-dichlorophenyl)-5-methylbenzo[1,2,4]triazin-3-ul]4-(2-pyrrolidin-1-ylethoxy)phenyl]-amine—a potent, orally active Src kinase inhibitor with anti-tumor activity in preclinical assays. Bioorganic & Medicinal Chemistry Letters, 17, pp. 602-608 (2007).

* cited by examiner

*Primary Examiner* — Venkataraman Balasubramanian
(74) *Attorney, Agent, or Firm* — Heslin Rothenberg Farley & Mesiti PC

(57) ABSTRACT

The invention provides compounds of the formula (1):

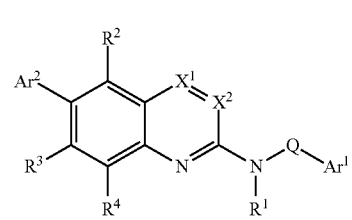

or salts or tautomers thereof; wherein $X^1$ is N or $N^+(O^-)$; $X^2$ is N or CH; Q is a $C_{1-3}$ alkylene group; $R^1$ is selected from hydrogen, $C_{1-4}$ hydrocarbyl and hydroxy-$C_{2-4}$ hydrocarbyl; $R^2$, $R^3$ and $R^4$ are the same or different and each is selected from hydrogen, fluorine, chlorine and methyl; $Ar^1$ is an optionally substituted monocyclic 5 or 6-membered aryl or heteroaryl ring containing 0, 1 or 2 heteroatom ring members selected from O, N and S, or a naphthyl ring and $Ar^2$ is an optionally substituted monocyclic 5 or 6-membered heteroaryl ring containing 1, 2 or 3 heteroatom ring members selected from O, N and S.
The compounds of formula (1) are inhibitors of p70S6 kinase and are useful in the treatment of proliferative diseases.

22 Claims, No Drawings

SUBSTITUTED BENZOTRIAZINES AND QUINOXALINES AS INHIBITORS OF P70S6 KINASE

CROSS REFERENCE TO RELATED APPLICATIONS

This application is a national stage filing under section 371 of International Application No. PCT/GB2010/001036 filed on May 26, 2010, and published in English on December 2, 2010 as WO 2010/136755 and claims priority of Great Britain Application No. 0908905.3 filed on May 26, 2009, the entire disclosure of these applications being hereby incorporated herein by reference.

This invention relates to compounds that inhibit or modulate the activity of p70S6 kinase, pharmaceutical compositions containing the compounds and the therapeutic uses of the compounds.

BACKGROUND OF THE INVENTION

The enzyme, p70S6 kinase (p70S6K) is a serine-threonine kinase and a member of the AGC family. It is a downstream effector of the phosphatidylinositol 3 kinase (PI3K)/AKT/ mammalian target of rapamycin (mTOR) signalling pathway and p70S6 undergoes phosphorylation and activation in response to growth factors such as IGF-I, EGF, TGF-[alpha] and HGF.

Activation of p70S6K in turn phosphorylates S6 ribosomal protein which promotes translation leading to an increase in protein synthesis in a cell. High levels of protein synthesis are required for cellular proliferation. It has also been shown that p70S6K has a necessary role in the mitotic cycle of a cell (Lane et al, Nature, 1993, 363(6425):170-2).

The kinase p70S6K has been shown to be constitutively activated in human tumour cells, leading to tumour cell proliferation. Inhibition of the p70S6K/mTOR pathway has been shown to lead to a decrease in tumour cell proliferation and an increase in tumour cell apoptosis (Pene et al (2002) Oncogene 21, 6587 and Le et al (2003) Oncogene 22, 484). Inhibition of p70S6K activity would therefore present an attractive approach for the treatment of cancer.

The mTOR/p70S6K pathway has been shown to be activated in renal cell carcinoma and is inhibited by CCI-779 (Robb, V. A.; Karbowniczek, M.; Klein-Szanto, A. J.; Henske, E. P. *J Urol* 2007, 177, 346-52). Furthermore, patients with gliobastoma multiforme whose tumours express high levels of phosphorylated p70S6K have been found to benefit from treatment with CCI-779 (Galanis, E.; Buckner, J. C.; Maurer, M. J.; Kreisberg, J. I.; Ballman, K.; Boni, J.; Peralba, J. M.; Jenkins, R. B.; Dakhil, S. R.; Morton, R. F.; Jaeckle, K. A.; Scheithauer, B. W.; Dancey, J.; Hidalgo, M.; Walsh, D. J. *J Clin Oncol* 2005, 23, 5294-304).

A significant linear association between disease progression and inhibition of p70S6K activity has been reported by Peralba et al [(2003) Clinical Cancer Research 9, 2887].

It would therefore be beneficial to develop compounds that have the ability to inhibit p70S6 kinase.

SUMMARY OF THE INVENTION

The present invention provides a class of novel arylalkylamino-substituted benzotriazines and quinoxalines as inhibitors of p70S6 kinase.

In one embodiment (Embodiment 1.1) of the invention, there is provided a compound of the formula (1):

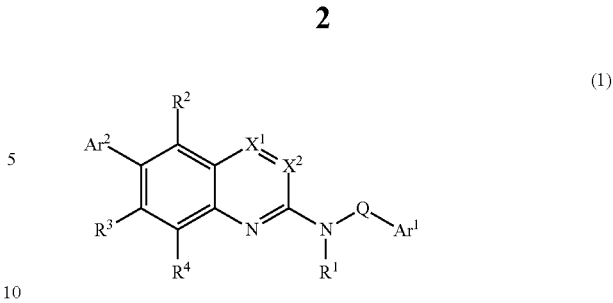

or a salt, solvate or tautomer thereof;
wherein:
$X^1$ is N or $N^+(O^-)$;
$X^2$ is N or CH;
Q is a $C_{1-3}$ alkylene group;
$R^1$ is selected from hydrogen, $C_{1-4}$ alkyl and hydroxy-$C_{2-4}$ alkyl;
$R^2$, $R^3$ and $R^4$ are the same or different and each is selected from hydrogen, fluorine, chlorine and methyl;
$Ar^1$ is a monocyclic 5 or 6-membered aryl or heteroaryl ring containing 0, 1 or 2 heteroatom ring members selected from O, N and S, or a naphthyl ring, the aryl or heteroaryl or naphthyl ring being optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; hydroxy; cyano; trifluoromethoxy; difluoromethoxy; amino; mono-$C_{1-4}$ hydrocarbylamino; di-$C_{1-4}$ hydrocarbylamino, $C_{1-4}$ hydrocarbyl-C(O)—; $C_{1-4}$ hydrocarbyl-C(O)-amino; $C_{1-4}$ hydrocarbylsulphonylamino; $C_{1-4}$ hydrocarbylureido; sulphamoyl; mono-$C_{1-4}$ hydrocarbylsulphamoyl; di-$C_{1-4}$ hydrocarbylsulphamoyl; carbamoyl; mono-$C_{1-4}$ hydrocarbyl carbamoyl; di-$C_{1-4}$ hydrocarbyl carbamoyl; a group O—$(CH_2)_k$—$OR^5$; and a group $O_m$—$(CH_2)_n$—$NR^6R^7$;
k is 2 to 4;
m is 0 or 1 and n is 0, 1, 2, 3 or 4 provided that when m is 1 then n is at least 2;
$R^5$ is hydrogen or $C_{1-4}$ hydrocarbyl;
$R^6$ is hydrogen or $C_{1-4}$ hydrocarbyl;
$R^7$ is hydrogen or $C_{1-4}$ hydrocarbyl;
or $NR^6R^7$ forms a saturated five or six membered heterocyclic ring optionally containing a further heteroatom selected from O, N and S or oxidised forms thereof, the heterocyclic ring being optionally substituted with 1 to 4 $C_{1-4}$ hydrocarbyl groups or hydroxy;
$Ar^2$ is a monocyclic 5 or 6-membered heteroaryl ring containing 1, 2 or 3 heteroatom ring members selected from O, N and S and being optionally substituted with 1, 2 or 3 substituents selected from fluorine; chlorine; bromine; $C_{1-4}$ hydrocarbyl; $C_{1-4}$ alkoxy; trifluoromethyl; difluoromethyl; hydroxy; cyano; trifluoromethoxy; difluoromethoxy; amino; mono-$C_{1-4}$ hydrocarbylamino; di-$C_{1-4}$ hydrocarbylamino; $C_{1-4}$ hydrocarbyl-C(O)—; $C_{1-4}$ hydrocarbyl-C(O)-amino; $C_{1-4}$ hydrocarbylsulphonylamino; $C_{1-4}$ hydrocarbylureido; sulphamoyl; mono-$C_{1-4}$ hydrocarbylsulphamoyl; di-$C_{1-4}$ hydrocarbylsulphamoyl; carbamoyl; mono-$C_{1-4}$ hydrocarbyl carbamoyl; and di-$C_{1-4}$ hydrocarbyl carbamoyl;
and wherein, in each substituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl and cyclopropylmethyl.

Particular and preferred compounds of the formula (1) are as defined in the following embodiments:
Embodiment 1a: A compound according to Embodiment 1.1 wherein:
$X^1$ is N or $N^+(O^-)$;

$X^2$ is N or CH;

Q is a $C_{1-3}$ alkylene group;

$R^1$ is selected from hydrogen, $C_{1-4}$ alkyl and hydroxy-$C_{2-4}$ alkyl;

$R^2$, $R^3$ and $R^4$ are the same or different and each is selected from hydrogen, fluorine, chlorine and methyl;

$Ar^1$ is a monocyclic 5 or 6-membered aryl or heteroaryl ring containing 0, 1 or 2 heteroatom ring members selected from O, N and S, or a naphthyl ring, the aryl or heteroaryl or naphthyl ring being optionally substituted with 1, 2 or 3 substituents selected from fluorine; chlorine; bromine; $C_{1-4}$ alkyl; $C_{2-4}$ alkenyl; $C_{2-4}$ alkynyl; $C_{1-4}$ alkoxy; trifluoromethyl; difluoromethyl; hydroxy; cyano; trifluoromethoxy; difluoromethoxy; amino; mono-$C_{1-4}$ alkylamino; di-$C_{1-4}$ alkylamino; $C_{1-4}$ alkanoyl; $C_{1-4}$ alkanoylamino; $C_{1-4}$ alkylsulphonylamino; $C_{1-4}$ alkylureido, sulphamoyl; mono-$C_{1-4}$ alkylsulphamoyl; di-$C_{1-4}$ alkylsulphamoyl; carbamoyl; mono-$C_{1-4}$ alkyl carbamoyl; di-$C_{1-4}$ alkyl carbamoyl; a group O—$(CH_2)_k$—$OR^5$; and a group $C_m$—$(CH_2)_n$—$NR^6R^7$;

k is 2 to 4;

m is 0 or 1 and n is 0, 1, 2, 3 or 4 provided that when m is 1 then n is at least 2;

$R^5$ is hydrogen or $C_{1-4}$ alkyl;

$R^6$ is hydrogen or $C_{1-4}$ alkyl;

$R^7$ is hydrogen or $C_{1-4}$ alkyl;

or $NR^6R^7$ forms a saturated five or six membered heterocyclic ring optionally containing a further heteroatom selected from O, N and S or oxidised forms thereof, the heterocyclic ring being optionally substituted with 1 to 4 $C_{1-4}$ alkyl groups or hydroxy;

$Ar^2$ is a monocyclic 5 or 6-membered heteroaryl ring containing 1, 2 or 3 heteroatom ring members selected from O, N and S and being optionally substituted with 1, 2 or 3 substituents selected from fluorine; chlorine; bromine; $C_{1-4}$ alkyl; $C_{2-4}$ alkenyl; $C_{2-4}$ alkynyl; $C_{1-4}$ alkoxy; trifluoromethyl; difluoromethyl; hydroxy; cyano; trifluoromethoxy; difluoromethoxy; amino; mono-$C_{1-4}$ alkylamino; di-$C_{1-4}$ alkylamino $C_{1-4}$ alkanoyl, $C_{1-4}$ alkanoylamino, $C_{1-4}$ alkylsulphonylamino, $C_{1-4}$ alkylureido, sulphamoyl; mono-$C_{1-4}$ alkylsulphamoyl; di-$C_{1-4}$ alkylsulphamoyl; carbamoyl; mono-$C_{1-4}$ alkyl carbamoyl; and di-$C_{1-4}$ alkyl carbamoyl.

Embodiment 1.1b: A compound according to Embodiment 1.1 wherein:

$X^1$ is N or $N^+(O^-)$;

$X^2$ is N or CH;

Q is a $C_{1-3}$ alkylene group;

$R^1$ is selected from hydrogen, $C_{1-4}$ alkyl and hydroxy-$C_{2-4}$ alkyl;

$R^2$, $R^3$ and $R^4$ are the same or different and each is selected from hydrogen, fluorine, chlorine and methyl;

$Ar^1$ is a monocyclic 5 or 6-membered aryl or heteroaryl ring containing 0, 1 or 2 heteroatom ring members selected from O, N and S and being optionally substituted with 1, 2 or 3 substituents selected from fluorine; chlorine; bromine; $C_{1-4}$ alkyl; $C_{1-4}$ alkoxy; trifluoromethyl; difluoromethyl; hydroxy; cyano; trifluoromethoxy; difluoromethoxy; amino; mono-$C_{1-4}$ alkylamino; di-$C_{1-4}$ alkylamino; $C_{1-4}$ alkanoyl; $C_{1-4}$ alkanoylamino; $C_{1-4}$ alkylsulphonylamino; $C_{1-4}$ alkylureido; sulphamoyl; mono-$C_{1-4}$ alkylsulphamoyl; di-$C_{1-4}$ alkylsulphamoyl; carbamoyl; mono-$C_{1-4}$ alkyl carbamoyl; and di-$C_{1-4}$ alkyl carbamoyl; and $Ar^2$ is a monocyclic 5 or 6-membered heteroaryl ring containing 1, 2 or 3 heteroatom ring members selected from O, N and S and being optionally substituted with 1, 2 or 3 substituents selected from fluorine; chlorine; bromine; $C_{1-4}$ alkyl; $C_{1-4}$ alkoxy; trifluoromethyl; difluoromethyl; hydroxy; cyano; trifluoromethoxy; difluoromethoxy; amino; mono-$C_{1-4}$ alkylamino; di-$C_{1-4}$ alkylamino; $C_{1-4}$ alkanoyl; $C_{1-4}$ alkanoylamino; $C_{1-4}$ alkylsulphonylamino; $C_{1-4}$ alkylureido; sulphamoyl; mono-$C_{1-4}$ alkylsulphamoyl; di-$C_{1-4}$ alkylsulphamoyl; carbamoyl; mono-$C_{1-4}$ alkyl carbamoyl; and di-$C_{1-4}$ alkyl carbamoyl.

Embodiment 1.2: A compound according to Embodiment 1.1 wherein Q is $C_{1-2}$ alkylene.

Embodiment 1.2a: A compound according to Embodiment 1.1 wherein Q is $CH_2$ or $CH(CH_3)$.

Embodiment 1.2b: A compound according to Embodiment 1.1 wherein Q is $CH_2$ or $CH_2CH_2$.

Embodiment 1.3: A compound according to Embodiment 1.2a wherein Q is $CH_2$.

Embodiment 1.3a: A compound according to Embodiment 1.2a wherein Q is $CH(CH_3)$.

Embodiment 1.3b: A compound according to Embodiment 1.3a wherein Q is in an R stereochemical configuration.

Embodiment 1.3c: A compound according to Embodiment 1.2b wherein Q is $CH_2CH_2$.

Embodiment 1.4: A compound according to any one of Embodiments 1.1 to 1.3c wherein $X^1$ is N.

Embodiment 1.5: A compound according to any one of Embodiments 1.1 to 1.3c wherein $X^1$ is $N^+(O^-)$.

Embodiment 1.6: A compound according to any one of Embodiments 1.1 to 1.5 wherein $X^2$ is N.

Embodiment 1.7: A compound according to any one of Embodiments 1.1 to 1.5 wherein $X^2$ is CH.

Embodiment 1.8: A compound according to any one of Embodiments 1.1 to 1.7 wherein $R^1$ is selected from hydrogen, methyl, ethyl, hydroxyethyl and hydroxypropyl.

Embodiment 1.9: A compound according to Embodiment 1.8 wherein $R^1$ is selected from hydrogen, methyl and hydroxyethyl.

Embodiment 1.9a: A compound according to Embodiment 1.9 wherein $R^1$ is selected from hydrogen and methyl.

Embodiment 1.10: A compound according to Embodiment 1.9 wherein $R^1$ is hydrogen.

Embodiment 1.10a: A compound according to Embodiment 1.9 wherein $R^1$ is methyl.

Embodiment 1.10b: A compound according to Embodiment 1.9 wherein $R^1$ is hydroxyethyl.

Embodiment 1.11: A compound according to any one of Embodiments 1.1 to 1.10b wherein $Ar^1$ is selected from phenyl, furyl, thienyl, pyridyl and naphthyl, each optionally substituted as defined in Embodiment 1.1.

Embodiment 1.11a: A compound according to any one of Embodiments 1.1 to 1.10b wherein $Ar^1$ is selected from phenyl, thienyl, pyridyl and naphthyl, each optionally substituted as defined in Embodiment 1.1.

Embodiment 1.11b: A compound according to any one of Embodiments 1.1 to 1.10b wherein $Ar^1$ is a monocyclic aryl or heteroaryl ring selected from phenyl, furyl, thienyl and pyridyl, each optionally substituted as defined in Embodiment 1.1.

Embodiment 1.12: A compound according to Embodiment 1.11 wherein $Ar^1$ is a phenyl ring optionally substituted as defined in Embodiment 1.1.

Embodiment 1.13: A compound according to any one of Embodiments 1.1 to 1.12 wherein $Ar^1$ is unsubstituted or is substituted with 1, 2 or 3 substituents selected from fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-3}$ alkylamino; di-$C_{1-3}$ alkylamino; $C_{1-3}$ alkanoyl; $C_{1-3}$ alkanoylamino; carbamoyl; mono-$C_{1-3}$ alkyl carbamoyl; di-$C_{1-3}$ alkyl carbamoyl; a group O—$(CH_2)_k$—$OR^5$; and a group $O_m$—$(CH_2)_n$—$NR^6R^7$; $R^5$ is hydrogen or $C_{1-3}$ alkyl;

$R^6$ is hydrogen or $C_{1-3}$ alkyl; $R^7$ is hydrogen or $C_{1-3}$ alkyl; or $NR^6R^7$ forms a saturated six membered heterocyclic ring containing a further heteroatom selected from O, N and S, the heterocyclic ring being optionally substituted with 1 to 4 $C_{1-3}$ alkyl groups or hydroxy; and k, m and n are as defined in Embodiment 1.1.

Embodiment 1.13a: A compound according to Embodiment 1.13 wherein $Ar^1$ is unsubstituted or is substituted with 1, 2 or 3 substituents selected from fluorine; chlorine; bromine; $O_{1-2}$ alkyl; $C_{1-2}$ alkoxy; trifluoromethyl; difluoromethyl; hydroxy; cyano; trifluoromethoxy; difluoromethoxy; amino; mono-$C_{1-2}$ alkylamino; di-$C_{1-2}$ alkylamino; acetyl; acetylamino; carbamoyl; mono-$C_{1-2}$ alkyl carbamoyl; di-$C_{1-2}$ alkyl carbamoyl; morpholinyl, piperazinyl, N-methylpiperazinyl and dimethylaminoethoxy.

Embodiment 1.13b: A compound according to any one of Embodiments 1.1 to 1.12 wherein $Ar^1$ is unsubstituted or substituted with 1, 2 or 3 substituents selected from fluorine, chlorine, bromine, methyl, hydroxy, methoxy, trifluoromethyl, difluoromethyl, cyano, trifluoromethoxy, difluoromethoxy, morpholinyl, piperazinyl, N-methylpiperazinyl and dimethylaminoethoxy.

Embodiment 1.13c: A compound according to any one of Embodiments 1.1 to 1.12 wherein $Ar^1$ is unsubstituted or substituted with 1, 2 or 3 substituents selected from fluorine, chlorine, methyl, hydroxy, methoxy, trifluoromethyl, difluoromethyl, trifluoromethoxy, morpholinyl, piperazinyl, N-methylpiperazinyl and dimethylaminoethoxy.

Embodiment 1.13d: A compound according to any one of Embodiments 1.1 to 1.12 wherein the optional substituents for $Ar^1$ are selected from fluorine, chlorine, bromine, methyl, methoxy, trifluoromethyl, difluoromethyl, cyano, trifluoromethoxy and difluoromethoxy.

Embodiment 1.13e: A compound according to any one of Embodiments 1.1 to 1.12 wherein the optional substituents for $Ar^1$ are selected from fluorine, chlorine, methyl, methoxy, trifluoromethyl and trifluoromethoxy.

Embodiment 1.13f: A compound according to any one of Embodiments 1.13 to 1.13e wherein $Ar^1$ is unsubstituted or substituted with one or two substituents.

Embodiment 1.13g: A compound according to any one of Embodiments 1.13 to 1.13f wherein $Ar^1$ is a phenyl ring which is substituted with one or two substituents wherein at least one substituent is present at the meta- or para-position of the phenyl ring.

Embodiment 1.13h: A compound according to any one of Embodiments 1.13 to 1.13g wherein $Ar^1$ is a phenyl ring which is substituted with one substituent which is present at the meta-position of the phenyl ring.

Embodiment 1.13i: A compound according to any one of Embodiments 1.13 to 1.13g wherein $Ar^1$ is a phenyl ring which is substituted with one substituent which is present at the para-position of the phenyl ring.

Embodiment 1.13j: A compound according to any one of Embodiments 1.13 to 1.13g wherein $Ar^1$ is a phenyl ring which is substituted with one substituent selected from 3-chloro, 4-chloro, 3-fluoro, 4-fluoro, 3-methoxy, 4-methoxy and 3-methyl.

Embodiment 1.14: A compound according to Embodiment 1.12 wherein the phenyl ring is unsubstituted or is mono-substituted and the substituent is chlorine.

Embodiment 1.15: A compound according to Embodiment 1.14 wherein the phenyl ring is monosubstituted with chlorine.

Embodiment 1.16: A compound according to Embodiment 1.15 wherein the chlorine atom is located at the meta- or para-position of the phenyl ring.

Embodiment 1.17: A compound according to Embodiment 1.16 wherein the chlorine atom is located at the para-position of the phenyl ring.

Embodiment 1.17a: A compound according to Embodiment 1.16 wherein the chlorine atom is located at the meta-position of the phenyl ring.

Embodiment 1.18: A compound according to any one of Embodiments 1.1 to 1.17a wherein $R^2$ is hydrogen.

Embodiment 1.19: A compound according to any one of Embodiments 1.1 to 1.18 wherein $R^3$ is hydrogen.

Embodiment 1.20: A compound according to any one of Embodiments 1.1 to 1.19 wherein $R^4$ is hydrogen.

Embodiment 1.21: A compound according to any one of Embodiments 1.1 to 1.20 wherein $Ar^2$ is selected from pyrazole, imidazole, oxazole, isoxazole, thiazole, isothiazole, furan, thiophene, pyridine, pyrimidine, pyrazine, pyridazine, triazole, thiadiazole, furazan and oxadiazole rings each optionally substituted as defined in Embodiment 1.1.

Embodiment 1.21a: A compound according to Embodiment 1.21 wherein $Ar^2$ is selected from pyrazole, pyridine and pyrimidine rings, each optionally substituted as defined in Embodiment 1.1.

Embodiment 1.22: A compound according to Embodiment 1.21 wherein $Ar^2$ is selected from pyrazole, imidazole, oxazole, isoxazole, thiazole, isothiazole and pyridine rings, each optionally substituted as defined in Embodiment 1.1.

Embodiment 1.23: A compound according to Embodiment 1.22 wherein $Ar^2$ is selected from pyrazole, imidazole and pyridine rings, each optionally substituted as defined in Embodiment 1.1.

Embodiment 1.24: A compound according to Embodiment 1.23 wherein $Ar^2$ is selected from pyrazole and pyridine rings, each optionally substituted as defined in Embodiment 1.1.

Embodiment 1.24a: A compound according to Embodiment 1.24 wherein $Ar^2$ is an optionally substituted pyrazole ring.

Embodiment 1.25: A compound as defined in any one of Embodiments 1.1 to 1.24a wherein $Ar^2$ is unsubstituted or is substituted with one or two substituents selected from methyl, amino, hydroxy and cyano.

Embodiment 1.25a: A compound as defined in Embodiment 1.25a wherein $Ar^2$ is unsubstituted or is mono-substituted.

Embodiment 1.25b: A compound as defined in Embodiment 1.25a wherein $Ar^2$ is unsubstituted or is mono-substituted with a substituent selected from methyl and amino.

Embodiment 1.25c: A compound as defined in Embodiment 1.25b wherein $Ar^2$ is unsubstituted or is mono-substituted with a methyl group.

Embodiment 1.25d: A compound as defined in Embodiment 1.25c wherein $Ar^2$ is unsubstituted.

Embodiment 1.26: A compound according to Embodiment 1.25 wherein $Ar^2$ is an unsubstituted pyrazole ring.

Embodiment 1.27: A compound according to Embodiment 1.1 which is selected from:

Benzyl-[6-(1H-pyrazol-4-yl)-quinoxalin-2-yl]-amine;
Benzyl-methyl-[6-(1H-pyrazol-4-yl)-quinoxalin-2-yl]-amine;
2-{Benzyl-[6-(1H-pyrazol-4-yl)quinoxalin-2-yl]-amino}-ethanol;
(4-Morpholin-4-yl-benzyl)-[6-(1H-pyrazol-4-yl)-quinoxalin-2-yl]-amine;
[4-(4-Methyl-piperazin-1-yl)benzyl]-[6-(1H-pyrazol-4-yl)-quinoxalin-2-yl]-amine;
[3-(4-Methyl-piperazin-1-yl)benzyl]-[6-(1H-pyrazol-4-yl)-quinoxalin-2-yl]-amine;

(3-Morpholin-4-yl-benzyl)-[6-(1H-pyrazol-4-yl)-quinoxalin-2-yl]-amine;
(4-Chloro-benzyl)-[6-(1H-pyrazol-4-yl)-quinoxalin-2-yl]-amine;
(3-Chloro-benzyl)-[6-(1H-pyrazol-4-yl)-quinoxalin-2-yl]-amine;
(2-Chloro-benzyl)-[6-(1H-pyrazol-4-yl)-quinoxalin-2-yl]-amine;
(4-Fluoro-benzyl)-[6-(1H-pyrazol-4-yl)-quinoxalin-2-yl]-amine;
(3-Fluoro-benzyl)-[6-(1H-pyrazol-4-yl)-quinoxalin-2-yl]-amine;
(2-Fluoro-benzyl)-[6-(1H-pyrazol-4-yl)-quinoxalin-2-yl]-amine;
[6-(1H-Pyrazol-4-yl)-quinoxalin-2-yl]-pyridin-4-ylmethyl-amine;
[6-(1H-Pyrazol-4-yl)-quinoxalin-2-yl]-pyridin-3-ylmethyl-amine;
[6-(1H-Pyrazol-4-yl)-quinoxalin-2-yl]-pyridin-2-ylmethyl-amine;
(4-Methoxy-benzyl)-[6-(1H-pyrazol-4-yl)-quinoxalin-2-yl]-amine;
(3-Methoxy-benzyl)-[6-(1H-pyrazol-4-yl)-quinoxalin-2-yl]-amine;
(2-Methoxy-benzyl)-[6-(1H-pyrazol-4-yl)-quinoxalin-2-yl]-amine;
(4-Fluoro-3-trifluoromethyl-benzyl)-[6-(1H-pyrazol-4-yl)-quinoxalin-2-yl]-amine;
(4-Fluoro-benzyl)-methyl-[6-(1H-pyrazol-4-yl)-quinoxalin-2-yl]-amine;
Benzyl-methyl-(6-pyridin-4-yl-quinoxalin-2-yl)-amine;
Benzyl-methyl-(6-pyrimidin-4-yl-quinoxalin-2-yl)-amine;
((S)-1-Phenyl-ethyl)-[6-(1H-pyrazol-4-yl)-quinoxalin-2-yl]-amine;
Phenethyl-[6-(1H-pyrazol-4-yl)-quinoxalin-2-yl]-amine;
Benzyl-ethyl-[6-(1H-pyrazol-4-yl)-quinoxalin-2-yl]-amine;
(3-Methoxy-benzyl)-methyl-[6-(1H-pyrazol-4-yl)-quinoxalin-2-yl]-amine;
(3-Fluoro-benzyl)-methyl-[6-(1H-pyrazol-4-yl)-quinoxalin-2-yl]-amine;
(4-Fluoro-3-trifluoromethyl-benzyl)methyl-[6-(1H-pyrazol-4-yl)-quinoxalin-2-yl]-amine;
[6-(1H-Pyrazol-4-yl)-quinoxalin-2-yl]-(3-trifluoromethoxy-benzyl)-amine;
[3-(2-Dimethylamino-ethoxy)-benzyl]-[6-(1H-pyrazol-4-yl)-quinoxalin-2-yl]-amine;
(3,4-Difluoro-benzyl)-[6-(1H-pyrazol-4-yl)-quinoxalin-2-yl]-amine;
((R)-1-Phenyl-ethyl)-[6-(1H-pyrazol-4-yl)-quinoxalin-2-yl]-amine;
Benzyl-methyl-[7-(1H-pyrazol-4-yl)-benzo[1,2,4]triazin-3-yl]-amine;
Benzyl-methyl-[1-oxy-7-(1H-pyrazol-4-yl)-benzo[1,2,4]triazin-3-yl]-amine;
(3-Methoxy-benzyl)-[1-oxy-7-(1H-pyrazol-4-yl)-benzo[1,2,4]triazin-3-yl]-amine;
(3-Methoxy-benzyl)-[7-(1H-pyrazol-4-yl)-benzo[1,2,4]triazin-3-yl]-amine;
[6-(1H-Pyrazol-4-yl)-quinoxalin-2-yl]-thiophen-3-ylmethyl-amine;
Naphthalen-2-ylmethyl-[6-(1H-pyrazol-4-yl)-quinoxalin-2-yl]-amine;
[6-(1H-Pyrazol-4-yl)-quinoxalin-2-yl]-(4-trifluoromethyl-benzyl)-amine;
(3-Methyl-benzyl)-[6-(1H-pyrazol-4-yl)-quinoxalin-2-yl]-amine;
(2-Methyl-benzyl)-[6-(1H-pyrazol-4-yl)-quinoxalin-2-yl]-amine;
Benzyl-methyl-(6-pyrimidin-5-yl-quinoxalin-2-yl)-amine;
(4-Methyl-benzyl)-[6-(1H-pyrazol-4-yl)-quinoxalin-2-yl]-amine;
(2-Chloro-benzyl)-methyl-[6-(1H-pyrazol-4-yl)-quinoxalin-2-yl]-amine;
Benzyl-[6-(5-methyl-1H-pyrazol-4-yl)-quinoxalin-2-yl]-amine;
{(R)-1-[3-(4-Methyl-piperazin-1-yl)-phenyl]-ethyl}-[6-(1H-pyrazol-4-yl)-quinoxalin-2-yl]-amine;
Methyl-[3-(4-methyl-piperazin-1-yl)-benzyl]-[6-(1H-pyrazol-4-yl)-quinoxalin-2-yl]-amine;
[(R)-1-(3-Fluoro-phenyl)-ethyl]-[6-(1H-pyrazol-4-yl)-quinoxalin-2-yl]-amine;
[(R)-1-(3-Methoxy-phenyl)-ethyl]-[6-(1H-pyrazol-4-yl)-quinoxalin-2-yl]-amine;
Methyl-((R)-1-phenyl-ethyl)-[6-(1H-pyrazol-4-yl)-quinoxalin-2-yl]-amine;
[(R)-1-(3-Fluoro-phenyl)-ethyl]-methyl-[6-(1H-pyrazol-4-yl)-quinoxalin-2-yl]-amine;
[(R)-1-(3-Methoxy-phenyl)-ethyl]-methyl-[6-(1H-pyrazol-4-yl)-quinoxalin-2-yl]-amine;
3-{[6-(1H-Pyrazol-4-yl)-quinoxalin-2-ylamino]-methyl}-phenol;
[(R)-1-(3-Chloro-phenyl)-ethyl]-[6-(1H-pyrazol-4-yl)-quinoxalin-2-yl]-amine;
[(R)-1-(3-Chloro-phenyl)-ethyl]-methyl-[6-(1H-pyrazol-4-yl)-quinoxalin-2-yl]-amine;
Methyl-((S)-1-phenyl-ethyl)-[6-(1H-pyrazol-4-yl)-quinoxalin-2-yl]-amine;
[6-(1H-Pyrazol-4-yl)-quinoxalin-2-yl]-((R)-1-m-tolyl-ethyl)-amine;
[(S)-1-(3-Fluoro-phenyl)-ethyl]-[6-(1H-pyrazol-4-yl)-quinoxalin-2-yl]-amine; and
[(S)-1-(3-Fluoro-phenyl)-ethyl]-methyl-[6-(1H-pyrazol-4-yl)-quinoxalin-2-yl]-amine;
and salts and tautomers thereof.

Embodiment 1.27a: A compound according to Embodiment 1.27 which is selected from
benzyl-[1-oxy-7-(1H-pyrazol-4-yl)-benzo[1,2,4]triazin-3-yl]-amine;
(4-chloro-benzyl)-[1-oxy-7-(1H-pyrazol-4-yl)-benzo[1,2,4]triazin-3-yl]-amine;
(3-chloro-benzyl)-[1-oxy-7-(1H-pyrazol-4-yl)-benzo[1,2,4]triazin-3-yl]-amine;
benzyl-[7-(1H-pyrazol-4-yl)-benzo[1,2,4]triazin-3-yl]-amine;
benzyl-[4-oxy-6-(1H-pyrazol-4-yl)-quinoxalin-2-yl]-amine;
benzyl-[6-(1H-pyrazol-4-yl)-quinoxalin-2-yl]-amine;
and salts, solvates and tautomers thereof.

Embodiment 1.27b: A compound according to Embodiment 1.27 which is selected from:
(3-Chloro-benzyl)-[6-(1H-pyrazol-4-yl)-quinoxalin-2-yl]-amine;
(4-Fluoro-benzyl)-[6-(1H-pyrazol-4-yl)-quinoxalin-2-yl]-amine;
(3-Fluoro-benzyl)-[6-(1H-pyrazol-4-yl)-quinoxalin-2-yl]-amine;
(4-Methoxy-benzyl)-[6-(1H-pyrazol-4-yl)-quinoxalin-2-yl]-amine;
(3-Methoxy-benzyl)-[6-(1H-pyrazol-4-yl)-quinoxalin-2-yl]-amine;
Phenethyl-[6-(1H-pyrazol-4-yl)-quinoxalin-2-yl]-amine;
(3-Fluoro-benzyl)-methyl-[6-(1H-pyrazol-4-yl)-quinoxalin-2-yl]-amine;

(3,4-Difluoro-benzyl)-[6-(1H-pyrazol-4-yl)-quinoxalin-2-yl]-amine;
((R)-1-Phenyl-ethyl)-[6-(1H-pyrazol-4-yl)-quinoxalin-2-yl]-amine;
[6-(1H-Pyrazol-4-yl)-quinoxalin-2-yl]-thiophen-3-ylmethyl-amine;
(3-Methyl-benzyl)-[6-(1H-pyrazol-4-yl)-quinoxalin-2-yl]-amine;
Benzyl-methyl-(6-pyrimidin-5-yl-quinoxalin-2-yl)-amine;
(4-Methyl-benzyl)-[6-(1H-pyrazol-4-yl)-quinoxalin-2-yl]-amine;
[(R)-1-(3-Methoxy-phenyl)-ethyl]-[6-(1H-pyrazol-4-yl)-quinoxalin-2-yl]-amine;
Methyl-((R)-1-phenyl-ethyl)-[6-(1H-pyrazol-4-yl)-quinoxalin-2-yl]-amine;
[(R)-1-(3-Methoxy-phenyl)-ethyl]-methyl-[6-(1H-pyrazol-4-yl)-quinoxalin-2-yl]-amine;
[(R)-1-(3-Chloro-phenyl)-ethyl]-[6-(1H-pyrazol-4-yl)-quinoxalin-2-yl]-amine;
[(R)-1-(3-Chloro-phenyl)-ethyl]-methyl-[6-(1H-pyrazol-4-yl)-quinoxalin-2-yl]-amine;
and salts and tautomers thereof.

Embodiment 1.28: A compound according to any one of Embodiments 1.1 to 1.27 which is in the form of a salt.

Embodiment 1.29: A compound according to Embodiment 1.28 wherein the salt is an acid addition salt.

Embodiment 1.30: A compound according to any one of Embodiments 1.1 to 1.29 which is in the form of a solvate.

Embodiment 1.31: A compound according to Embodiment 1.30 wherein the solvate is a hydrate.

Salts

The compounds of the invention as defined in Embodiments 1.1 to 1.31 may be presented in the form of salts.

The salts referred to above (and also defined in embodiment 1.28) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.29) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1, 5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci., Vol.* 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the invention may exist in a number of different geometric isomeric, and tautomeric forms and references to the compounds of formula (1) as defined in Embodiments 1.1 to 1.31 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.1 to 1.31 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (1) as defined in any one of Embodiments 1.1 to 1.31 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Prodrugs

The compounds of the formula (1) as defined in any one of Embodiments 1.1 to 1.31 may be presented in the form of a pro-drug.

By "prodrugs" is meant for example any compound that is converted in vivo into a biologically active compound of the formula (1), as defined in any one of Embodiments 1.1 to 1.31.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Complexes and Clathrates

Also encompassed by formula (1) or subgroups, subsets, preferences and examples thereof are complexes (e.g. inclusion complexes or clathrates with compounds such as cyclodextrins, or complexes with metals) of the compounds.

Biological Activity

Compounds of the formula (1) as defined in any one of Embodiments 1.1 to 1.31 have activity as inhibitors of p70S6 kinase. As such, they may be useful in preventing or treating disease states and conditions in which p70S6 kinase or mutant forms thereof play an active part.

For example, it is envisaged that the compounds of Embodiments 1.1 to 1.31 will be useful in treating a range of proliferative disorders such as cancers.

Accordingly, in further embodiments, the invention provides:

Embodiment 2.1: A compound of the formula (1) as defined in any one of Embodiments 1.1 to 1.31 for use in medicine or therapy.

Embodiment 2.2: A compound of the formula (1) as defined in any one of Embodiments 1.1 to 1.31 for use in preventing or treating disease states and conditions mediated by p70S6 kinase or mutant forms thereof.

Embodiment 2.3: A compound of the formula (1) as defined in any one of Embodiments 1.1 to 1.31 for use in preventing or treating disease states and conditions characterised by abnormal expression of p70S6 kinase (e.g. over-expression or expression of a mutant form of p70S6 kinase).

Embodiment 2.4: A compound of the formula (1) as defined in any one of Embodiments 1.1 to 1.31 for use as an anti-cancer agent.

Embodiment 2.5: The use of a compound of the formula (1) as defined in any one of Embodiments 1.1 to 1.31 for the manufacture of a medicament for the treatment of cancer.

Embodiment 2.6: A method of treating a cancer, which method comprises administering to a subject need thereof a therapeutically effective amount of a compound of the formula (1) as defined in any one of Embodiments 1.1 to 1.31, optionally together with another anti-cancer agent or radiation therapy.

Embodiment 2.7: A compound of the formula (1) as defined in any one of Embodiments 1.1 to 1.31 for use in enhancing a therapeutic effect of radiation therapy or chemotherapy in the treatment of a proliferative disease such as cancer.

Embodiment 2.8: The use of a compound of the formula (1) as defined in any one of Embodiments 1.1 to 1.31 for the manufacture of a medicament for enhancing a therapeutic effect of radiation therapy or chemotherapy in the treatment of a proliferative disease such as cancer.

Embodiment 2.9: A method for the prophylaxis or treatment of a proliferative disease such as cancer, which method comprises administering to a patient in combination with radiotherapy or chemotherapy a compound of the formula (1) as defined in any one of Embodiments 1.1 to 1.31.

Examples of proliferative disorders as defined in Embodiments 2.4 to 2.9 include, but are not limited to carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

One particular subset of cancers against which the compounds of Embodiments 1.1 to 1.31 should prove particularly active are cancers which are characterised by P70S6 overexpression or elevated expression of P70S6 or the presence of mutant forms of P70S6.

The ability of the compounds of the invention to inhibit P70S6 kinase can be determined by means of the protocols set out in the Examples section below.

Further particular examples of cancers against which the compounds of Embodiments 1.1 to 1.31 should prove particularly active are:

Breast Cancer (over expression is linked to poor prognosis and metastasis (see Mol. Can. Ther, 2010))

Diffuse large B-cell lymphoma: (see Expert Opin Ther Targets. 2009 September; 13(9):1085-93.)

Glioblastoma multiforme (associated with increased levels of P70S6K (see J Clin Oncol. 2005 Aug. 10; 23(23): 5294-304))

Human colorectal cancer (in which the mtor pathway & p70S6K are highly activated (see Ann. Surg. Oncol. 2009 September; 16(9):2617-28. Epub 2009 June 11))

Another subset of cancers against which the compounds of Embodiments 1.1 to 1.31 should prove particularly active includes:
glioblastoma multiforme;
adenocarcinomas of the colon;
non-small cell lung cancer;
small-cell lung cancer;
cisplatin-resistant small-cell lung cancer;
ovarian cancer;
leukemia;
pancreatic cancer;
prostate cancer;
mammary carcinoma;
renal cell carcinoma;
multiple myeloma;
Kaposi's sarcoma;
Hodgkin's lymphoma;
lymphangioeiomyomatosis; and
Nn-Hodgkin's lymphoma or sarcoma The ability of the compounds of Embodiments 1.1 to 1.31 to inhibit cell proliferation can also be determined using the protocols set out in the Examples section below.

One advantage of compounds of the formula (1) is that they are selective kinase inhibitors.

Preferred compounds of the formula (1) are those having an $IC_{50}$ against p70S6 kinase of less than 5 µM, or less than 1 µM and preferably less than 0.1 µM.

For example, compounds of the formula (1) are selective inhibitors of p70S6 kinase compared to activity against AKT (2) kinase. Preferred compounds of the formula (1) are at least 5 fold more active against p70S6 kinase than they are against AKT(2) kinase, and more preferred compounds of the formula (1) are at least 10 fold or at least 20 fold more active against p70S6 kinase than they are against AKT(2) kinase. Particularly preferred compounds are at least 100 fold more active against p70S6 kinase than they are against AKT(2) kinase.

Furthermore, compounds of the formula (1) are selective inhibitors of p70S6 kinase compared to activity against Aurora kinase. Preferred compounds of the formula (1) are at least 5 fold more active against p70S6 kinase than they are against Aurora A and/or B kinase, and more preferred compounds of the formula (1) are at least 10 fold more active against p70S6 kinase than they are against Aurora A and/or B kinase.

Compounds of formula (1) having greater selectivity for p70S6 kinase versus Aurora A and/or Aurora B kinase and/or Akt kinase are expected to exhibit improved side effect profiles in relation to side effects arising from Aurora kinase and Akt kinase inhibition.

Accordingly, in further embodiments, the invention provides:

Embodiment 2.10: A compound according to any one of Embodiments 1.1 to 1.31 having an $IC_{50}$ against p70S6 kinase of less than 5 µM.

Embodiment 2.11: A compound according to any one of Embodiments 1.1 to 1.31 having an $IC_{50}$ against p70S6 kinase of or less than 1 µM.

Embodiment 2.12: A compound according to any one of Embodiments 1.1 to 1.31 having an an $IC_{50}$ against p70S6 kinase of less than 0.1 µM.

Embodiment 2.13: A compound according to any one of Embodiments 2.10 to 2.12 for use in a therapy, treatment, method or use according to any one of Embodiments 2.1 to 2.9.

Methods for the Preparation of Compounds of the Invention

The invention also provides methods for the preparation of a compound of the formula (1).

Accordingly, in another embodiment (Embodiment 3.1), the invention provides a method for preparing a compound as defined in any one of Embodiments 1.1 to 1.31, which method comprises:

(a) the reaction of a compound of the formula (10):

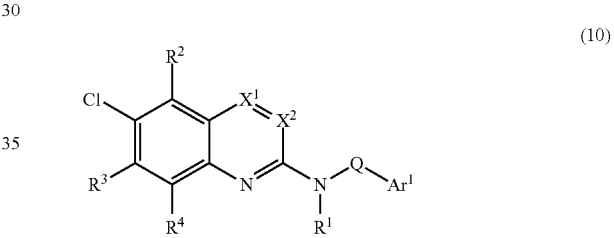

or an N-oxide thereof, with a boronic acid or boronate reagent of the formula $Ar^2$-Bor where Bor is a boronate or boronic acid residue, in the presence of a palladium catalyst; or (b) the reaction of a compound of the formula (II):

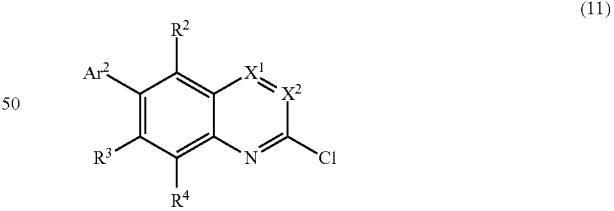

or a protected form thereof, with a compound of the formula $Ar^1$-Q-$NR^2$H.

Reaction (a) above may be carried out under Suzuki coupling conditions, in the presence of a palladium catalyst such as bis(tri-t-butylphosphine)palladium (0) and a base (e.g. a carbonate such as potassium carbonate). The reaction may be carried out in a polar solvent such as dimethyl formamide (DMF), and the reaction mixture is typically subjected to heating, for example to a temperature in excess of 100° C.

Reaction (b) above may be carried out at room temperature in a polar solvent such as dimethyl sulphoxide or dimethyl formamide.

Illustrative reaction schemes for the preparation of compounds of the formula (1) are set out below.

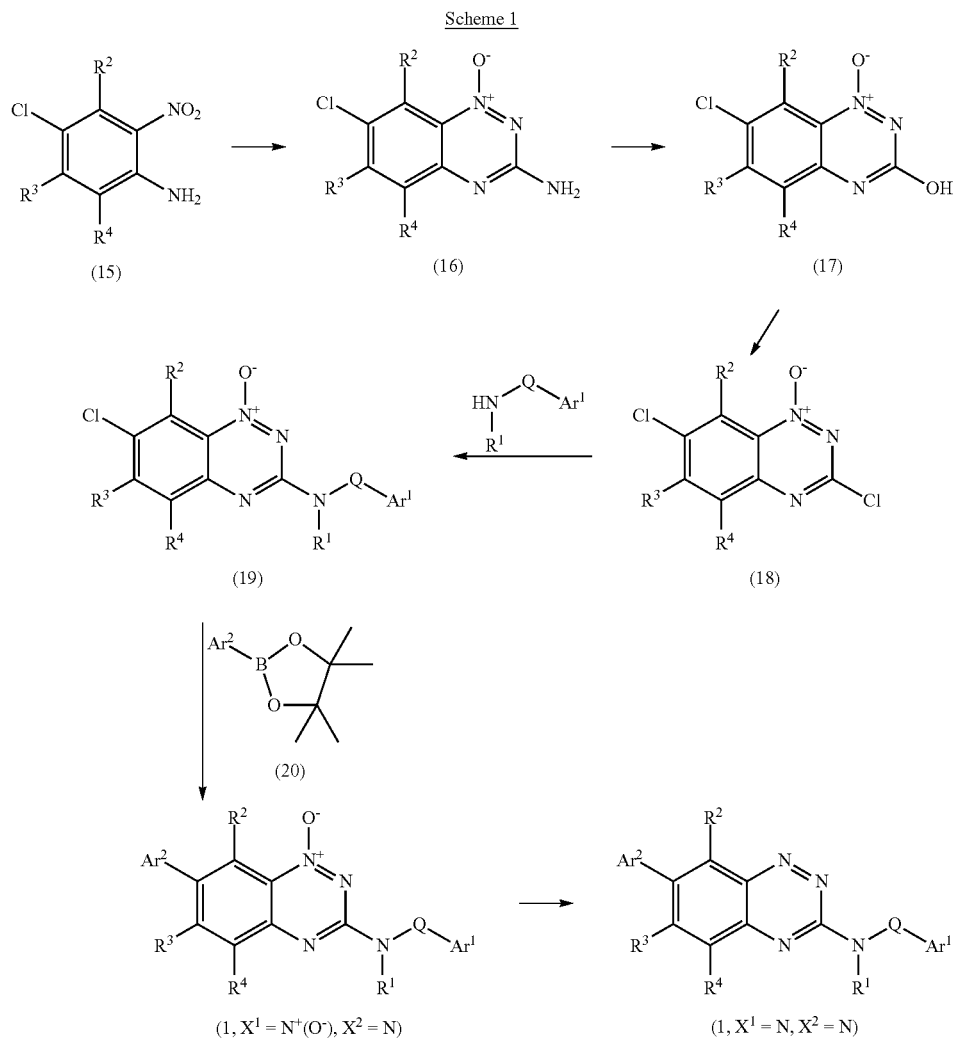

Scheme 1

Scheme 1 may be used to prepare benzotriazine compounds of the formula (1) in which X is N and N-oxides thereof.

In Scheme 1, the starting material is the chloronitroaniline (15) which is commercially available or can be prepared by methods well known to the skilled chemist.

The chloronitroaniline (15) is reacted wth cyanamide with heating (e.g. to a temperature of up to about 100° C.) to give the amino-benzotriazine N-oxide (16).

The amino-benzotriazine N-oxide (16) is diazotized with $NaNO_2$/HCl and the intermediate diazonium salt (not shown) is hydrolysed to form the hydroxybenzotriazine N-oxide compound (17). Reaction of the hydroxybenzotriazine N-oxide compound (17) with phosphorus oxychloride in the presence of a non-interfering base such as N,N-dimethylaniline gives the chlorobenzotriazine N-oxide compound (18). The chlorination reaction is typically carried out with heating, for example at reflux temperatures.

The chlorine atom at the 3-position of the benzotriazine ring is then displaced by a group $Ar^1$-Q-$NR^2$ by reaction with an amine compound of the formula $Ar^1$-Q-$NR^2$H to give the compound of formula (19). The displacement reaction may be carried out in a polar solvent such as DMF or DMSO, typically at room temperature.

The compound of formula (19) may then be reacted with a boronate or boronic acid derivative of the formula $Ar^2$-Bor where Bor is a boronate or boronic acid residue under Suzuki coupling conditions. In Scheme 1, $Ar^2$-Bor is exemplified by the boronic acid pinacol ester (20). The reaction is typically carried out with heating (e.g. to a temperature in the range 60-100° C.), in a polar solvent such as DMF in the presence of a palladium catalyst such as Fu's catalyst (bis(tri-t-butylphosphine)palladium (0)) and a base such as potassium carbonate or caesium carbonate.

Boronates and boronic acids of the formula $Ar^2$-Bor are widely available commercially or can be prepared for example as described in the review article by N. Miyaura and A. Suzuki, Chem. Rev. 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

The Suzuki coupling reaction gives rise to an N-oxide compound corresponding to formula (1) wherein $X^1$ is $N^+(O^-)$ and $X^2$ is N. The N-oxide may be reduced to the corresponding non N-oxide corresponding to formula (1) wherein $X^1$ is N and $X^2$ is N using a reducing agent such as sodium dithionite ($Na_2S_2O_4$). The reduction may be carried out in an aqueous solvent such as aqueous ethanol, usually with heating, for example at reflux.

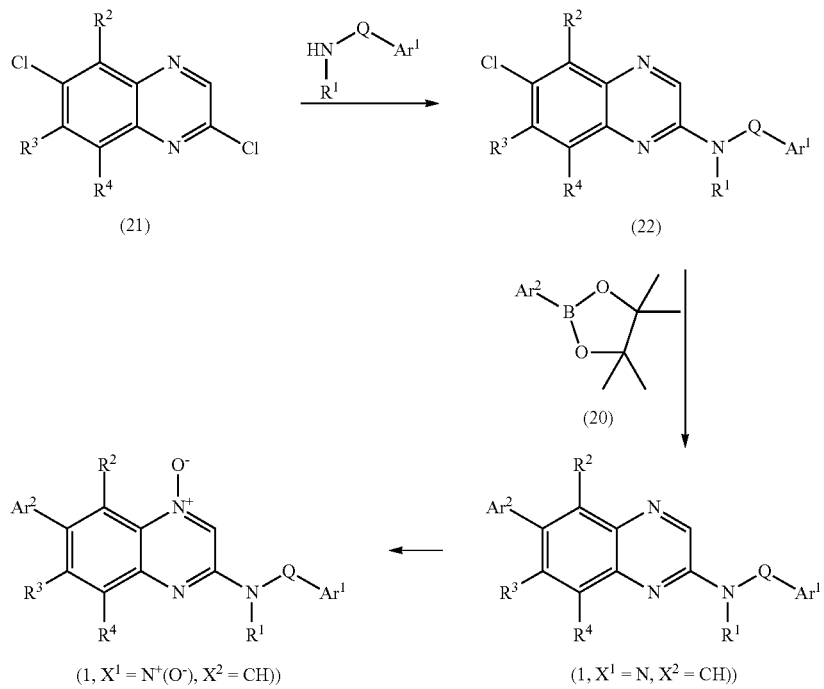

Scheme 2

Compounds of the formula (1), and their N-oxides, may be prepared by the sequence of reactions shown in Scheme 2 above.

The starting material for Scheme 2 is the 2,6-dichoroquinoxaline (21) which is commercially available (when $R^2$, $R^3$ and $R^4$ are all hydrogen) or can be made by methods well known to the skilled chemist or methods analogous thereto.

The first step in the reaction sequence comprises the displacement of the 2-chlorine atom of the 2,6-dichoroquinoxaline (21) by $Ar^1$-Q-$NR^2$ by reaction with an amine compound of the formula $Ar^1$-Q-$NR^2$H to give the 6-chloroquinoxaline (22). The displacement reaction may be carried out in a polar solvent such as DMF or DMSO, typically at room temperature.

The 6-chloroquinoxaline (22) is then subjected to a Suzuki coupling reaction with a boronate or boronic acid derivative of the formula $Ar^2$-Bor under the conditions described above for Scheme 1, to give a compound of the formula (1) wherein $X^1$ is N and $X^2$ is CH. In Scheme 2, $Ar^2$-Bor is exemplified by the boronic acid pinacol ester (20).

The compound of formula (1) can then, if desired, be oxidised to the N-oxide by reaction with an oxidising agent such as hydrogen peroxide (for example $H_2O_2$ in acetic acid) to give the corresponding N-oxide of formula (1) wherein $X^1$ is $N^+O^-$ and $X^2$ is CH.

Further examples of synthetic routes to the compounds of formula (1) are described in the Examples section below.

Once formed, one compound of the formula (1) or a protected derivative thereof, can be converted into another compound of the formula (1) by methods well known to the skilled person. Examples of synthetic procedures for converting one functional group into another functional group are set out in standard texts such as *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.31 together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound of formula (1), as defined in any one of Embodiments 1.1 to 1.31, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formula (1) and sub-groups as defined herein will be useful either as sole chemotherapeutic agents or, more usually, in combination therapy with chemotherapeutic agents or radiation therapy in the prophylaxis or treatment of a range of proliferative disease states or conditions. Examples of such disease states and conditions are set out above.

Particular examples of chemotherapeutic agents that may be co-administered with the compounds of formula (1) include:
  Topoisomerase I inhibitors
  Antimetabolites
  Tubulin targeting agents
  DNA binder and topoisomerase II inhibitors
  EGFR inhibitors and other PI3K pathway inhibitors
  Alkylating Agents (e.g. temozolomide)
  Monoclonal Antibodies.
  Anti-Hormones
  Signal Transduction Inhibitors
  Proteasome Inhibitors DNA methyl transferases
Cytokines and retinoids
Hypoxia triggered DNA damaging agents (e.g. Tirapazamine)

Further examples of chemotherapeutic agents that may be co-administered with the compounds of formula (1) include:
Torc 1 inhibitors
Aromatase inhibitors
Anti Her2 antibodies, (see for example http://www.wipo.int/pctdb/en/wo.jsp?wo=2007056118), lapatinib
Anti cd20 antibodies
Inhibitors of angiogenesis
HDAC inhibitors
mTOR inhibitors & EGFR
other PI3K pathway inhibitors (e.g. PI3K, PDK1)
MEK inhibitors
EGFR (e.g. Everolimus & Genfitinib—see Biochemical Pharmacology 78 2009 460-468)

One particular combination comprises a compound according to any one of Embodiments 1.1 to 1.31 together with an EGFR inhibitor such as Everolimus & Genfitinib.

The compounds may also be administered in conjunction with radiotherapy.

The compounds may be administered over a prolonged term to maintain beneficial therapeutic effects or may be administered for a short period only. Alternatively they may be administered in a pulsatile or continuous manner.

The compounds of the invention will be administered in an effective amount, i.e. an amount which is effective to bring about the desired therapeutic effect. For example, the "effective amount" can be a quantity of compound which, when administered to a subject suffering from cancer, slows tumour growth, ameliorates the symptoms of the disease and/or increases longevity.

The amount of P70S6 inhibitor compound of the invention administered to the subject will depend on the type and severity of the disease or condition and on the characteristics of the subject, such as general health, age, sex, body weight and tolerance to drugs. The skilled person will be able to determine appropriate dosages depending on these and other factors.

The compounds are generally administered to a subject in need of such administration, for example a human or animal patient, preferably a human.

A typical daily dose of the compound of formula (1) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

Methods of Diagnosis

Prior to administration of a compound of the formula (1), a patient may be screened to determine whether a disease or condition from which the patient is or may be suffering is one which would be susceptible to treatment with a compound having activity against p70S6 kinase.

For example, a biological sample taken from a patient may be analysed to determine whether a condition or disease, such as cancer, that the patient is or may be suffering from is one which is characterised by a genetic abnormality or abnormal protein expression which leads to up-regulation of p70S6 kinase or to sensitisation of a pathway to normal p70S6 kinase activity or to over-expression of phosphorylated p70S6 kinase. The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of p70S6 kinase. The term diagnosis includes screening. By marker we include genetic markers including, for example, the measurement of DNA composition to identify mutations of p70S6. The term marker also includes markers which are characteristic of up-regulation of p70S6, including enzyme activity, enzyme levels, enzyme state (e.g. phosphorylated or not) and mRNA levels of the aforementioned proteins.

Tumours with upregulation of p70S6 kinase may be particularly sensitive to p70S6 inhibitors. Tumours may preferentially be screened for upregulation of p70S6. Thus, the patient may be subjected to a diagnostic test to detect a marker characteristic of up-regulation of p70S6. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of up-regulation of p70S6 kinase could be applicable in the present case.

Accordingly, in another embodiment of the invention (Embodiment 5.1), there is provided a method for the diagnosis and treatment of a disease state or condition mediated by p70S6 kinase which method comprises (i) screening a patient to determine whether a disease or condition from which the patient is or may be suffering is one which would be susceptible to treatment with a compound having activity against p70S6 kinase; and (ii) where it is indicated that the disease or condition from which the patient is thus susceptible, thereafter administering to the patient a compound as defined in any one of Embodiments 1.1 to 1.31.

In another embodiment (Embodiment 5.2), there is provided the use of a compound as defined in any one of Embodiments 1.1 to 1.31 for the manufacture of a medicament for the treatment or prophylaxis of a disease state or condition in a patient who has been screened and has been determined as suffering from, or being at risk of suffering from, a disease or condition which would be susceptible to treatment with a compound having activity against p70S6.

In a further embodiment (Embodiment 5.3), there is provided a compound as defined in any one of Embodiments 1.1 to 1.31 for use in the treatment or prophylaxis of a disease state or condition in a patient who has been screened and has been determined as suffering from, or being at risk of suffering from, a disease or condition which would be susceptible to treatment with a compound having activity against p70S6.

In another embodiment of the invention (Embodiment 5.4), there is provided a method for the diagnosis and treatment of a disease state or condition characterised by up-regulation of p70S6 kinase or the presence of a mutated form of p70S6, which method comprises (i) screening a patient to determine whether a disease or condition from which the patient is or may be suffering is one which would be susceptible to treatment with a compound having activity against p70S6 kinase; and (ii) where it is indicated that the disease or condition from which the patient is thus susceptible, thereafter administering to the patient a compound as defined in any one of Embodiments 1.1 to 1.31.

EXAMPLES

In the following examples, all NMR experiments were run in d6-DMSO
LCMS Conditions
The following methods were used to analyse the compounds of Examples 1-60 below.
Method A
LC-MS was carried out using X-bridge $C_{18}$ 150×4.6 mm, 5 micron. Column flow rate was 1 mL/min and solvents used were 100% in HPLC grade water (A) and 100% ACN Gradient grade (B), with an injection volume of 10 µL. The method is as described below.

| Time (min) | A  | B   |
|------------|----|-----|
| 0.01       | 90 | 10  |
| 5.00       | 10 | 90  |
| 6.00       | 0  | 100 |
| 10.00      | 0  | 100 |
| 10.01      | 90 | 10  |
| 12.00      | 90 | 10  |

Method B
LC-MS was carried out using X-bridge $C_{18}$ 250×4.6 mm, 5 micron. Column flow rate was 1 mL/min and solvents used were 100% in HPLC grade water (A) and 100% ACN Gradient grade (B), with an injection volume of 10 µL. The method is as described below.

| Time (min) | A  | B   |
|------------|----|-----|
| 0.01       | 90 | 10  |
| 9.00       | 10 | 90  |
| 11.00      | 0  | 100 |
| 20.00      | 0  | 100 |
| 20.01      | 90 | 10  |
| 25.00      | 90 | 10  |

Method C
LC-MS was carried out using X-Bridge $C_{18}$ 250×4.6 mm, 5 micron. Column flow was 1 mL/min and solvents used were 0.05% $CH_3COONH_4$ in water HPLC grade (A) and 0.05% $CH_3COONH_4$ in methanol gradient grade (B) with an injection volume of 5 µL. The method is as described below.

| Time (min) | A  | B   |
|------------|----|-----|
| 0.01       | 90 | 10  |
| 6.00       | 10 | 90  |
| 8.00       | 0  | 100 |
| 12.00      | 0  | 100 |

-continued

| Time (min) | A | B |
|---|---|---|
| 12.01 | 90 | 10 |
| 14.00 | 90 | 10 |

Method D

LC-MS was carried out using X-bridge $C_{18}$ 150×4.6 mm, 5 micron at 265 nm. Column flow rate was 1 mL/min and solvents used were 100% in HPLC grade water (A) and 100% ACN Gradient grade (B), with an injection volume of 10 μL. The method is as described below.

| Time (min) | A | B |
|---|---|---|
| 0.01 | 90 | 10 |
| 6.00 | 10 | 90 |
| 8.00 | 0 | 100 |
| 12.00 | 0 | 100 |
| 12.01 | 90 | 10 |
| 14.00 | 90 | 10 |

Method E

LC-MS was carried out using X-bridge $C_{18}$ 150×4.6 mm, 5 micron. Column flow rate was 1 mL/min and solvents used were 0.05% CH3COONH4 in water:methanol, with an injection volume of 10 μL. The method is as described below.

| Time (min) | A | B |
|---|---|---|
| 0.01 | 90 | 10 |
| 5.00 | 10 | 90 |
| 6.00 | 0 | 100 |
| 10.00 | 0 | 100 |
| 10.01 | 90 | 10 |
| 12.00 | 90 | 10 |

Method F

LC-MS was carried out using X-bridge $C_{18}$ 150×4.6 mm, 5 micron. Column flow rate was 1 mL/min and solvents used were 0.1% TFA in water:ACN, with an injection volume of 10 μL. The method is as described below.

| Time (min) | A | B |
|---|---|---|
| 0.01 | 90 | 10 |
| 5.00 | 10 | 90 |
| 7.00 | 0 | 100 |
| 10.00 | 0 | 100 |
| 10.01 | 90 | 10 |
| 12.00 | 90 | 10 |

Method G

LC-MS was carried out using X-bridge $C_{18}$ 150×4.6 mm, 5 micron. Column flow rate was 1 mL/min and solvents used were 0.1% Formic acid in water:ACN, with an injection volume of 10 μL. The method is as described below.

| Time (min) | A | B |
|---|---|---|
| 0.01 | 90 | 10 |
| 5.00 | 10 | 90 |

-continued

| Time (min) | A | B |
|---|---|---|
| 6.00 | 0 | 100 |
| 10.00 | 0 | 100 |
| 10.01 | 90 | 10 |
| 12.00 | 90 | 10 |

Method H

LC-MS was carried out using X-bridge $C_{18}$ 150×4.6 mm, 5 micron. Column flow rate was 1 mL/min and solvents used were 0.05% CH3COONH4 in water:methanol, with an injection volume of 10 μL. The method is as described below.

| Time (min) | A | B |
|---|---|---|
| 0.01 | 90 | 10 |
| 5.00 | 10 | 90 |
| 7.00 | 0 | 100 |
| 10.00 | 0 | 100 |
| 10.01 | 90 | 10 |
| 12.00 | 90 | 10 |

The following method was used to analyse the compounds of Examples 61-65 below.

Samples were analysed by reverse phase HPLC-MS using a Waters 2795 Alliance HT HPLC, a Micromass ZQ mass spectrometer and a Waters 996 photodiode array UV detector. The LC-MS used electrospray ionisation and can choose between two different chromatography systems.

Solvents

C=1.58 g ammonium formate in 2.5 L water+2.5 mL Ammonia solution

D=2.5 L Acetonitrile+132 mL (5%) solvent C+2.5 mL Ammonia solution

Chromatography

Column: Phenomenex Gemini C18, 5 um, 4.6×30 mm

Injection Volume: 5 μL

UV detection: 220 to 400 nm

Column Temperature: 35° C.

| Time | A % | B % | C % | D % | Flow (mL/min) |
|---|---|---|---|---|---|
| 0.00 | 0.0 | 0.0 | 95.0 | 5.0 | 2.000 |
| 4.25 | 0.0 | 0.0 | 5.0 | 95.0 | 2.000 |
| 5.80 | 0.0 | 0.0 | 5.0 | 95.0 | 2.000 |
| 5.90 | 0.0 | 0.0 | 95.0 | 5.0 | 2.000 |
| 7.00 | 0.0 | 0.0 | 95.0 | 5.0 | 2.000 |

Mass Spectrometer

| Ionization mode | Positive | Negative |
|---|---|---|
| Capillary Voltage | 3.20 kV | −3.00 kV |
| Cone Voltage | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| InterScan delay: | 0.20 seconds | 0.20 seconds |
| Mass range: | 80 to 1000 AMU | 80 to 1000 AMU |

Abbreviations

The following abbreviations are used in the Examples below:

DMF dimethylformamide
MeOH methanol
DCM dichloromethane
DMSO dimethylsulphoxide
NEt₃ triethylamine
EtOAc ethyl acetate
n-BuOH n-butanol
Boc tert-butoxycarbonyl Example 1

Benzyl-[6-(1H-pyrazol-4-yl)-quinoxalin-2-yl]-amine

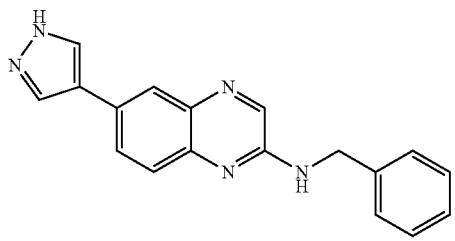 [SMILES: c1ccc(CNc2cnc3cc(-c4cn[nH]c4)ccc3n2)cc1]

The title compound was prepared by the synthetic route shown in Scheme A below.

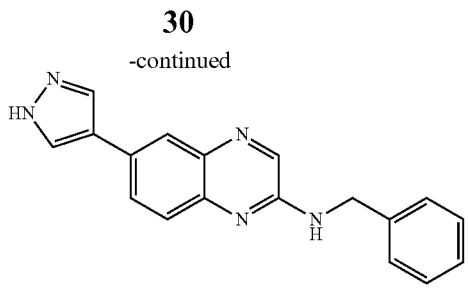

4

Step A

Benzyl-(6-chloro-quinoxalin-2-yl)-amine 2,6-Dichloroquinoxaline (0.500 g, 2.5 mmol) was dissolved in DMSO (10 mL) at RT and phenylmethanamine (1.3 g, 12.56 mmol) was added. The reaction mixture was stirred at RT for 16 h. After completion of reaction (confirmed by TLC), water (100 mL) was added to the reaction mixture and this layer was extracted with ethyl acetate (50 mL×3). The organic layer was washed with water (15 mL), brine (15 mL) and dried over Na₂SO₄. The organic layer was concentrated under vacuum to give crude product.

The crude product was adsorbed onto silica gel and purified by column chromatography using neutral silica gel of 60-120 mesh size. A gradient of 5 to 15% ethyl acetate in hexane was used to elute the title compound (0.490 g, 72%).

Step B 4-(2-Benzylamino-quinoxalin-6-yl)-pyrazole-1-carboxylic acid tert-butyl ester A mixture of benzyl-(6-chloro-quinoxalin-2-yl)-amine (0.250 g, 0.92 mmol, 1 eq), N-Boc-4-pyrazole boronic acid pinacol ester (0.328 g, 1.1 mmol, 1.2 eq), caesium carbonate (1.2 g, 3.71 mmol, 4.03 eq), potassium iodide (0.015 g, 0.09 mmol, 0.1 eq) in 1,4-dioxane (12 mL) was degassed at RT under vacuum and placed under an atmosphere of nitrogen. The process was repeated twice and Fu's catalyst (bis(tri-tert-butylphosphine)-palladium(0)) (0.023 g, 0.046 mmol) was added at RT. The reaction mixture was heated to 100° C. by microwave irradiation for 180 min. The organic mixture was diluted with ethyl acetate (150) and washed with water (20 mL×2) and brine (20 mL). The organic solvent was evaporated under vacuum to give crude product.

The crude product was purified by column chromatography using neutral silica gel of 60-120 mesh size. A gradient of 25-35% ethyl acetate in hexane was used to elute the title compound (157 mg, 43%).

Step C

Benzyl-[6-(1H-pyrazol-4-yl)-quinoxalin-2-yl]-amine

To the ice cold solution of 4-(2-benzylamino-quinoxalin-6-yl)-pyrazole-1-carboxylic acid tert-butyl ester (157 mg, 0.39 mmol) in 1,4-dioxane (3 mL) was added 14% HCl in dioxane (2 mL). The resulting mixture was stirred at RT for 2 hrs. After completion of reaction the volatiles were evaporated off under vacuum and the HCl salt was triturated with DCM to obtain crude product. The crude was further purified by prep-HPLC to afford the title compound (32 mg, 27%).

Example 2

Benzyl-methyl-[6-(1H-pyrazol-4-yl)-quinoxalin-2-yl]-amine hydrochloride

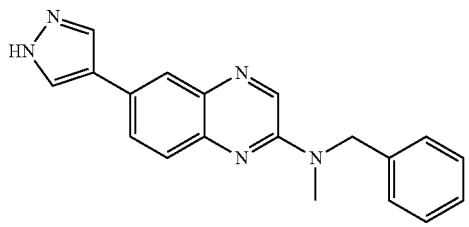 [SMILES: CN(Cc1ccccc1)c1cnc2cc(-c3cn[nH]c3)ccc2n1]

The title compound was prepared by the sequence of reactions shown in Scheme B below.

Scheme B

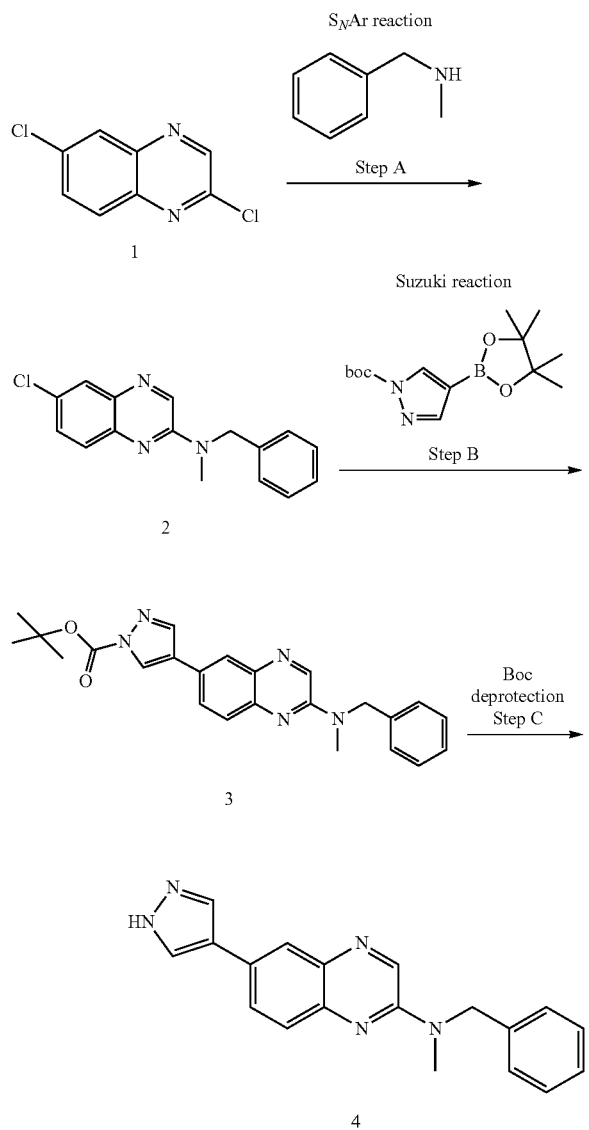

Step A

Benzyl-(6-chloro-quinoxalin-2-yl)-methyl-amine 2,6-Dichloroquinoxaline (0.500 g, 2.5 mmol) was dissolved in DMSO (10 mL) at RT and N-methyl-1-phenyl-methanamine (1.53 g, 12.56 mmol) was added to the reaction mixture. The reaction mixture was stirred at RT for 16 hrs. After completion of reaction (checked by TLC), water (100 mL) was added to the reaction mixture and it was extracted with ethyl acetate (50 mL×3). The organic layer was washed with water (10 mL), brine (10 mL) and dried over $Na_2SO_4$. The organic layer was concentrated under vacuum to give the crude product.

The crude product was purified by column chromatography using neutral silica gel of 60-120 mesh size. A gradient of 5-15% ethyl acetate in hexane was used for elution of the title compound (0.550 g, 93%).

Step B

4-[2-(Benzyl-methyl-amino)-quinoxalin-6-yl]-pyrazole-1-carboxylic acid tert-butyl ester N-benzyl-6-chloro-N-methylquinoxalin-2-amine (0.250 g, 0.88 mmol), N-Boc-4-pyrazole boronic acid pinacol ester (0.310 g, 1.05 mmol), caesium carbonate (1.14 g, 3.52 mmol), potassium iodide (0.014 g, 0.088 mmol) were added to 1,4-dioxane (12 mL) at RT. The mixture was degassed under vacuum and was placed under an atmosphere of nitrogen (the process was repeated twice). Fu's catalyst (Bis(tri-tert-butylphosphine) palladium(0)) (0.022 g, 0.04 mmol) was added at RT. The reaction mixture was heated at 100° C. by irradiation for 180 min in a microwave reactor. The organic mixture was diluted with ethyl acetate (150 mL) and washed with water (20 mL×3) followed by brine (20 mL). The organic solvent was distilled under vacuum to afford crude compound.

The crude product was purified by column chromatography using neutral silica gel of 60-120 mesh size. A gradient of 25-35% ethyl acetate in hexane was used for elution of the title compound. The final compound was further triturated with diethyl ether to afford the purified compound (0.011 g, 5%).

Step C

Benzyl-methyl-[6-(1H-pyrazol-4-yl)-quinoxalin-2-yl]-amine hydrochloride

To an ice cold solution of 4-[2-(Benzyl-methyl-amino)-quinoxalin-6-yl]-pyrazole-1-carboxylic acid tert-butyl ester (250 mg) in 1,4-dioxane (3 mL), HCl (in 1,4-dioxane) was added. The resulting mixture was allowed to warm to RT and was stirred further for 2 hours. After completion of the reaction the volatiles were evaporated under vacuum and the HCl salt of the final compound was triturated with DCM. The product was further purified by preparative HPLC (0.009 g, 3%).

Examples 1 to 8

By following the synthetic methods described above, modified as indicated in the table below, the compounds of Examples 3 to 8 were prepared.

| Ex. No. | Structure | Synthesis method and purification |
|---|---|---|
| 3 | 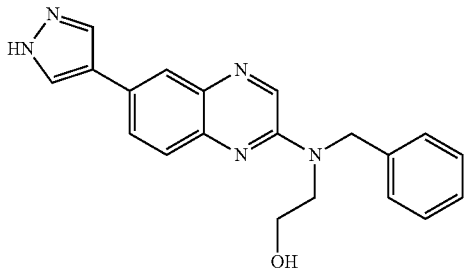 [SMILES: OCCN(Cc1ccccc1)c1cnc2cc(-c3cn[nH]c3)ccc2n1] | Example 3 was prepared by the same method as used for Example 2 except for the following:<br>For step A, 2-Benzylamino-ethanol was used instead of benzyl-methyl-amine<br>2-Benzylamino-ethanol is commercially available (Sigma-Aldrich) |
| 4 | 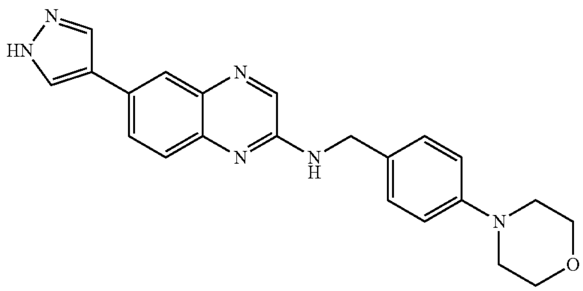 [SMILES: c1cc(N2CCOCC2)ccc1CNc1cnc2cc(-c3cn[nH]c3)ccc2n1] | Example 4 was prepared by the same method as used for Example 1 except for the following:<br>For step A, 4-Morpholin-4-yl-benzylamine was used instead of benzylamine.<br>4-Morpholin-4-yl-benzylamine is commercially available (Maybridge, Matrix, Apollo Scientific) |
| 5 | 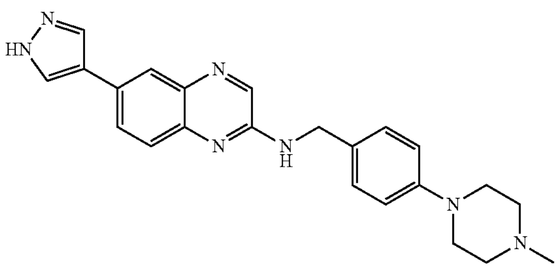 [SMILES: CN1CCN(c2ccc(CNc3cnc4cc(-c5cn[nH]c5)ccc4n3)cc2)CC1] | Example 5 was prepared by the same method as used for Example 1 except for the following:<br>For step A, 4-(4-Methyl-piperazin-1-yl)-benzylamine was used instead of benzylamine.<br>4-(4-Methyl-piperazin-1-yl)-benzylamine is commercially available (Apollo Scientific, Maybridge, Acros) |
| 6 | 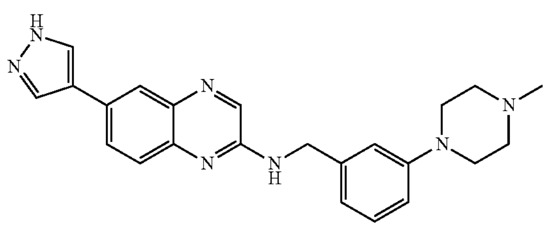 [SMILES: CN1CCN(c2cccc(CNc3cnc4cc(-c5cn[nH]c5)ccc4n3)c2)CC1] | Example 6 was prepared by the same method as used for Example 1 except for the following:<br>For step A, 3-(4-Methyl-piperazin-1-yl)-benzylamine was used instead of benzylamine.<br>3-(4-Methyl-piperazin-1-yl)-benzylamine is commercially available (Matrix Scientific, Maybridge, Acros) |
| 7 | 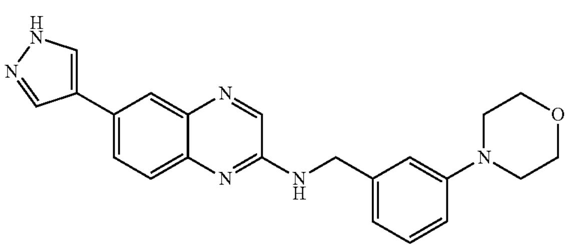 [SMILES: c1cc(CNc2cnc3cc(-c4cn[nH]c4)ccc3n2)cc(N2CCOCC2)c1] | Example 7 was prepared by the same method as used for Example 1 except for the following:<br>For step A, 3-Morpholin-4-yl-benzylamine was used instead of benzylamine.<br>3-Morpholin-4-yl-benzylamine is commercially available (Matrix Scientific, Maybridge, Acros) |
| 8 | 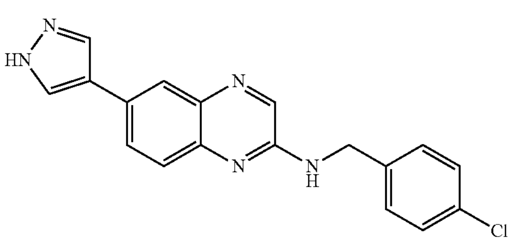 [SMILES: Clc1ccc(CNc2cnc3cc(-c4cn[nH]c4)ccc3n2)cc1] | Example 8 was prepared by the same method as used for Example 1 except for the following:<br>For step A, 4-Chloro-benzylamine was used instead of benzylamine. |

Example 9

(3-Chloro-benzyl)-[6-(1H-pyrazol-4-yl)-quinoxalin-2-yl]-amine

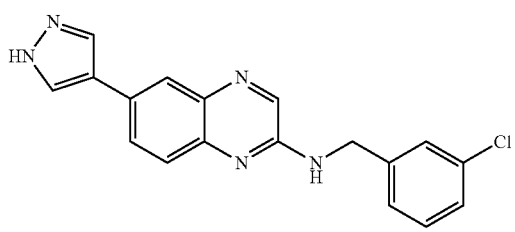 [SMILES: Clc1cccc(CNc2cnc3cc(-c4cn[nH]c4)ccc3n2)c1]

The title compound was prepared by the sequence of reactions shown in Scheme C below.

Scheme C

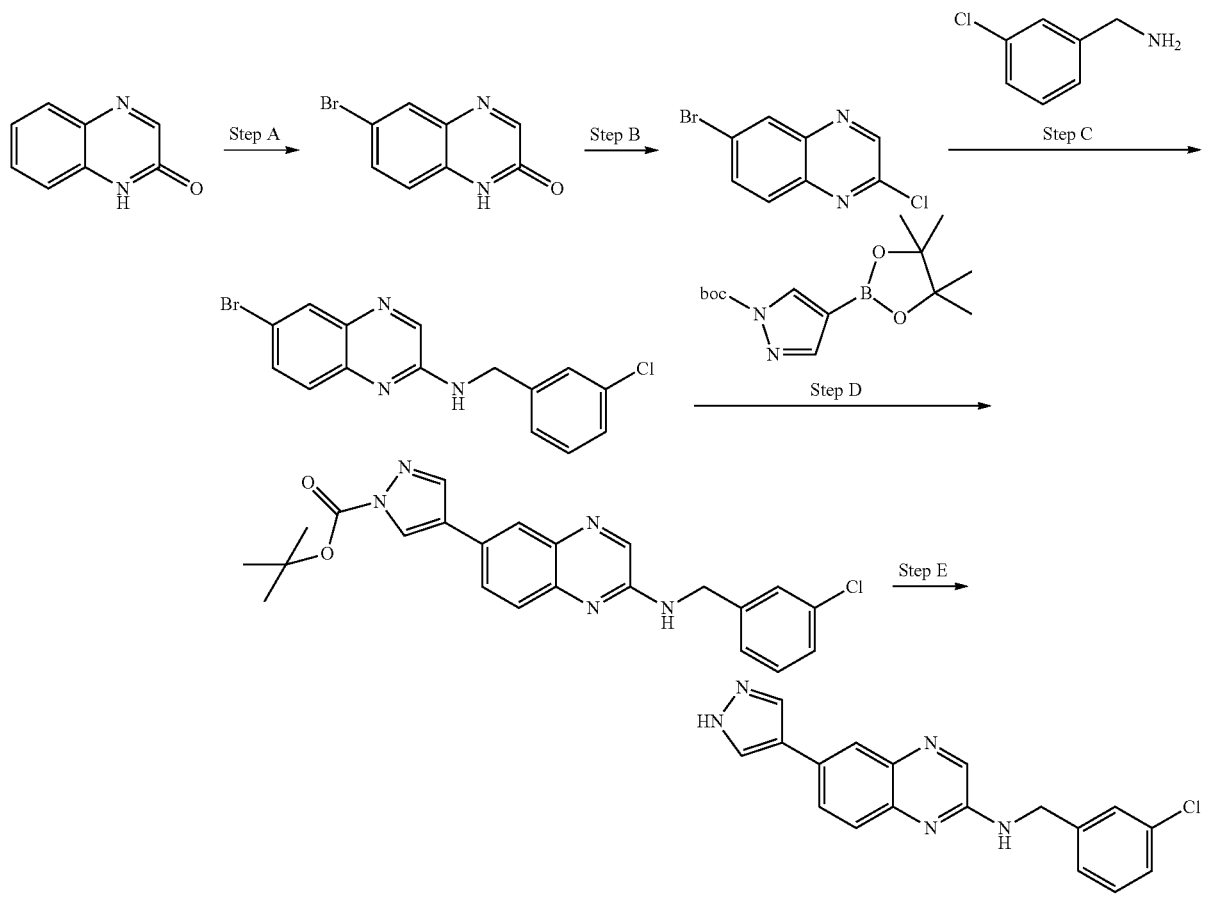

Step A

6-bromoquinoxalin-2(1H)-one

The quinoxalin-2(1H)-one (14.6 g, 0.1 mol, Aldrich, cat. no. 260517) and silver sulphate (15.6 g, 0.05 mol) were dissolved in conc. Sulfuric acid (100 ml) at 20° C. Bromine (5.2 ml, 0.1 mol) was added and the reaction mixture was stirred vigorously for 24 hours. The reaction mass was then diluted with carbon tetrachloride (100 mL), and this was heated at 50° C. The reaction mass was then filtered and the filtrate was poured into ice cold water and stirred for 30 minutes to obtain a precipitate. The precipitate was filtered and the solid material was dried in vacuo to afford the title product (9.0 g, 40%).

Step B

6-Bromo-2-chloro-quinoxaline 6-bromoquinoxalin-2(1H)-one (9.0 g, 40 mmol) was dissolved in $POCl_3$ (50 mL) and DMF (2 mL) was added at RT. The mixture was heated at 50° C. for 2 hours. After completion of the reaction it was cooled to RT and was poured slowly into ice cold water. The mixture was stirred for 30 minutes and then filtered to afford crude product.

The crude product was purified by column chromatography using neutral silica gel of 60-120 mesh size. A gradient of 8-9% DCM in hexane was used to elute the title compound (5.0 g, 51%).

$^1$H NMR (d6-DMSO) ☐ 9.03 (s, 1H), 8.42 (d, 1H), 8.08 (dd, 1H), 7.98 (d, 1H).

Step C

(6-Bromo-quinoxalin-2-yl)-(3-chloro-benzyl)-amine

To a solution of 6-Bromo-2-chloro-quinoxaline (0.3 g, 1 eq., 1.23 mmol) in DMSO (9 mL), was added 3-chloro benzyl amine (0.87 g, 5 eq., 6.2 mmol) at room temperature. The reaction mixture was stirred at room temperature overnight. After completion of the reaction, water (60 mL) was added and the reaction mixture was extracted with ethyl acetate (30 mL×3). The organic layer was washed with water (60 mL) and brine (60 mL), then dried over $Na_2SO_4$. The organic layer was concentrated under vacuum to obtain the crude product.

For final purification, column chromatography was used on neutral silica gel of 60-120 mesh size employing a gradient of 0-1% methanol in hexane to elute the title compound (0.39 g, 90%).

Step D

4-[2-(3-Chloro-benzylamino)-quinoxalin-6-yl]-pyrazole-1-carboxylic acid tert-butyl ester A mixture of (6-Bromo-quinoxalin-2-yl)-(3-chloro-benzyl)-amine (0.4 g, 1 eq., 1.15 mmol), 1-Boc-4-pyrazole boronic acid pinacol ester (0.4 g, 1.2 eq., 1.37 mmol), caesium carbonate (1.5 g, 4.0 eq., 4.6 mmol) and potassium iodide (0.019 g, 0.1 eq., 0.11 mmol) in 1,4-dioxane (22 mL) was degassed at RT under vacuum and then placed under an atmosphere of nitrogen. The process was repeated twice and Fu's catalyst (Bis(tri-tert-butylphosphine)palladium(0)) (0.058 g, 0.1 eq., 0.1 mmol) was added at room temperature. The reaction mixture was heated to 110° C. in a microwave reactor for 180 minutes. After completion of the reaction (confirmed by TLC), the organic mixture was diluted with ethyl acetate (200 mL) and washed with water (75 mL×3) then brine (75 mL). The organic layer was dried and concentrated to afford the crude product.

For final purification, column chromatography was used on neutral silica gel of 60-120 mesh size employing a gradient of 2-5% methanol in DCM to elute the title compound (0.150 g, 30%).

Step E

(3-Chloro-benzyl)-[6-(1H-pyrazol-4-yl)-quinoxalin-2-yl]-amine

To a solution of 4-[2-(3-Chloro-benzylamino)-quinoxalin-6-yl]-pyrazole-1-carboxylic acid tert-butyl ester (0.35 g, 0.80 mmol) in DCM (4 mL), was added HCl in dioxane (0.4 mL) at room temperature. After completion of the reaction, the reaction mixture was concentrated and washed with DCM (4 mL) to obtain the title compound (0.06 g, 22%).

Examples 10 to 20

By following the methods described above, modified as indicated, the compounds of Examples 10 to 20 were prepared.

10 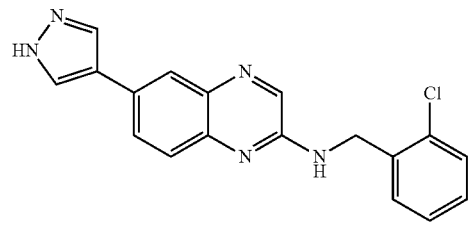 [SMILES: Clc1ccccc1CNc1cnc2cc(-c3cn[nH]c3)ccc2n1]

Example 10 was prepared by the same method as used for Example 1 except for the following:
For step A, 2-Chloro-benzylamine was used instead of benzylamine. For final purification, column chromatography was used on silica gel employing a gradient of 15-25% ethyl acetate in hexane to afford the desired compound (0.35 g, 91%).
For step B final purification, column chromatography was used on silica gel employing a gradient of 2-5% methanol in DCM to elute the desired compound (0.26 g, 73%).
For step C, following trituration in DCM, preparative TLC was used employing an eluting solvent system of DCM: Methanol (9:1) to elute the title compound (0.015 g, 7%)

11 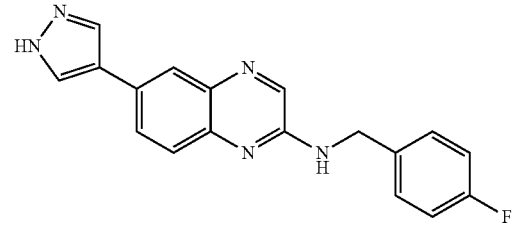 [SMILES: Fc1ccc(CNc2cnc3cc(-c4cn[nH]c4)ccc3n2)cc1]

Example 11 was prepared by the same method as used for Example 1 except for the following:
for step A, 4-fluoro-benzylamine was used instead of benzylamine.

12 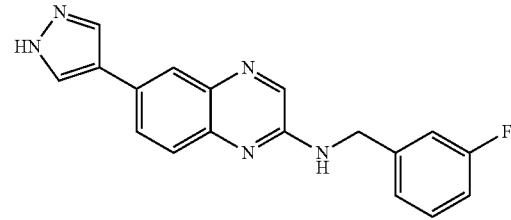 [SMILES: Fc1cccc(CNc2cnc3cc(-c4cn[nH]c4)ccc3n2)c1]

Example 12 was prepared by the same method as used for Example 1 except for the following:
For step A, 3-fluoro-benzylamine was used instead of benzylamine. For final purification, column chromatography was used on silica gel employing a gradient of 5-10% ethyl acetate in hexane to afford the desired compound (0.6 g, 92%).
For step B final purification, column chromatography was used on silica gel employing a gradient of 2-5% methanol in DCM to elute the desired compound (0.24 g, 30%).
For step C, following trituration in DCM, the HCl salt was isolated (0.044 g, 24%)

| | | |
|---|---|---|
| 13 | 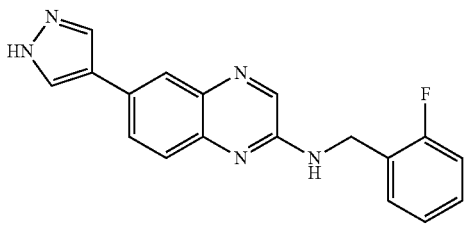 | Example 13 was prepared by the same method as used for Example 1 except for the following:<br>for step A, 2-fluoro-benzylamine was used instead of benzylamine. For final purification, column chromatography was used on silica gel employing a gradient of 5-10% ethyl acetate in hexane to afford the desired compound (0.62 g, 95%).<br>For step B final purification, column chromatography was used on silica gel employing a gradient of 2-4% methanol in DCM to elute the desired compound (0.22 g, 23%).<br>For step C, following trituration in DCM, the HCl salt was isolated (0.034 g, 20%) |
| 14 | 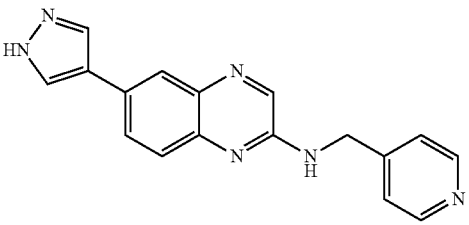 [SMILES: c1cc(CNc2cnc3cc(-c4cn[nH]c4)ccc3n2)ccn1] | Example 14 was prepared by the same method as used for Example 1 except for the following:<br>For step A, Pyridin-4-yl-methylamine should be used instead of benzylamine. |
| 15 | 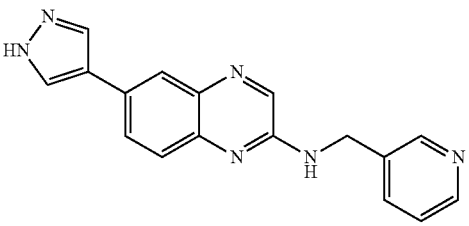 [SMILES: c1cncc(CNc2cnc3cc(-c4cn[nH]c4)ccc3n2)c1] | Example 15 was prepared by the same method as used for Example 1 except for the following:<br>For step A, Pyridin-3-yl-methylamine was used instead of benzylamine. For final purification, column chromatography was used on silica gel employing a gradient of 1-3% methanol in DCM to afford the desired compound (0.3 g, 88%).<br>For step B final purification, column chromatography was used on silica gel employing a gradient of 3-6% methanol in DCM to elute the desired compound (0.15 g, 34%).<br>For step C, following trituration in DCM, the HCl salt was isolated (0.045 g, 40%) |
| 16 | 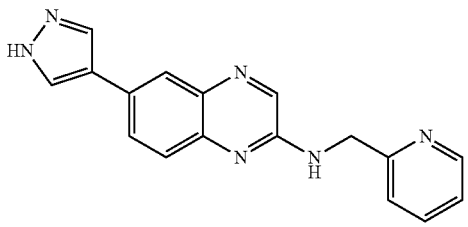 [SMILES: c1ccc(CNc2cnc3cc(-c4cn[nH]c4)ccc3n2)nc1] | Example 16 was prepared by the same method as used for Example 1 except for the following:<br>For step A, Pyridin-2-yl-methylamine was used instead of benzylamine. |
| 17 | 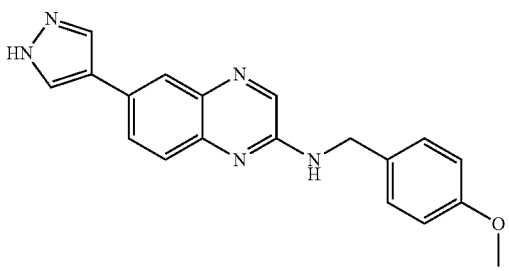 [SMILES: COc1ccc(CNc2cnc3cc(-c4cn[nH]c4)ccc3n2)cc1] | Example 17 was prepared by the same method as used for Example 1 except for the following:<br>For step A, 4-methoxy benzylamine was used instead of benzylamine. For final purification, column chromatography was used on silica gel employing a gradient of 5-15% ethyl acetate in hexane to afford the desired compound (0.8 g, 88%).<br>For step B final purification, column chromatography was used on silica gel employing a gradient of 20-30% ethyl acetate in hexane to elute the desired compound. (0.15 g, 34%).<br>For step C, following trituration in DCM, the HCl salt was purified by prep HPLC to afford the title compound (0.003 g, 2%) |
| 18 | 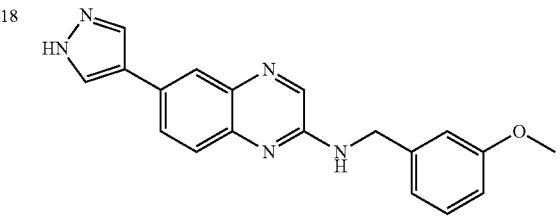 | Example 18 was prepared by the same method as used for Example 1 except for the following:<br>For step A, 3-methoxy benzylamine was used instead of benzylamine. For final purification, column chromatography was used on silica gel employing a gradient of 5-15% ethyl acetate in hexane to afford the desired compound (0.3 g, 80%).<br>For step B final purification, column chromatography was used on silica gel employing a gradient of 20-30% ethyl acetate in hexane to elute the desired compound. (0.12 g, 28%).<br>For step C, following trituration in DCM, the HCl salt was purified by prep HPLC to afford the title compound (0.032 g, 21%) |

| | | |
|---|---|---|
| 19 | 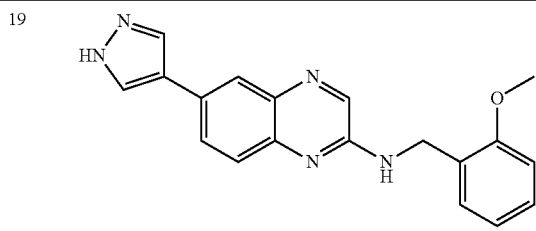 | Example 19 was prepared by the same method as used for Example 1 except for the following:<br>For step A, 2-methoxy benzylamine was used instead of benzylamine. For final purification, column chromatography was used on silica gel employing a gradient of 5-15% ethyl acetate in hexane to afford the desired compound (0.445 g, 88%).<br>For step B final purification, column chromatography was used on silica gel employing a gradient of 20-30% ethyl acetate in hexane to elute the desired compound (0.18 g, 42%).<br>For step C, following trituration in DCM, the HCl salt was purified by prep HPLC to afford the title compound (0.005 g, 4%) |
| 20 | 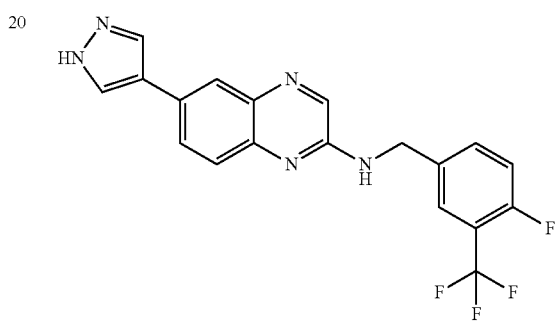 | Example 20 was prepared by the same method as used for Example 1 except for the following:<br>For step A, 4-Fluoro-3-trifluoromethyl-benzylamine was used instead of benzylamine. |

Example 21

(4-Fluoro-benzyl)-methyl-[6-(1H-pyrazol-4-yl)-quinoxalin-2-yl]-amine

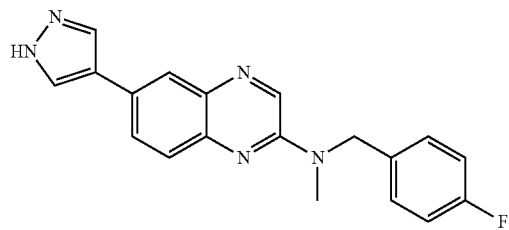 [SMILES: CN(Cc1ccc(F)cc1)c1cnc2cc(-c3cn[nH]c3)ccc2n1]

The title compound was prepared by the synthetic route shown in Scheme D below.

Scheme D

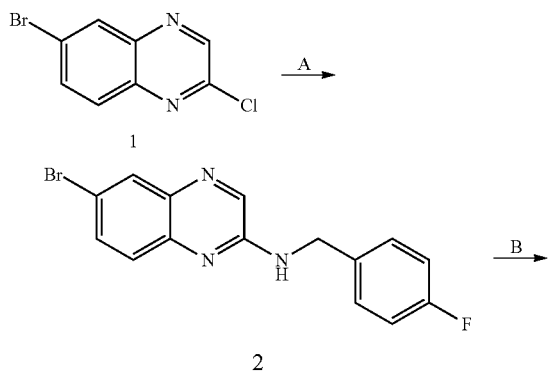

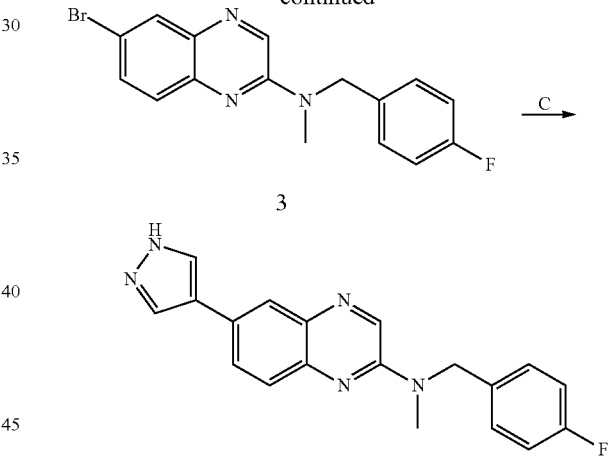

Step A

(6-Bromo-quinoxalin-2-yl)-(4-fluoro-benzyl)-amine 6-bromo, 2-chloroquinoxaline (0.25 g, 1.02 mmol) was dissolved in DMSO (8 mL) at room temperature and 4-fluoro benzyl amine (0.64 g, 5.1 mmol) was added. The reaction mixture was stirred at room temperature overnight. After completion of the reaction, the reaction mixture was poured onto ice water (100 mL) with stirring for 30 minutes. The precipitated product was filtered off and washed by water and dried in vacuo to afford the solid crude product.

The product was purified by column chromatography using neutral silica gel of 60-120 mesh size. A gradient of 1-2% methanol in DCM was used to elute the title compound (0.35 g, 100%).

Step B

(6-Bromo-quinoxalin-2-yl)-(4-fluoro-benzyl)-methyl-amine (6-Bromo-quinoxalin-2-yl)-(4-fluoro-benzyl)-amine (0.35 g, 1.0 mmol) was added to a suspension of sodium hydride (0.037 g, 1.5 mmol) in DMF (5 mL) at room temperature and it was stirred for 15 minutes. The reaction mixture was cooled down to 5-10° C. and methyl iodide (0.17 g, 1.2 mmol) was added at 5-10° C. and this was maintained for 30 minutes. After completion of the reaction, the reaction mixture was gradually poured into ice cold water (30 mL) and stirred for a further 30 minutes. The precipitated product was filtered and washed by water and dried under vacuum to afford the title compound (0.4 g) which was used directly for the next step.

Step C

(4-Fluoro-benzyl)-methyl-[6-(1H-pyrazol-4-yl)-quinoxalin-2-yl]-amine (6-Bromo-quinoxalin-2-yl)-(4-fluoro-benzyl)-methyl-amine (0.4 g, 1.1 mmol), 1-Boc-4-pyrazole boronic acid pinacol ester (0.4 g, 1.3 mmol), caesium carbonate (1.5 g, 4.6 mmol) and potassium iodide (0.018 g, 0.1 mmol) were dissolved in 1,4-dioxane (20 mL) at room temperature. The reaction mixture was degassed at RT under vacuum and placed under an atmosphere of nitrogen. The process was repeated twice and slowly Bis(tri-tert-butylphosphine)palladium(0) (0.059 g 0.1 mmol) was added at room temperature. The reaction mixture was heated by microwave irradiation at 110° C. for 180 min. After completion of the reaction, the reaction mixture was diluted with ethyl acetate (150 mL) and washed with water (3×20 mL) and brine (20 mL). The organic volatiles were removed under vacuum to give a residual solid.

The product was purified by column chromatography using neutral silica gel of 60-120 mesh size. A gradient of 1-4% methanol in DCM was used for elution of a mixture of the title compound and the Boc-protected derivative (0.2 g for the mixture). The mixture was further purified by prep.TLC and then prep. HPLC to obtain the title compound (0.015 g, 4%).

Examples 22 to 28

By following the methods described above, modified as indicated, the compounds of Examples 22 to 28 were prepared.

| | | |
|---|---|---|
| 22 | 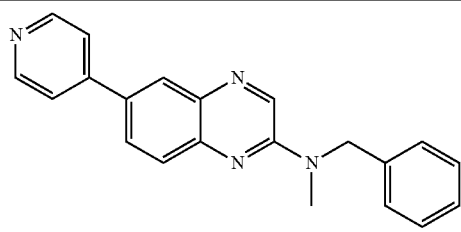 | Example 22 was prepared by the same method as used for Example 21 except for the following:<br>For step A, benzylamine was used instead of 4-Fluoro-benzylamine.<br>For step C, Boronic acid, B-4-pyridinyl- was used instead of 4-(4,4,5,5-Tetramethyl-[1,3,2]dioxaborolan-2-yl)-pyrazole-1-carboxylic acid tert-butyl ester. |
| 23 | 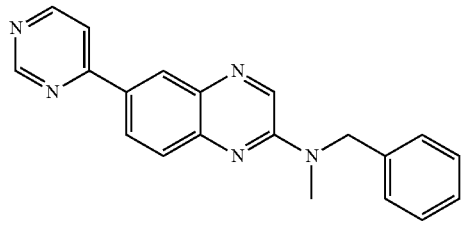 [SMILES: CN(Cc1ccccc1)c1cnc2cc(-c3ccncc3)ccc2n1] | Example 23 was prepared by the same method as used for Example 21 except for the following:<br>For step A, benzylamine was used instead of 4-Fluoro-benzylamine.<br>For step C, Boronic acid, B-4-pyrimidinyl- was used instead of 4-(4,4,5,5-Tetramethyl-[1,3,2]dioxaborolan-2-yl)-pyrazole-1-carboxylic acid tert-butyl ester |
| 24 | 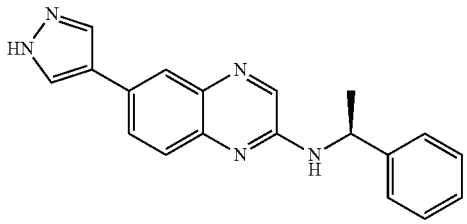 [SMILES: C[C@H](Nc1cnc2cc(-c3cn[nH]c3)ccc2n1)c1ccccc1] | Example 24 was prepared by the same method as used for Example 1 except for the following:<br>For step A, (S)-1-Phenyl-ethylamine was used instead of benzylamine. |
| 25 | 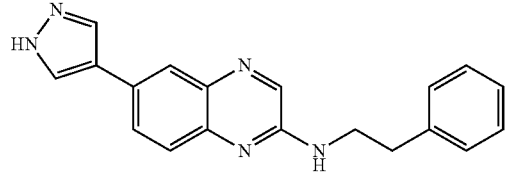 [SMILES: c1ccc(CCNc2cnc3cc(-c4cn[nH]c4)ccc3n2)cc1] | Example 25 was prepared by the same method as used for Example 1 except for the following:<br>For step A, Phenethylamine was used instead of benzylamine. For final purification, column chromatography was used on silica gel eluting with 5% methanol in DCM to afford the desired compound (0.42 g, 98%).<br>For step B final purification, column chromatography was used on silica gel employing a gradient of 1-2% methanol in DCM to elute the desired compound (0.15 g, 30%).<br>For step C, following trituration in DCM followed by n-pentane, the title compound was isolated as the HCl salt (0.026 g) |

| | | |
|---|---|---|
| 26 | 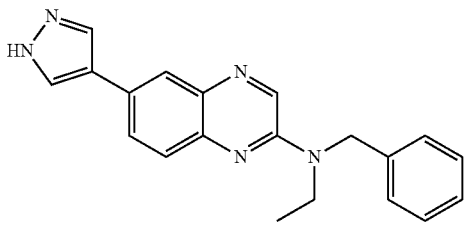 [SMILES: CCN(Cc1ccccc1)c1cnc2cc(-c3cn[nH]c3)ccc2n1] | Example 26 was prepared by the same method as used for Example 21 except for the following:<br>For step A, benzylamine was used instead of 4-Fluoro-benzylamine.<br>For step B, ethyl iodide was used instead of methyl iodide. |
| 27 | 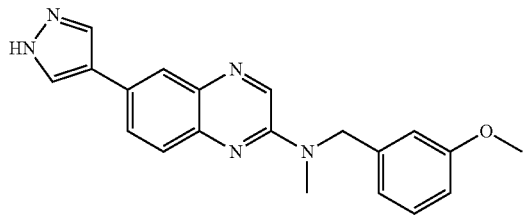 | Example 27 was prepared by the same method as used for Example 21 except for the following:<br>For step A, 3-methoxybenzylamine was used instead of 4-Fluoro-benzylamine. |
| 28 | 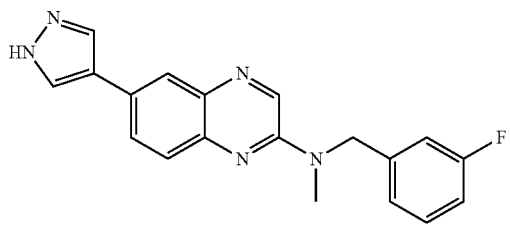 [SMILES: CN(Cc1cccc(F)c1)c1cnc2cc(-c3cn[nH]c3)ccc2n1] | Example 35 was prepared by the same method as used for Example 21 except for the following:<br>For step A, 3-Fluoro-benzylamine was used instead of 4-Fluoro-benzylamine. |

Example 29

(4-Fluoro-3-trifluoromethyl-benzyl)-methyl-[6-(1H-pyrazol-4-yl)-quinoxalin-2-yl]-amine

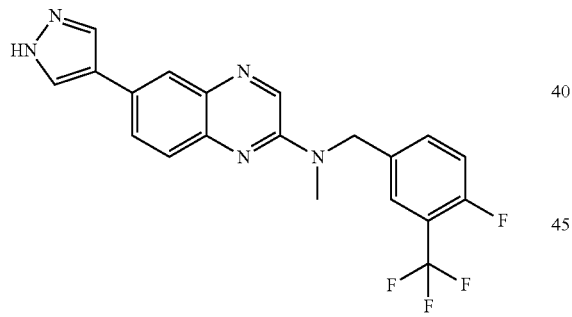

The title compound was prepared by the sequence of reactions shown in Scheme E below.

Scheme E

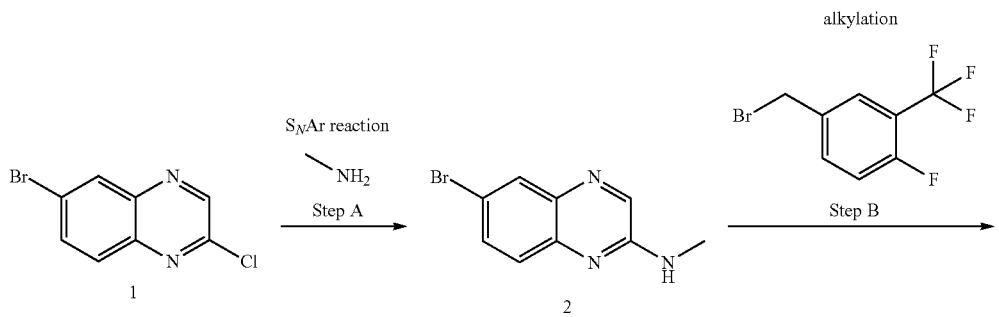

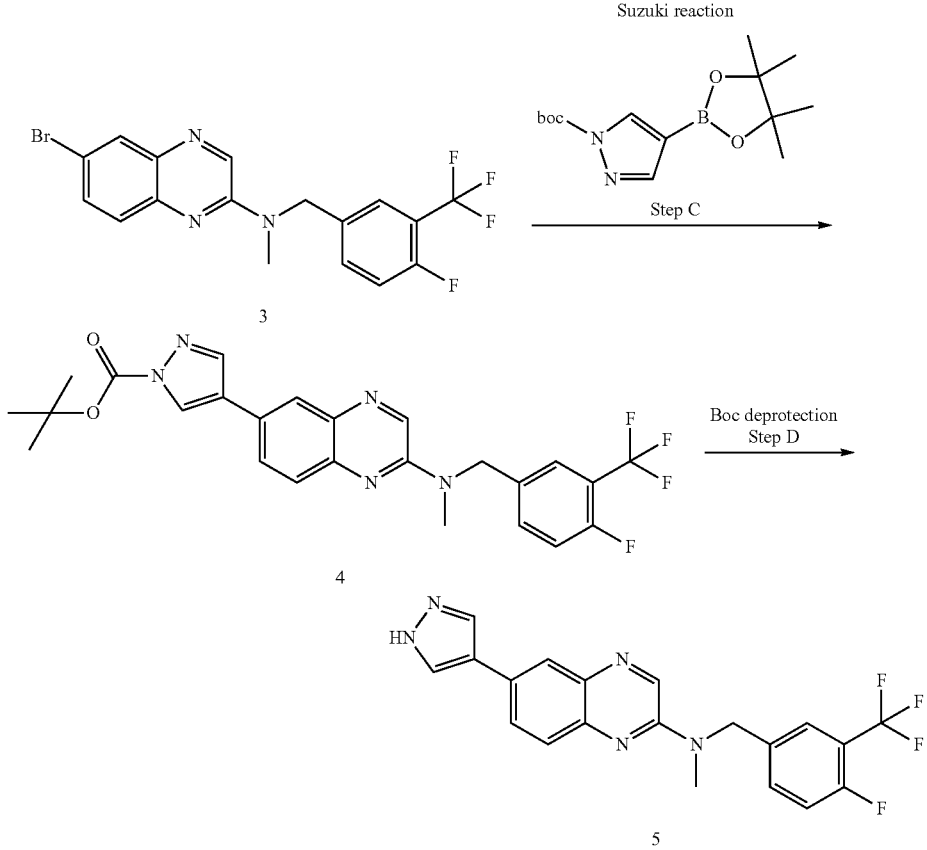

Step A

(6-Bromo-quinoxalin-2-yl)-methyl-amine

To solution of 6-bromo-2-chloro-quinoxaline (0.7 g, 1 eq, 2.87 mmol) in THF (6 mL) was added a solution of methyl amine in THF (3 mL) at room temperature. The mixture was stirred at room temperature for 2 h. After completion of the reaction, the volatiles were removed under vacuum and water (20 mL) was added to reaction mixture. The aqueous layer was extracted with ethyl acetate (15 mL×3). The organic layer was washed with water (20 mL) and brine (20 mL) and then dried over $Na_2SO_4$. The organic layer was concentrated under vacuum to afford the crude product.

For final purification, column chromatography was used on neutral silica gel of 60-120 mesh size employing a gradient of 3-5% ethyl acetate in hexane to elute the title compound (0.6 g, 87%).

Step B

(6-Bromo-quinoxalin-2-yl)-(4-fluoro-3-trifluoromethyl-benzyl)-methyl-amine

To a suspension of sodium hydride (0.08 g, 1.5 eq, 3.37 mmol) in DMF (15 mL) was added (6-Bromo-quinoxalin-2-yl)-methyl-amine (0.6 g, 1.0 eq, 2.51 mmol) at 0° C. The reaction mixture was stirred at 0° C. for 15 minutes. A mixture of 4-(bromomethyl)-1-fluoro-2-(trifluoromethyl)benzene (0.7 g, 1.2 eq. 2.72 mmol) in DMF (15 mL) was added at room temperature and the reaction mixture was stirred for 2.0 hours at 0° C. After completion of the reaction, cold water (180 mL) was added and the reaction mixture was stirred for 15 minutes then filtered. The solid was dried under vacuum to afford the title compound (0.7 g, 67%).

Step C

4-{2-[(4-Fluoro-3-trifluoromethyl-benzyl)-methylamino]-quinoxalin-6-yl}-pyrazole-1-carboxylic acid tert-butyl ester A mixture of (6-Bromo-quinoxalin-2-yl)-(4-fluoro-3-trifluoromethyl-benzyl)-methyl-amine (0.35 g, 1 eq, 0.84 mmol), 1-Boc-4-pyrazole boronic acid pinacol ester (0.3 g, 1.2 eq, 1.01 mmol), caesium carbonate (1.1 g, 4.0 eq, 3.3 mmol) and potassium iodide (0.014 g, 0.1 eq, 0.84 mmol) in 1,4-dioxane (15 mL) was degassed at RT under vacuum and then placed under an atmosphere of nitrogen. The process was repeated twice and Fu's catalyst (Bis(tri-tert-butylphosphine)palladium(0)) (0.02 g, 0.05 eq, 0.04 mmol) was added at room temperature. The reaction mixture was heated at 108° C. in a microwave reactor for 180 min. After completion of the reaction (confirmed by TLC), the organic mixture was diluted with ethyl acetate (325 mL) and washed with water (100 mL×3) followed by brine (100 mL). The organic solvent was dried and concentrated to give a solid residue.

For final purification, column chromatography was used on neutral silica gel of 60-120 mesh size employing a gradient of 1-2% methanol in DCM to elute the title compound (0.15 g, 35%).

Step D

(4-Fluoro-3-trifluoromethyl-benzyl)-methyl-[6-(1H-pyrazol-4-yl)-quinoxalin-2-yl]-amine To a solution of 4-{2-[(4-Fluoro-3-trifluoromethyl-benzyl)-methyl-amino]-quinoxalin-6-yl}-pyrazole-1-carboxylic acid tert-butyl ester (0.15 g, 0.299 mmol) in DCM (1.5 mL) was added HCl in dioxane (1.0 mL) at room temperature. The reaction mixture was stirred for 2 hours. After completion of the reaction, the reaction mixture was concentrated and washed with diethyl ether (5.0 mL) to afford the HCl salt (75 mg). The compound was basified by ammonia in THF and was further purified by preparative TLC to afford the title compound (0.035 g, 29%).

The mobile phase used for the Preparative TLC was DCM:Methanol (9:1).

Examples 30 and 31

By following the methods described above, modified as indicated, the compounds of Examples 30 and 31 were prepared.

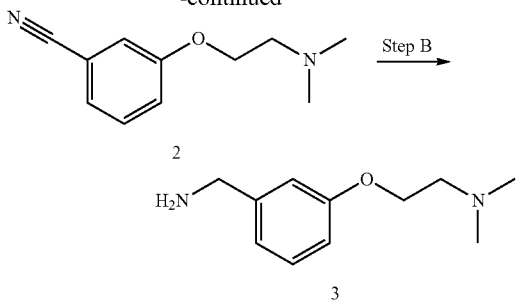

Step A

3-(2-Dimethylamino-ethoxy)-benzonitrile

A stirred suspension of sodium hydride (0.84 g, 2.5 eq, 21 mmol) in DMF (30 mL) was cooled down to 0° C. and a solution of 3-cyano phenol (1.0 g, 1.0 eq, 8.4 mmol) in DMF (30 mL) was slowly added at 0° C. The reaction mixture was stirred for 30 minutes and 2-(chloro-ethyl)-dimethyl-amine (1.44 g, 1.2 eq, 10.0 mmol) was added at 0° C. The reaction mixture was heated to 80° C. overnight. After completion of the reaction, the reaction mass was poured into water (300 mL) and extracted using ethyl acetate (3×50 mL). The organic layer was dried over sodium sulphate and concentrated in vacuo to afford the crude product.

The crude product was purified by column chromatography using neutral silica gel of 60-120 mesh size. A gradient of 25% ethyl acetate in hexane was used to elute the title compound (0.5 g, 13%).

Step B

2(3-Aminomethyl-phenoxy)-ethyl-dimethyl-amine 3-(2-Dimethylamino-ethoxy)-benzonitrile (0.8 g, 1 eq, 4.1 mmol) was dissolved in THF (80 mL) and cooled down to 0-5° C. A 1.0 M solution of lithium aluminium hydride in THF (0.47 g, 3.0 eq, 12.3 mmol) was added at 0-5° C. The reaction mixture was allowed to warm to RT and was stirred for 4 hrs. After completion of the reaction (confirmed by TLC), ethyl acetate at 0-5° C. was slowly added to quench any excess of lithium aluminium hydride in the reaction mixture,

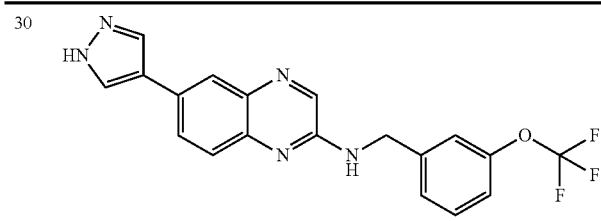

30

Example 30 was prepared by the same method as used for Example 1 except for the following:
For step A, 3-Trifluoromethoxy-benzylamine was used instead of benzylamine.

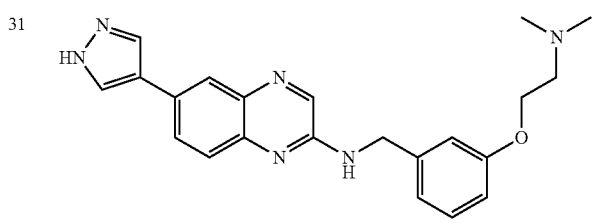

31

Example 31 was prepared by the same method as used for Example 1 except for the following:
For step A, [2-(3-Aminomethyl-phenoxy)-ethyl]-dimethyl-amine was used instead of benzylamine
Refer to Scheme F below for the preparation of [2-(3-aminomethyl-phenoxy)-ethyl]-dimethyl-amine.

Preparation of [2-(3-aminomethyl-phenoxy)-ethyl]-dimethyl-amine

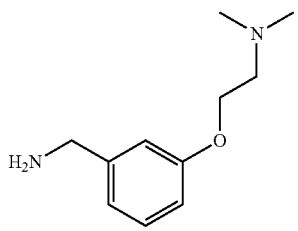

The title compound was prepared by the synthetic route shown in Scheme F below.

Scheme F

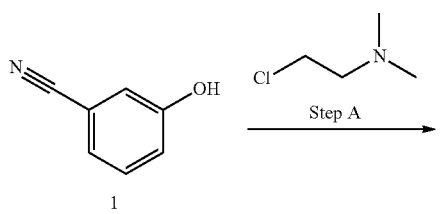

followed by addition of saturated sodium sulphate solution (2 mL). The reaction mass was filtered through hy-flow bed and the filtrate was concentrated in vacuo to obtain the crude product.

The crude product was purified by column chromatography using neutral silica gel of 60-120 mesh size. A gradient of 3-4% methanol in DCM was used to elute the title compound (0.5 g, 63%).

Example 32

3,4-Difluoro-benzyl)-[641H-pyrazol-4-yl)-quinoxalin-2-yl]-amine

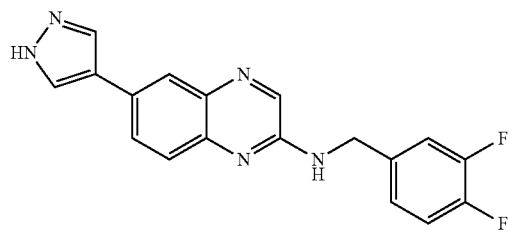 [SMILES: Fc1ccc(CNc2cnc3cc(-c4cn[nH]c4)ccc3n2)cc1F]

The title compound was prepared by the same method as used for Example 1 except that, in step A, 3,4-Difluoro-benzylamine was used instead of benzylamine.

Example 33

((R)-1-Phenyl-ethyl)-[6-(1H-pyrazol-4-yl)-quinoxalin-2-yl]-amine

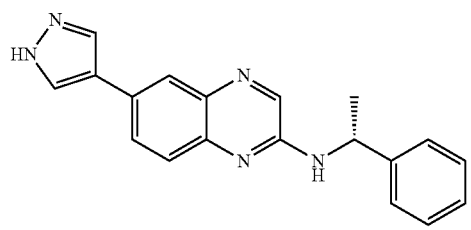 [SMILES: C[C@@H](Nc1cnc2cc(-c3cn[nH]c3)ccc2n1)c1ccccc1]

The title compound was prepared by the sequence of reactions shown in Scheme G below.

Scheme G

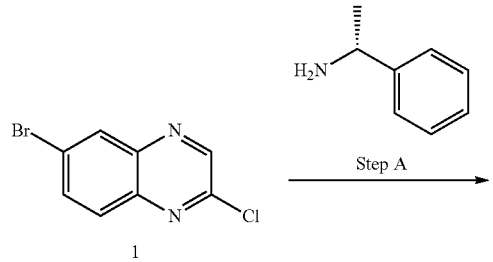

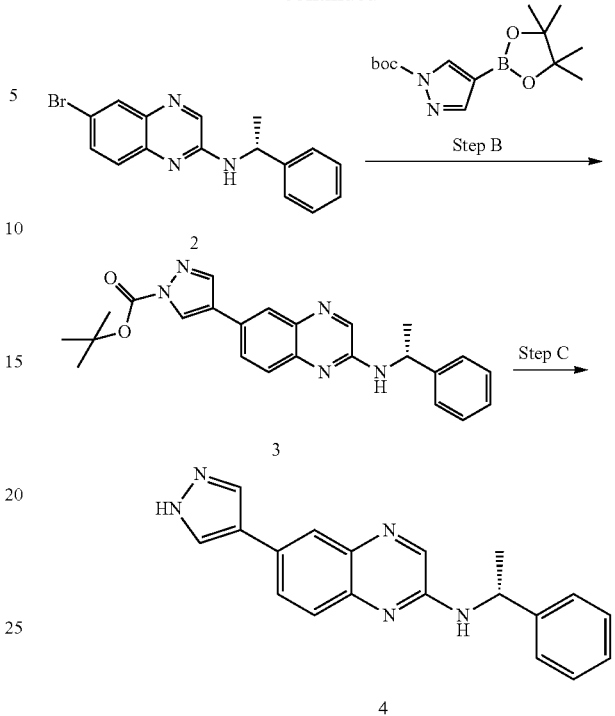

Step A (6-Bromo-quinoxalin-2-yl)-((R)-1-phenyl-ethyl)-amine

To a solution of 6-Bromo-2-chloro-quinoxaline (0.45 g, 1 eq, 1.85 mmol) in DMSO (6 mL), was added (R)-1-phenylethanamine (0.67 g, 3 eq, 5.55 mmol) at room temperature. The mixture was stirred overnight. After completion of the reaction (confirmed by TLC), cold water (40 mL) was added to the reaction mixture and this was stirred for 1 hour at room temperature. The precipitate was filtered off, washed with water (10 mL) and then dried under vacuum to afford the title compound (0.48 g, 79%).

Step B

4-[2-((R)-1-Phenyl-ethylamino)-quinoxalin-6-yl]-pyrazole-1-carboxylic acid tert-butyl ester A mixture of (6-Bromo-quinoxalin-2-yl)-((R)-1-phenyl-ethyl)-amine (0.42 g, 1 eq, 1.28 mmol), 1-boc-4-pyrazole boronic acid pinacol ester (0.45 g, 1.2 eq, 1.53 mmol), caesium carbonate (1.66 g, 4.0 eq, 5.1 mmol) and potassium iodide (0.021 g, 0.1 eq, 0.13 mmol) in 1,4-dioxane (20 mL) was degassed at RT under vacuum and then placed under an atmosphere of nitrogen. The process was repeated twice and Fu's catalyst (Bis(tri-tert-butylphosphine)palladium(0)) (0.033 g, 0.05 eq, 0.06 mmol) was added at room temperature. The reaction mixture was heated at 108° C. in a microwave reactor for 180 minutes. After completion of the reaction (confirmed by TLC), the reaction mixture was diluted with ethyl acetate (200 mL) and then washed with water (50 mL×3) and brine (50 mL). The organic layer was dried and concentrated to give the crude product.

For final purification, column chromatography was used on neutral silica gel of 60-120 mesh size employing a gradient of 1-3% methanol in DCM to elute the title compound (0.25 g, 47%).

Step C ((R)-1-Phenyl-ethyl)-[6-(1H-pyrazol-4-yl)-quinoxalin-2-yl]-amine

To a solution of 4-[2-((R)-1-Phenyl-ethylamino)-quinoxalin-6-yl]-pyrazole-1-carboxylic acid tert-butyl ester (0.25 g, 0.602 mmol) in DCM (4 mL) was added 4M HCl in dioxane (1.0 mL) at room temperature. The mixture was stirred for 2 hours. After completion of the reaction, the reaction mass was concentrated in vacuo to afford the crude HCl salt (0.2 g).

The crude HCl salt was basified with ammonia in THF and was purified by preparative TLC to afford the title compound (0.030 g, 16%).

The mobile phase used for preparative TLC was DCM: Methanol (9:1).

Example 34

Benzyl-methyl-[1-oxy-7-(1H-pyrazol-4-yl)-benzo[1,2,4]triazin-3-yl]-amine

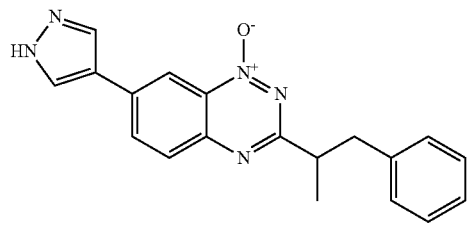 [SMILES: CC(Cc1ccccc1)c1nc2ccc(-c3cn[nH]c3)cc2[n+]([O-])n1]

The title compound was prepared by the sequence of reactions shown in Scheme H below.

Scheme H

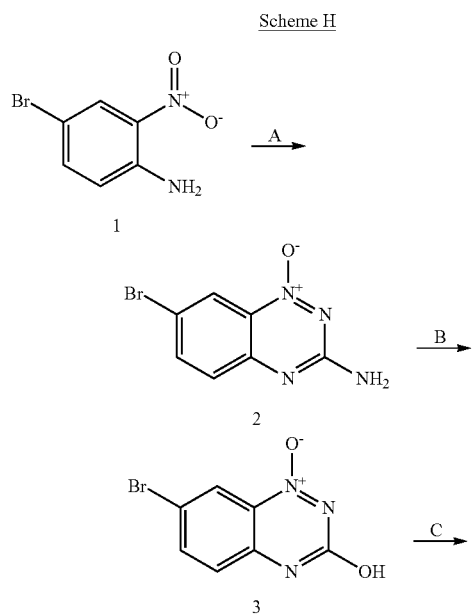

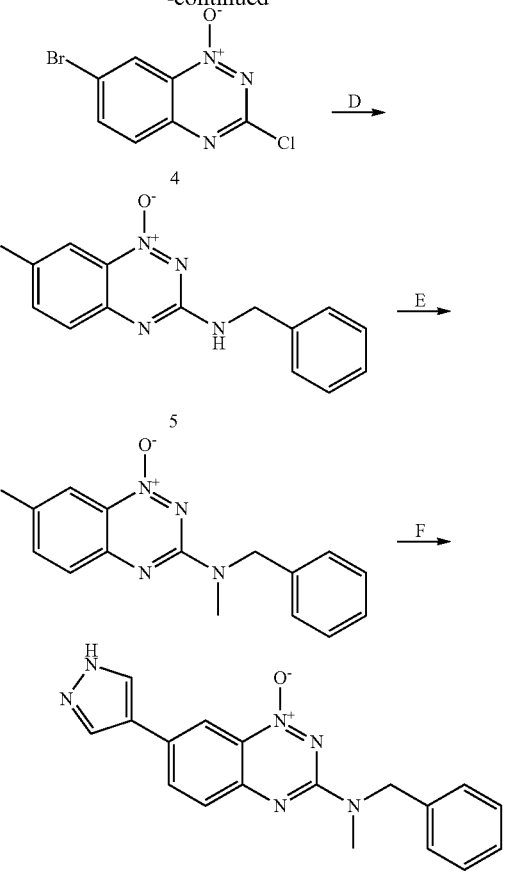

Step A

7-Bromo-1-oxy-benzo[1,2,4]triazin-3-ylamine

A mixture of 4-bromo-2-nitro-phenylamine (10 g, 46 mmol, commercially available: ABCR, AB145585) and cyanamide (2 g, 30 mmol) was heated at 100° C. and cooled to 50° C. To it was slowly added HCl (20 mL) and the mixture was heated at 100° C. for 3 h. The mixture was cooled to rt and to it was added NaOH (7.5 M, 50 mL). The mixture was heated at 100° C. for 1 h, cooled to rt and diluted with water. The mixture was filtered and washed with ether to afford the title compound (11 g, 99%) as a yellow solid.

Step B

7-Bromo-1-oxy-benzo[1,2,4]triazin-3-ol

To a solution of 7-bromo-1-oxy-benzo[1,2,4]triazin-3-ylamine (11 g, 46 mmol) in TFA (100 mL) at 0° C. was slowly added NaNO$_2$ (5 g, 73 mmol). The reaction mixture was stirred at rt for 2 h and poured into ice-water. The mixture was stirred for 30 min and filtered. The solid was washed with water and dried to afford 7-Bromo-1-oxy-benzo[1,2,4]triazin-3-ol (11 g, 100%) as a yellow solid.

Step C

7-Bromo-3-chloro-benzo[1,2,4]triazine 1-oxide

A solution of 7-bromo-1-oxy-benzo[1,2,4]triazin-3-ol (11 g, 46 mmol) in POCl$_3$ (50 mL) was heated under reflux for 16 h, cooled to rt, poured into ice-water and stirred for 30 min. The mixture was filtered, washed with water and dried to afford 7-Bromo-3-chloro-benzo[1,2,4]triazine 1-oxide (5 g, 42%) as a yellow solid.

Step D

Benzyl-(7-bromo-1-oxy-benzo[1,2,4]triazin-3-yl)-amine

To a solution of 7-bromo-3-chloro-benzo[1,2,4]triazine 1-oxide (1.1 g, 1 eq, 4.22 mmol) in DMSO (10 mL) was added benzyl amine (1.13 g, 2.5 eq, 10.5 mmol) at room temperature. The reaction mixture was stirred for 3 hours at room temperature. After completion of the reaction, cold water (70 mL) was added to the reaction mixture and it was stirred for 1 hour at room temperature. The precipitate was filtered and washed with water (10 mL) and then dried under vacuum to afford the title compound (1.1 g, 78%).

Step E

Benzyl-(7-bromo-1-oxy-benzo[1,2,4]triazin-3-yl)-methyl-amine

To a suspension of sodium hydride (0.14 g, 1.6 eq, 5.83 mmol) in DMF (5 mL) at 0° C. was added an ice-cooled solution of benzyl-(7-bromo-1-oxy-benzo[1,2,4]triazin-3-yl)-amine (1.2 g, 1.0 eq, 3.62 mmol) in DMF (25 mL). The reaction mixture was stirred at 0° C. for 15 minutes. A solution of methyl iodide (0.67 g, 1.3 eq. 4.7 mmol) in DMF (25 mL) was then added at 0° C. and the reaction mixture was stirred for 2.0 hours at 0° C. After completion of the reaction, water (150 mL) was added to the reaction mixture and the aqueous was extracted with ethyl acetate (25 mL×3). The organic layer was washed with water (100 mL) and brine (100 mL) and was then dried over Na$_2$SO$_4$. The organic layer was concentrated under vacuum to afford crude product.

For final purification, column chromatography was used on neutral silica gel employing a gradient of 5-10% ethyl acetate in hexane to elute the title compound (1.0 g, 80%).

Step F

Benzyl-methyl-[1-oxy-7-(1H-pyrazol-4-yl)-benzo[1,2,4]triazin-3-yl]-amine

A mixture of benzyl-(7-bromo-1-oxy-benzo[1,2,4]triazin-3-yl)-methyl-amine (0.6 g, 1 eq, 1.7 mmol), 1-Boc-4-pyrazole boronic acid pinacol ester (0.51 g, 1.0 eq, 1.7 mmol), caesium carbonate (2.26 g, 4.0 eq, 6.95 mmol) and potassium iodide (0.029 g, 0.1 eq, 0.17 mmol) in 1,4-dioxane (30 mL) was degassed at RT under vacuum and then placed under an atmosphere of nitrogen. The process was repeated twice and Fu's catalyst (Bis(tri-tert-butylphosphine)palladium(0)) (0.045 g, 0.05 eq, 0.09 mmol) was added at room temperature. The reaction mixture was heated at 108° C. in a microwave reactor for 180 minutes. After completion of the reaction (confirmed by TLC), the mixture was diluted with ethyl acetate (300 mL) and was washed with water (100 mL×3) and brine (100 mL). The organic solvent was dried over Na$_2$SO$_4$ and concentrated to give a crude residue.

For final purification, column chromatography was used on neutral silica gel employing a gradient of 0-3% methanol in DCM to elute the title compound (0.15 g). The compound was further purified by Preparative TLC to afford the pure product (0.019 g, 3%).

Example 35

Benzyl-methyl-[7-(1H-pyrazol-4-yl)-benzo[1,2,4]triazin-3-yl]-amine

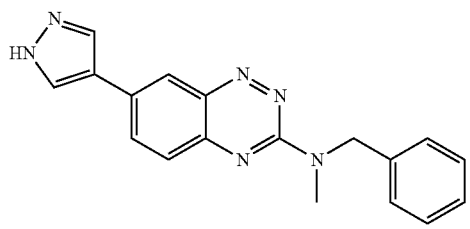 [SMILES: CN(Cc1ccccc1)c1nnc2cc(-c3cn[nH]c3)ccc2n1]

To a solution of benzyl-methyl-[1-oxy-7-(1H-pyrazol-4-yl)-benzo[1,2,4]triazin-3-yl]-amine (1.0 eq., 0.15 mg, 0.45 mol, refer to Example 34 for preparation) in ethanol (12 mL) was added water (3 mL) followed by sodium dithionite (4 eq., 0.32 g, 1.8 mmol) at RT. The reaction was stirred for 1.0 hour at 70° C. After completion of the reaction, the reaction was cooled to room temperature and the reaction mixture was concentrated in vacuo at 40° C. The product was extracted from residue using ethyl acetate (3×50 mL) and the ethyl acetate layer was dried over anhydrous sodium sulphate and then concentrated under reduced pressure to afford a yellow solid (0.13 g).

The compound was further purified by Preparative TLC to afford the title compound (0.030 g, 21%).

The mobile phase used for the preparative TLC was DCM: Methanol (9.5:0.5).

Examples 36 to 39

By following the methods described above, modified as indicated, the compounds of Examples 36 to 39 were prepared.

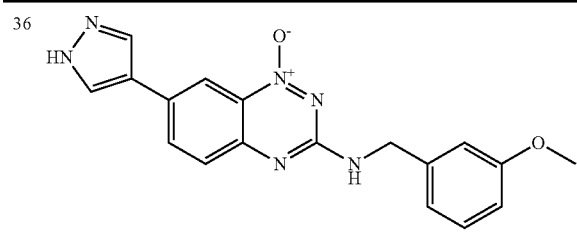

36

Example 36 was prepared by the same method as used for Example 34 except for the following:
For step D, 3-methoxy-benzylamine was used instead of benzylamine.
Step E (N-methylation reaction) was omitted.

| | | |
|---|---|---|
| 37 | 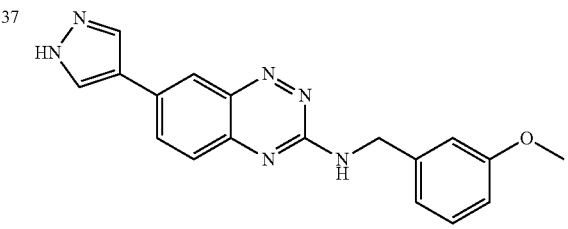 | Example 37 was prepared by the same method as used for Example 35 except for the following:<br>In step A, (3-methoxy-benzyl)-[1-oxy-7-(1H-pyrazol-4-yl)-benzo[1,2,4]triazin-3-yl]-amine (Example 36) was used as starting material |
| 38 | 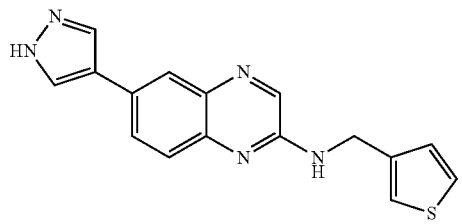 [SMILES: c1cc(CNc2cnc3cc(-c4cn[nH]c4)ccc3n2)cs1] | Example 38 was prepared by the same method as used for Example 1 except for the following:<br>For step A, thiophen-3-yl-methylamine was used instead of benzylamine. |
| 39 | 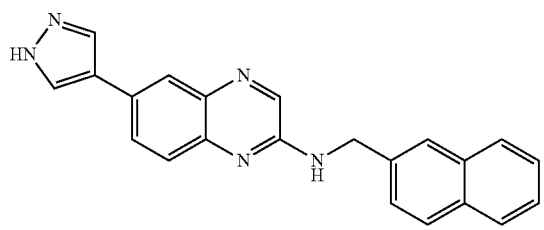 [SMILES: c1ccc2cc(CNc3cnc4cc(-c5cn[nH]c5)ccc4n3)ccc2c1] | Example 53 was prepared by the same method as used for Example 1 except for the following:<br>For step A, Naphthalen-2-yl-methylamine was used instead of benzylamine.<br>C-Naphthalen-2-yl-methylamine was prepared using scheme I. |

C-Naphthalen-2-yl-methylamine

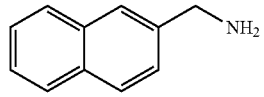 [SMILES: NCc1ccc2ccccc2c1]

The title compound was prepared by the synthetic route shown in Scheme I below.

Scheme I

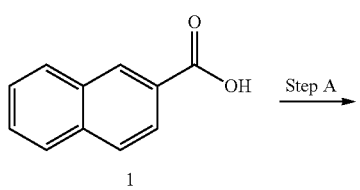

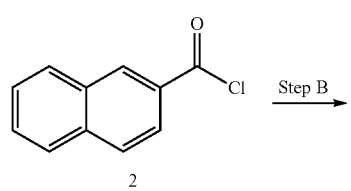

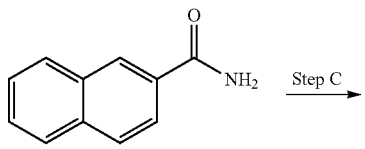

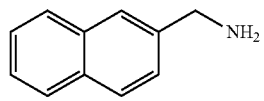

Step A

Naphthalene-2-carbonyl chloride 2-naphthoic acid (2.0 g, 1.0 eq, 11.62 mmol) was dissolved in DCM (30 mL) at room temperature and 2-3 drops of DMF were added. The reaction solution was cooled down to 0-5° C. and slowly oxalyl chloride (2.95 g, 2.0 eq, 23.23 mmol) was added to the reaction mass at 0-5° C. The reaction mixture was stirred for 3-4 hrs at room temperature under nitrogen. After completion of reaction (confirmed by TLC), the reaction mixture was concentrated in vacuo to afford the crude acid chloride which was used directly in the next step.

Step B

Naphthalene-2-carboxylic acid amide

A solution of Naphthalene-2-carbonyl chloride obtained from Step A was dissolved in THF (30 mL) and this was cooled down to 0° C. Ammonia gas was passed for approximately 1.5 hrs through the solution and the reaction was stirred at room temperature under a closed system for 4 hrs. A white solid precipitate was observed in the reaction mixture. The reaction mixture was dissolved in ethyl acetate and washed using water followed by brine solution. The organic layer was separated and dried over sodium sulphate and the volatiles were evaporated off in vacuo to afford the crude product.

The crude product was purified by column chromatography using neutral silica gel of 60-120 mesh size. A gradient of 50-60% ethyl acetate in hexane was used for elution of the title compound (0.8 g).

Step C

C-Naphthalen-2-yl-methylamine

Naphthalene-2-carboxylic acid amide (0.8 g, 1 eq, 4.678 mmol) was dissolved in THF (80 mL) and the solution was cooled down to 0-5° C. A 1.0 M solution of Lithium Aluminium Hydride (LAH) in THF (1.42 g, 8.0 eq, 37.0 mmol) was added drop-wise at 0-5° C. The reaction mixture was stirred at RT overnight. After completion of the reaction (confirmed by TLC), ethyl acetate at 0-5° C. was slowly added to quench the excess LAH in reaction mixture followed by the addition of saturated sodium sulphate solution (2 mL). The reaction mass was filtered through a hy-flow bed and the filtrate was concentrated in vacuo to afford the crude product.

The crude product was purified by column chromatography using neutral silica gel of 60-120 mesh size. A gradient of 3-4% methanol in DCM was used to elute the title compound (0.43 g, 58%).

Examples 40 to 46

By following the methods described above, modified as indicated, the compounds of Examples 40 to 46 were prepared.

40 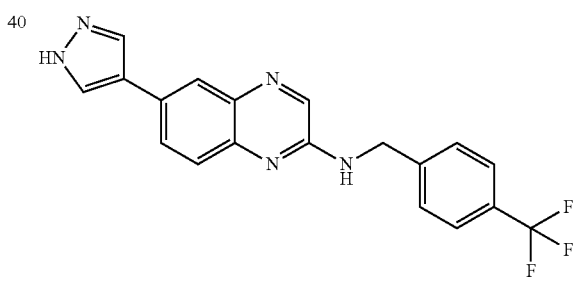

Example 40 was prepared by the same method as used for Example 1 except for the following:
For step A, 4-trifluoromethyl-benzylamine was used instead of benzylamine.

41 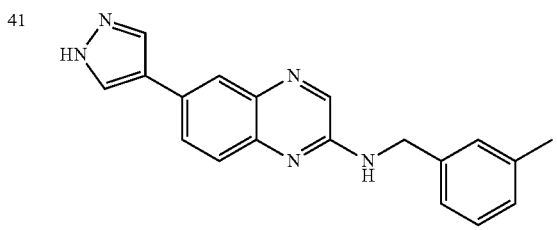

Example 41 was prepared by the same method as used for Example 1 except for the following:
For step A, 3-methyl-benzylamine was used instead of benzylamine.

42 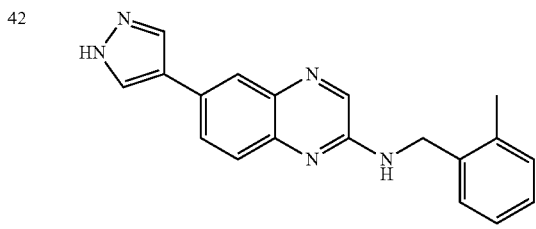

Example 42 was prepared by the same method as used for Example 1 except for the following:
For step A, 2-methyl-benzylamine was used instead of benzylamine.

43 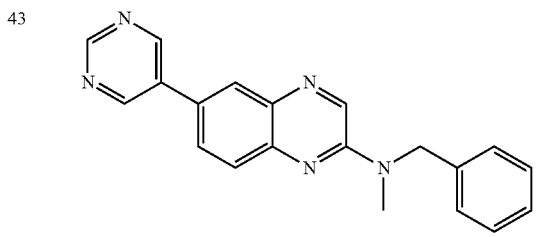

Example 43 was prepared by the same method as used for Example 21 except for the following:
For step A, benzylamine was used instead of 4-Fluoro-benzylamine.
For step C, Pyrimidine, 5-(4,4,5,5-tetramethyl-1,3,2-dioxaborolan-2-yl)- was used instead of 4-(4,4,5,5-Tetramethyl-[1,3,2]dioxaborolan-2-yl)-pyrazole-1-carboxylic acid tert-butyl ester

| | | |
|---|---|---|
| 44 | 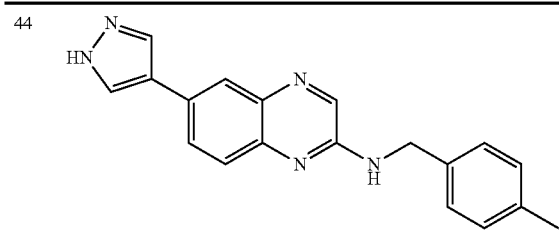 | Example 44 was prepared by the same method as used for Example 1 except for the following: For step A, 4-methyl-benzylamine was used instead of benzylamine. |
| 45 | 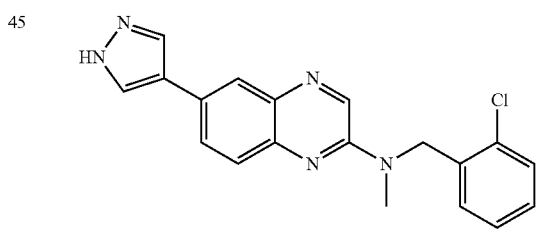 | Example 45 was prepared by the same method as used for Example 21 except for the following: For step A, 2-chloro-benzylamine was used instead of 4-Fluoro-benzylamine. |
| 46 | 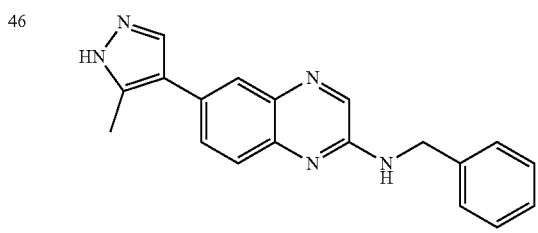 | Example 46 was prepared by the same method as used for Example 1 except for the following: For step B, 5-methyl-4-(4,4,5,5-tetramethyl-[1,3,2]dioxaborolan-2-yl)-1H-pyrazole was used instead of N-Boc-4-pyrazole boronic acid pinacol ester |

Example 47

{(R)-1-[3-(4-Methyl-piperazin-1-yl)-phenyl]-ethyl}-[6-(1H-pyrazol-4-yl)-quinoxalin-2-yl]-amine

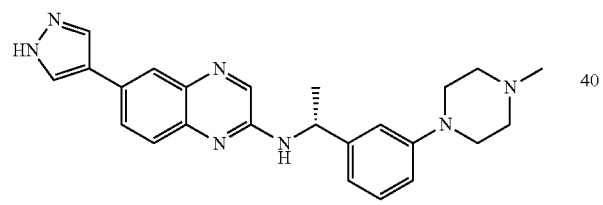

The title compound was prepared by the sequence of reactions shown in Scheme J below.

Scheme J

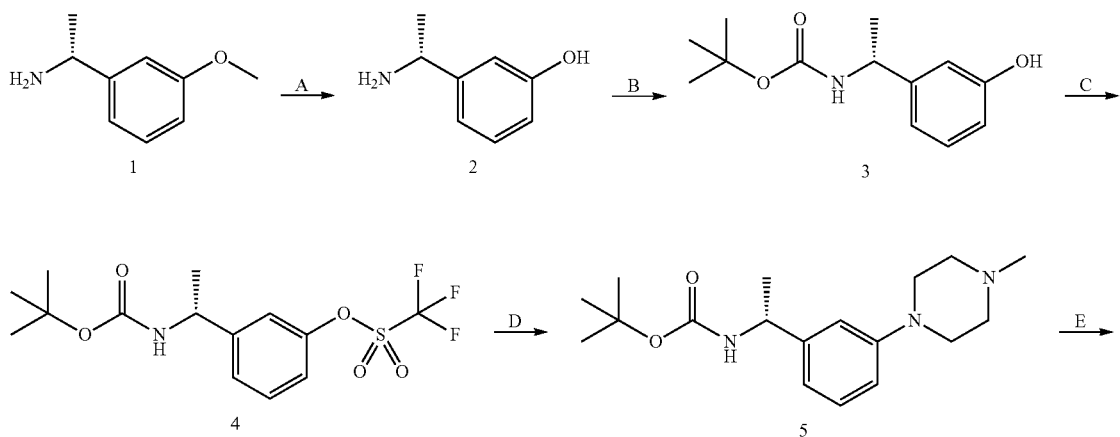

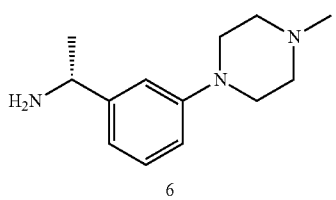
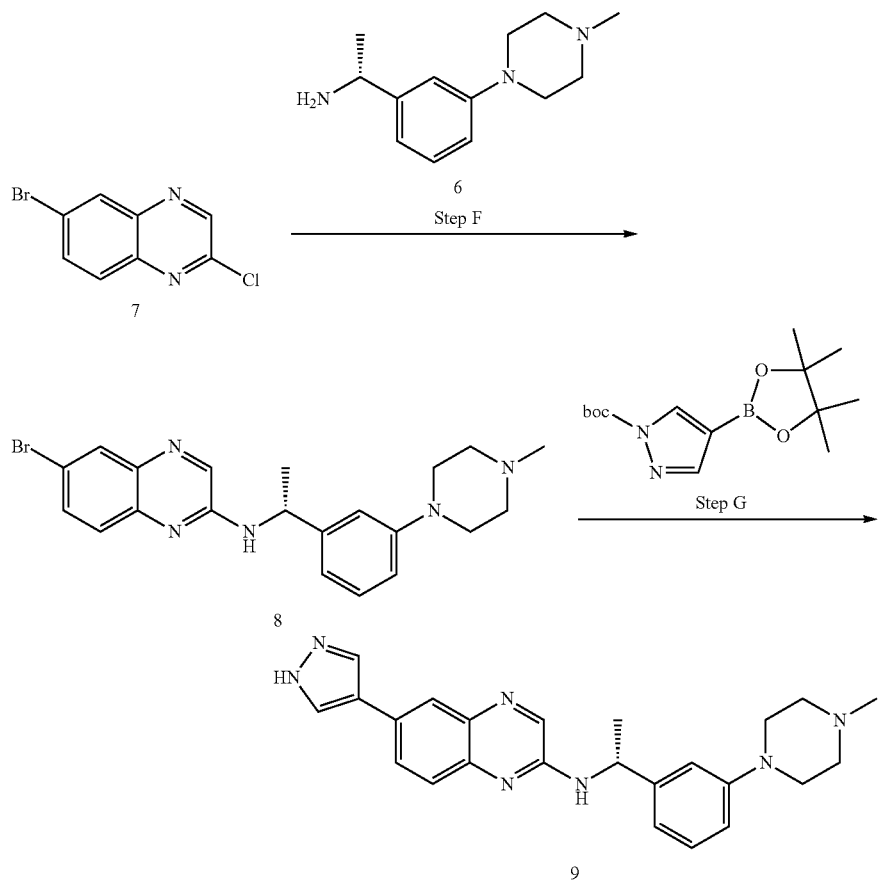

Step A

3-((R)-1-Amino-ethyl)-phenol

To the solution of (R)-1-(3-Methoxy-phenyl)-ethylamine (0.5 g, 3.31 mmol) in DCM (25 mL) at −78° C. was added 1.0M BBr₃ solution in DCM (6.6 mL, 6.62 mmol) dropwise. The solution was warmed to room temperature and the reaction mixture was quenched with methanol (100 mL) and then concentrated in vacuo. This process was repeated until no white fumes were observed upon addition of methanol to afford 3-((R)-1-Amino-ethyl)-phenol as a pale yellow oil (0.51 g) which was used in the next step without further purification.

Step B

[(R)-1-(3-Hydroxy-phenyl)-ethyl]-carbamic acid tert-butyl ester

A solution of 3-((R)-1-Amino-ethyl)-phenol, (0.5 g, 3.60 mmol), di-tert-butyl dicarbonate (0.337 g, 1.55 mmol) and triethyl amine (0.783 mL, 5.6 mmol) in DCM (30 mL) was stirred at room temperature for 30 minutes. After completion of the reaction, the reaction mixture was washed with saturated sodium bicarbonate solution (10 mL) and the aqueous layer was extracted with DCM (2×15 mL). The combined organic layers were diluted further with ethyl acetate (325 mL) and washed with water (100 mL×3) and then brine (100 mL). The organic layer was dried over Na₂SO₄ and concentrated in vacuo to obtain the title compound as a pale yellow solid (2.73 g).

For final purification, column chromatography was used on neutral silica gel employing a gradient of 0-0.5% methanol in DCM to elute the title compound (0.57 g, 66%).

Step C

Trifluoro-methanesulfonic acid 3-((R)-1-tert-butoxy-carbonylamino-ethyl)-phenyl ester To a solution of [(R)-1-(3-Hydroxy-phenyl)-ethyl]-carbamic acid tert-butyl ester (1.2 g, 5.38 mmol) in DCM (20 mL), was added triethylamine (1.4 mL, 10.16 mmol), followed by trifluoromethylsulfonyl anhydride (1.6 g, 5.65 mmol) at 0° C. The solution was stirred at room temperature for 30 minutes, and after completion of reaction, the reaction mixture was quenched with water (10 mL). The aqueous layer was extracted with DCM (2×15 mL), and the combined organic layers were dried over magnesium sulphate and concentrated in vacuo. The crude product was purified by silica gel flash chromatography eluting with 10% ethyl acetate in hexane to afford the title compound (0.34 g, 16%).

Step D

{(R)-1-[3-(4-Methyl-piperazin-1-yl)-phenyl]-ethyl}-carbamic acid tert-butyl ester A mixture of Trifluoro-methanesulfonic acid 3-((R)-1-tert-butoxycarbonylamino-ethyl)-phenyl ester (0.340 g, 0.921 mmol), 1-methylpiperazine (0.37 g, 3.68 mmol), Pd$_2$(dba)$_3$ (0.042 g, 0.046 mmol), 2-(di-tert-butylphosphino)-biphenyl (0.054 g, 0.184 mmol), and potassium phosphate (0.273 g, 1.29 mmol) in 20 mL of 1,4 dioxane was heated at 80° C. in a sealed tube for 12 hours. After completion of the reaction, the reaction mixture was cooled to room temperature and diluted with ethyl acetate (100 mL) and the washed with water (20 mL). The aqueous layer was extracted with ethyl acetate (2×50 mL), and the combined organic layers were dried over magnesium sulfate and concentrated in vacuo to afford the crude title compound.

The crude product was purified by column chromatography using 60-120 mesh silica gel and the compound was eluted by a gradient of 25% ethyl acetate in hexane to afford the title compound (0.6 g, 20%) which was used for next step.

Step E (R)-1-[3-(4-Methyl-piperazin-1-yl)-phenyl]-ethylamine

To a solution of {(R)-1-[3-(4-Methyl-piperazin-1-yl)-phenyl]ethyl}-carbamic acid tert-butyl ester (0.6 g, 1.87 mmol) in 1,4-Dioxane (1.5 mL), was added 4N HCl(aq) (2 mL) at room temperature. The resulting mixture was heated at 50° C. for 5 h. After completion of the reaction, the reaction mixture was concentrated and washed with diethyl ether (5.0 mL) to afford the title compound (0.330 g).

Step F (6-Bromo-quinoxalin-2-yl)-{(R)-1-[3-(4-methyl-piperazin-1-yl)-phenyl]-ethyl}-amine 6-bromo-2-chloroquinoxaline (0.365 g 1.5 mmol) was dissolved in DMSO (10 mL) at room temperature and (R)-1-[3-(4-Methyl-piperazin-1-yl)-phenyl]-ethylamine (0.33 g, 1.5 mmol) and triethylamine (0.626 mL, 4.50 mmol) were added to the solution. The reaction mixture was stirred at room temperature overnight. After completion of the reaction, water (100 mL) was added and the product was extracted with ethyl acetate (3×50 mL). The organic layer was washed with water (10 mL) followed by brine solution (10 mL) and dried over Na$_2$SO$_4$. The organic layer was concentrated in vacuo to afford the crude product.

The product was purified by column chromatography using neutral silica gel of 60-120 mesh size and was eluted by a gradient of 5-15% ethyl acetate in hexane to afford the title compound as a solid (0.250 g, 47%).

Step G 4-(2-{(R)-1-[3-(4-Methyl-piperazin-1-yl)-phenyl]-ethylamino}-quinoxalin-6-yl)-pyrazole-1-carboxylic acid tert-butyl ester A mixture of (6-Bromo-quinoxalin-2-yl)-{(R)-1-[3-(4-methyl-piperazin-1-yl)-phenyl]ethyl}-amine (0.250 g, 1 eq., 0.588 mmol), 1-Boc-4-pyrazole boronic acid pinacol ester (0.190 g, 1.1 eq., 0.647 mmol), caesium carbonate (0.764 g, 4.0 eq., 2.35 mmol) and potassium iodide (0.010 g, 0.1 eq., 0.00588 mmol) in 1,4-dioxane (15 mL) was degassed at RT under vacuum and placed under an atmosphere of nitrogen. The process was repeated twice and Fu's catalyst (Bis(tri-tert-butylphosphine)palladium(0)) (0.015 g, 0.05 eq., 0.029 mmol) was added at room temperature. The reaction mixture was heated at 105° C. in a microwave reactor for 180 minutes. After completion of the reaction (confirmed by TLC), the organic mixture was diluted with ethyl acetate (325 mL) and washed with water (100 mL×3) and brine (100 mL). The organic layer was dried and concentrated under vacuum to give a crude residue.

The product was purified by column chromatography using neutral silica gel of 60-120 mesh size. Methanol (1-3%) was used as a gradient in DCM for elution of the title compound (0.035 g, 14%).

Example 48

Methyl-[3-(4-methyl-piperazin-1-yl)-benzyl]-[6-(1H-pyrazol-4-yl)-quinoxalin-2-yl]-amine

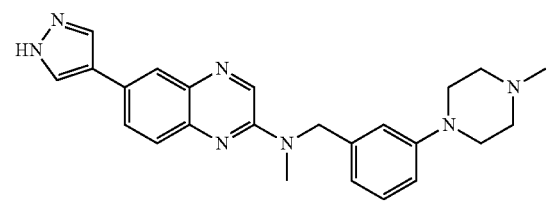 [SMILES: CN1CCN(c2cccc(CN(C)c3cnc4cc(-c5cn[nH]c5)ccc4n3)c2)CC1]

The title compound was prepared by the synthetic route shown in Scheme A below.

Scheme K

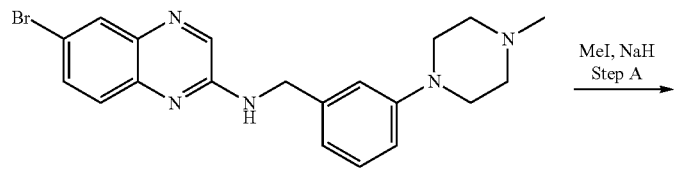

1

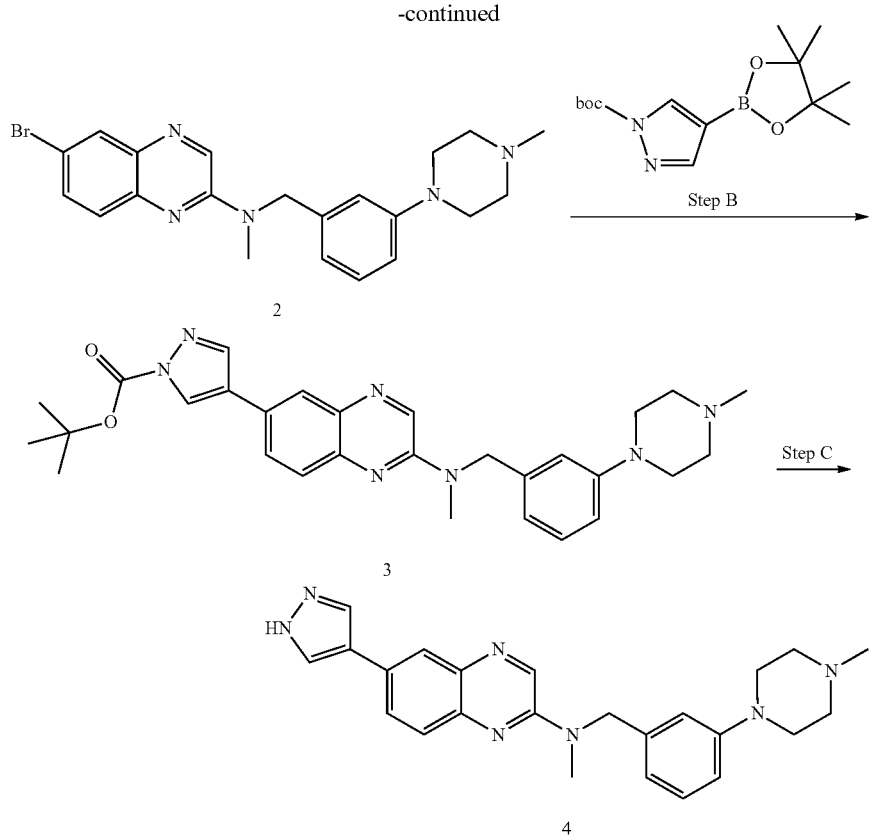

Step A

(6-Bromo-quinoxalin-2-yl)-methyl-[3-(4-methyl-piperazin-1-yl)-benzyl]-amine

Using (6-Bromo-quinoxalin-2-yl)-[3-(4-methyl-piperazin-1-yl)-benzyl]-amine (0.4 g, 0.97 mmol) obtained from the preparation of example 6, the title compound was prepared (0.35 g, 84%) using the method detailed in step B of example 21.

Step B

4-(2-{Methyl-[3-(4-methyl-piperazin-1-yl)-benzyl]-amino}-quinoxalin-6-yl)-pyrazole-1-carboxylic acid tert-butyl ester

Using (6-Bromo-quinoxalin-2-yl)-methyl-[3-(4-methyl-piperazin-1-yl)-benzyl]-amine (0.3 g, 0.704 mmol) as starting material and employing the method detailed in step B of example 1, the title compound was prepared (0.110 g, 30%).

Step C

Methyl-[3-(4-methyl-piperazin-1-yl)-benzyl]-[6-(1H-pyrazol-4-yl)-quinoxalin-2-yl]-amine

To a solution of 4-(2-{Methyl-[3-(4-methyl-piperazin-1-yl)-benzyl]-amino}-quinoxalin-6-yl)-pyrazole-1-carboxylic acid tert-butyl ester (0.110 g, 0.000214 mmol) in 1,4-dioxane (1.5 mL), was added HCl in dioxane (1.0 ml) at room temperature. The mixture was stirred for 1 hour. After completion of the reaction, the reaction mixture was concentrated and washed with diethyl ether (5.0 mL) to afford the crude compound (0.075 g). The compound was basified by ammonia in THF and then further purified by preparative TLC to afford the title compound (0.050 g, 54%). The mobile phase used for the Preparative TLC was DCM:Methanol (9:1).

Example 49

[(R)-1-(3-Fluoro-phenyl)-ethyl]-[6-(1H-pyrazol-4-yl)-quinoxalin-2-yl]-amine hydrochloride

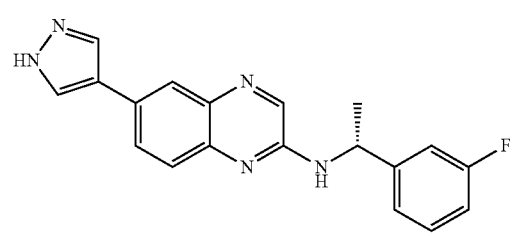 [SMILES: C[C@@H](Nc1cnc2cc(-c3cn[nH]c3)ccc2n1)c1cccc(F)c1]

The title compound was prepared by the synthetic route shown in Scheme L below.

Scheme L

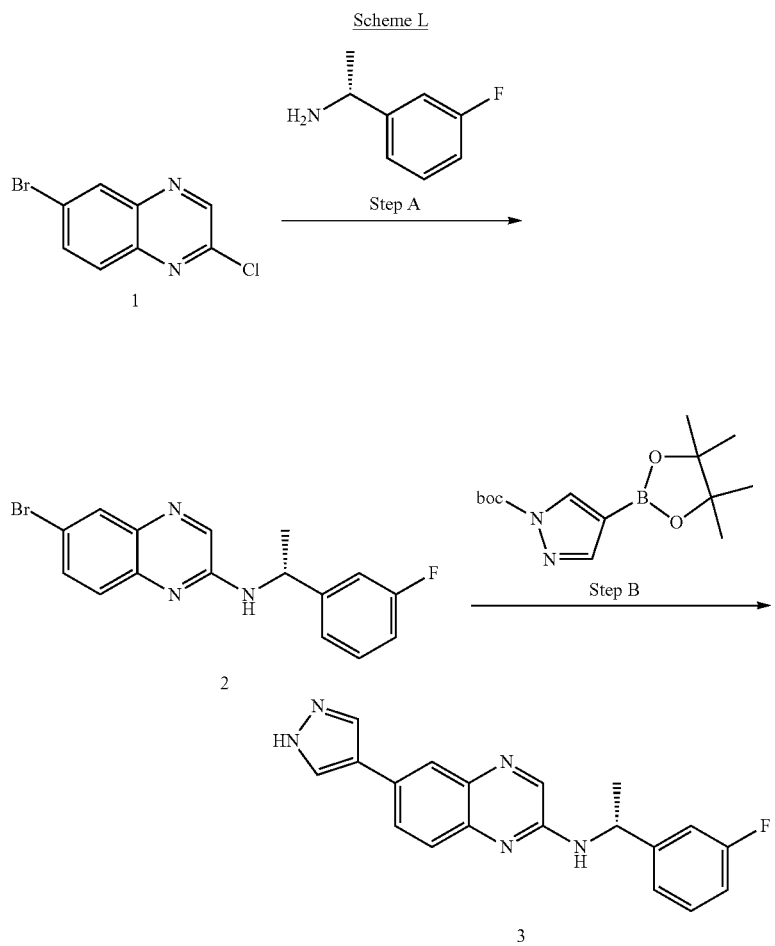

Step A (6-Bromo-quinoxalin-2-yl)-[(R)-1-(3-fluoro-phenyl)-ethyl]-amine 6-bromo, 2-chloroquinoxaline (0.700 g, 2.8 mmol) and Triethylamine (0.87 g, 8.6 mmol) were dissolved in DMSO (15 mL) at room temperature and (R)-1-(3-Fluoro-phenyl)-ethylamine hydrochloride (0.400 g, 2.8 mmol) was added. The reaction mixture was stirred at RT for 16 hours. After completion of reaction (confirmed by TLC), water (100 mL) was added to the reaction mixture and it was extracted with ethyl acetate (50 mL×3). The organic layer was washed with water (15 mL), brine (15 mL), and was then dried over Na$_2$SO$_4$. The organic layer was concentrated in vacuo to afford the crude product.

The crude product was adsorbed on silica gel and was purified by column chromatography using neutral silica gel of 60-120 mesh size. Methanol (1-1.5%) was used as a gradient in DCM for elution of the title compound as a solid (0.35 g, 36%).

Step B

[(R)-1-(3-Fluoro-phenyl)-ethyl]-[6-(1H-pyrazol-4-yl)-quinoxalin-2-yl]-amine hydrochloride (6-Bromo-quinoxalin-2-yl)-[(R)-1-(3-fluoro-phenyl) ethyl]-amine (0.15 g, 0.43 mmol), N-Boc-4-pyrazole boronic acid pinacol ester (0.14 g, 0.47 mmol), caesium carbonate (0.56 g, 1.73 mmol) and potassium iodide (0.007 g, 0.043) were added to 1,4-dioxane (5 mL). The reaction mixture was degassed at RT under vacuum and placed under an atmosphere of nitrogen. The process was repeated twice and Fu's catalyst (Bis(tri-tert-butylphosphine)palladium(0)) (0.011 g 0.021 mmol) was added at RT. The reaction mixture was heated at 110° C. in a microwave reactor for 180 minutes. The organic mixture was diluted with ethyl acetate (150 mL) and was washed with water (15 mL×2) and brine (15 mL). The organic solvent was evaporated under vacuum to afford the crude product.

The crude product was purified by column chromatography on neutral silica gel of 60-120 mesh size. A gradient of 2-3% methanol in DCM was used to elute the title compound (0.06 g). To further purify, formation of the hydrochloride salt was carried out by treatment with saturated HCl in IPA, followed by trituration in acetone to afford the title compound (0.015 g, 9%).

Example 50
[(R)-1-(3-Methoxy-phenyl)-ethyl]-[6-(1H-pyrazol-4-yl)-quinoxalin-2-yl]-amine hydrochloride
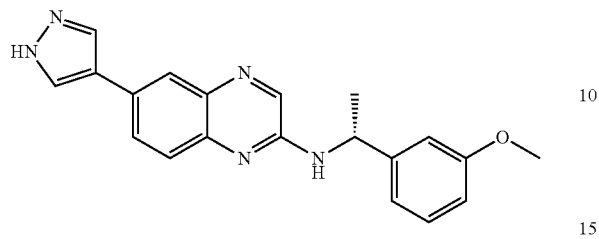
The title compound was prepared by the synthetic route shown in Scheme M below.
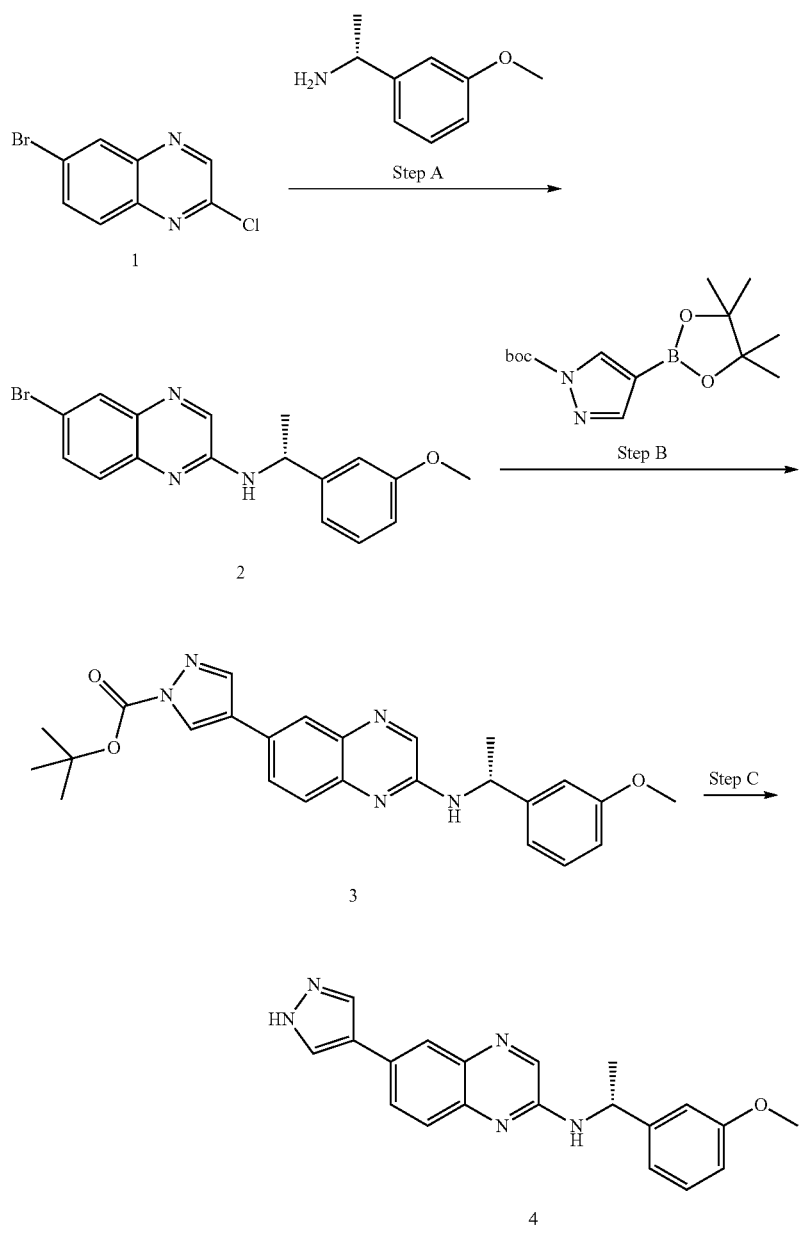

Step A

(6-Bromo-quinoxalin-2-yl)-[(R)-1-(3-methoxy-phenyl)-ethyl]-amine 6-bromo, 2-chloroquinoxaline (0.300 g, 1.2 mmol) was dissolved in DMSO (15 mL) at room temperature and (R)-1-(3-Methoxy-phenyl)-ethylamine (0.85 g, 6.1 mmol) was added. The reaction mixture was stirred at RT for 16 hours. After completion of the reaction (confirmed by TLC), water (100 mL) was added to the reaction mixture and it was extracted with ethyl acetate (50 mL×3). The organic layer was washed with water (15 mL), brine (15 mL), and then dried over $Na_2SO_4$. The organic layer was concentrated in vacuo to afford crude product.

The crude product was adsorbed on silica gel and purified by column chromatography using neutral silica gel of 60-120 mesh size. A gradient of 1-1.5% methanol in DCM was used to elute the title compound as a solid (0.35 g, 82%).

Step B

4-{2-[(R)-1-(3-Methoxy-phenyl)-ethylamino]-quinoxalin-6-yl}-pyrazole-1-carboxylic acid tert-butyl ester (6-Bromo-quinoxalin-2-yl)-[(R)-1-(3-methoxy-phenyl)-ethyl]-amine (0.3 g, 0.83 mmol), N-Boc-4-pyrazole boronic acid pinacol ester (0.27 g, 0.92 mmol), caesium carbonate (1.08 g, 3.34 mmol) and potassium iodide (0.014 g, 0.083) were dissolved in 1,4-dioxane (15 mL). The reaction mixture was degassed at RT under vacuum and placed under an atmosphere of nitrogen. The process was repeated twice and Fu's catalyst (Bis(tri-tert-butylphosphine)palladium(0)) (0.021 g, 0.041 mmol) was added at RT. The reaction mixture was heated at 110° C. in a microwave reactor for 180 minutes. The organic mixture was diluted with ethyl acetate (150 mL), washed with water (15 mL×2) and brine (15 mL) and was then dried over $Na_2SO_4$. The organic volatiles were evaporated in vacuo to afford crude product.

The crude product was purified by column chromatography on neutral silica gel of 60-120 mesh size. A gradient of 2-3% methanol in DCM was used to elute a mixture of the title compound and also [(R)-1-(3-Methoxy-phenyl)-ethyl]-[6-(1H-pyrazol-4-yl)-quinoxalin-2-yl]-amine (0.12 g). The mixture was carried through to step C.

Step C

[(R)-1-(3-Methoxy-phenyl)-ethyl]-[6-(1H-pyrazol-4-yl)-quinoxalin-2-yl]-amine hydrochloride To a mixture of 4-{2-[(R)-1-(3-Methoxy-phenyl)-ethylamino]-quinoxalin-6-yl}-pyrazole-1-carboxylic acid tert-butyl ester and [(R)-1-(3-Methoxy-phenyl)-ethyl]-[6-(1H-pyrazol-4-yl)-quinoxalin-2-yl]-amine (0.12 g of mixture) in 1,4-dioxane was added 4M HCl in 1,4-dioxane at room temperature. The mixture was stirred for 1 hour. After completion of the reaction, the reaction mixture was concentrated in vacuo and was basified using ammonia in THF. The free base was treated with saturated HCl in IPA, followed by trituration in acetone to afford the title compound as the HCl salt (0.020 g).

Examples 51 to 54

By following the methods described above, modified as indicated, the compounds of Examples 51 to 54 were prepared.

| 51 | 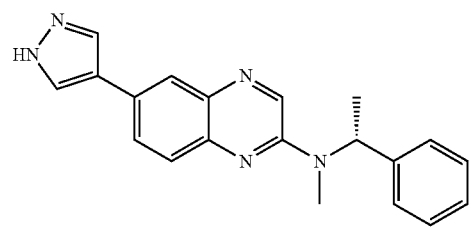 [SMILES: C[C@H](c1ccccc1)N(C)c1cnc2cc(-c3cn[nH]c3)ccc2n1] | Example 51 was prepared by the same method as used for Example 21 except for the following: For step A, (R)-1-Phenyl-ethylamine was used instead of 4-Fluoro-benzylamine. |
| --- | --- | --- |
| 52 | 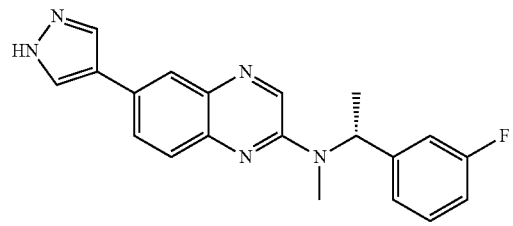 [SMILES: C[C@H](c1cccc(F)c1)N(C)c1cnc2cc(-c3cn[nH]c3)ccc2n1] | Example 52 was prepared by the same method as used for Example 21 except for the following: For step A, (R)-1-(3-Fluoro-phenyl)-ethylamine hydrochloride was used instead of 4-Fluoro-benzylamine. |
| 53 | 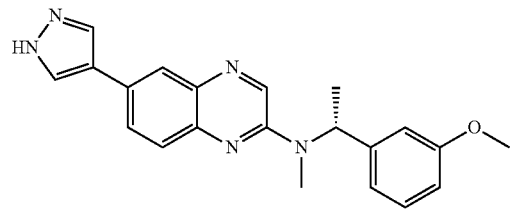 | Example 53 was prepared by the same method as used for Example 21 except for the following: For step A, (R)-1-(3-Methoxy-phenyl)-ethylamine was used instead of 4-Fluoro-benzylamine. |

| | |
|---|---|
| 54 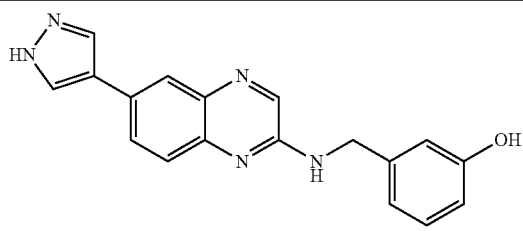 | Example 54 was prepared by the same method as used for Example 1 except for the following: For step A, 3-Aminomethyl-phenol was used instead of benzylamine. |
Example 55
[(R)-1-(3-Methoxy-phenyl)-ethyl]-[6-(1H-pyrazol-4-yl)-quinoxalin-2-yl]-amine hydrochloride
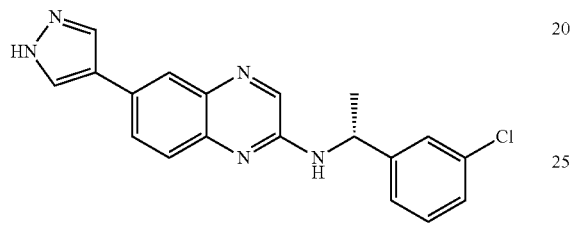
The title compound was prepared by the synthetic route shown in Scheme M below.
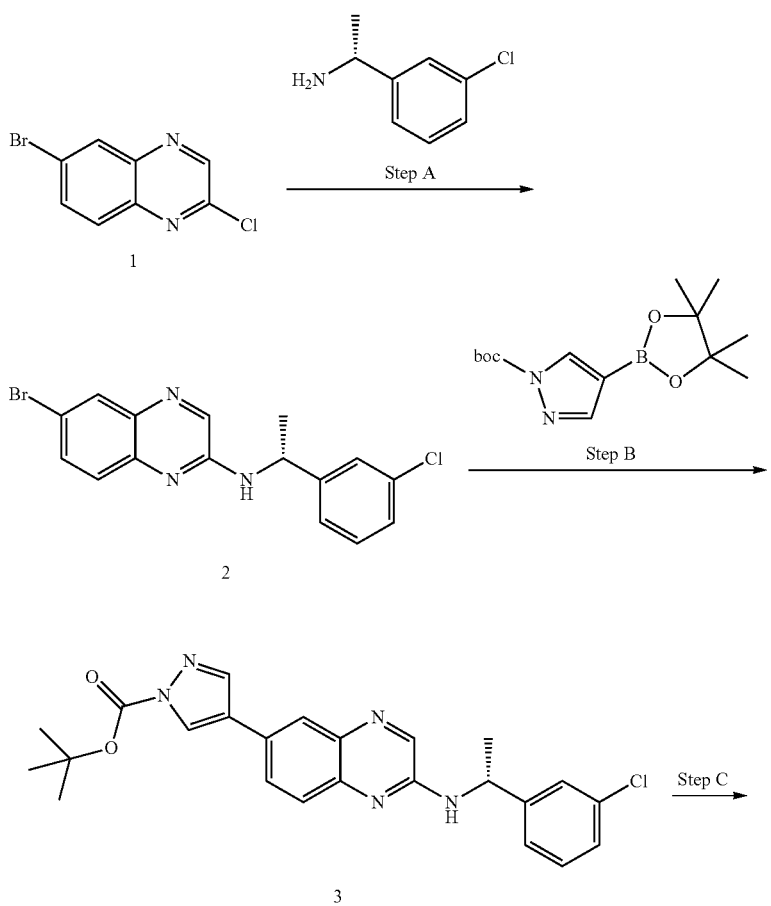

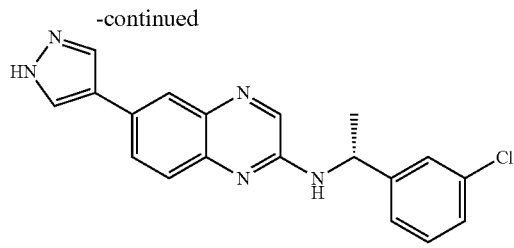

4

Step A (6-Bromo-quinoxalin-2-yl)-[(R)-1-(3-chloro-phenyl)-ethyl]-amine 6-bromo, 2-chloroquinoxaline (0.35 g 1.4 mmol) was dissolved in DMSO (12 mL) at room temperature and (R)-1-(3-Chloro-phenyl)-ethylamine (0.44 g, 2.8 mmol) was added. The reaction mixture was stirred at RT for 16 hours. After completion of the reaction (confirmed by TLC), water (100 mL) was added to the reaction mixture and it was extracted with ethyl acetate (50 mL×3). The organic layer was washed with water (15 mL), brine (15 mL), and then dried over $Na_2SO_4$. The organic layer was concentrated in vacuo to afford the crude product.

The crude product was adsorbed on 60-120 mesh silica gel and purified by column chromatography using neutral silica gel of 60-120 mesh size. A gradient of 0.5% methanol in DCM was used for elution of the title compound (0.380 g, 72%).

Step B

4-{2-[(R)-1-(3-Chloro-phenyl)-ethylamino]-quinoxalin-6-yl}-pyrazole-1-carboxylic acid tert-butyl ester A mixture of (6-Bromo-quinoxalin-2-yl)-[(R)-1-(3-chloro-phenyl)-ethyl]-amine (0.38 g, 1.0 mmol), N-Boc-4-pyrazole boronic acid pinacol ester (0.37 g, 1.2 mmol), caesium carbonate (1.36 g, 4.1 mmol) and potassium iodide (0.017 g, 0.1) in 1,4-dioxane (20 mL) was degassed at RT under vacuum and placed under an atmosphere of nitrogen. The process was repeated twice and Fu's catalyst (Bis(tri-tert-butylphosphine)palladium(0)) (0.053 g, 0.1 mmol) was added at RT. The reaction mixture was heated at 110° C. in a microwave reactor for 180 minutes. The organic mixture was diluted with ethyl acetate (150 mL) and washed with water (20 mL×2) and brine (20 mL). The organic solvent was evaporated in vacuo to afford the crude product.

The crude product was purified by column chromatography using neutral silica gel of 60-120 mesh size. A gradient of 3-4% methanol in DCM was used to elute the title compound (0.100 g, 19%).

Step C

[(R)-1-(3-Chloro-phenyl)-ethyl]-[6-(1H-pyrazol-4-yl)-quinoxalin-2-yl]-amine hydrochloride To an ice cold solution of 4-{2-[(R)-1-(3-Chloro-phenyl)-ethylamino]-quinoxalin-6-yl}-pyrazole-1-carboxylic acid tert-butyl ester (0.1 g,) in 1,4-dioxane (3 mL) was added 14% HCl in dioxane (2 mL). The resulting mixture was stirred at RT for 2 hours. After completion of the reaction, the volatiles were evaporated off completely and the solid was triturated with acetone to afford the title compound as the HCl salt (0.017 g, 20%).

Examples 56 to 60

By following the methods described above, modified as indicated, the compounds of Examples 56 to 60 were prepared.

56 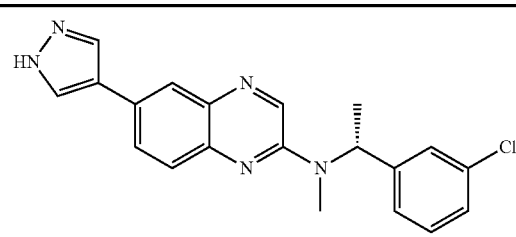

Example 56 was prepared by the same method as used for Example 21 except for the following:
For step A, (R)-1-(3-Chloro-phenyl)-ethylamine was used instead of 4-Fluoro-benzylamine.

57 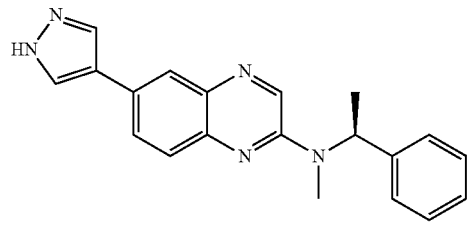 [SMILES: C[C@@H](c1ccccc1)N(C)c1cnc2cc(-c3cn[nH]c3)ccc2n1]

Example 57 was prepared by the same method as used for Example 21 except for the following:
For step A, (S)-1-Phenyl-ethylamine was used instead of 4-Fluoro-benzylamine.

| 58 | 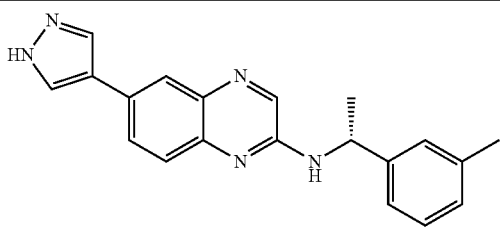 | Example 58 was prepared by the same method as used for Example 1 except for the following: For step A, (R)-1-m-Tolyl-ethylamine was used instead of benzylamine. |
| 59 | 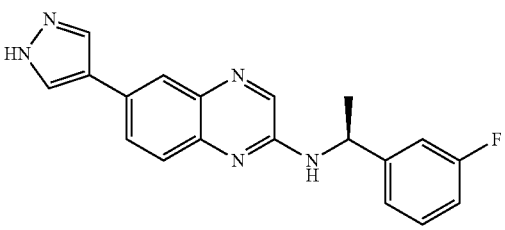 [SMILES: C[C@H](Nc1cnc2cc(-c3cn[nH]c3)ccc2n1)c1cccc(F)c1] | Example 59 was prepared by the same method as used for Example 1 except for the following: For step A, (S)-1-(3-Fluoro-phenyl)-ethylamine was used instead of benzylamine. |
| 60 | 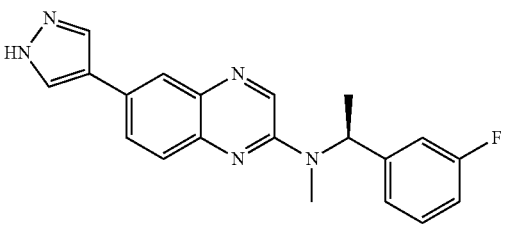 [SMILES: C[C@@H](c1cccc(F)c1)N(C)c1cnc2cc(-c3cn[nH]c3)ccc2n1] | Example 60 was prepared by the same method as used for Example 21 except for the following: For step A, (S)-1-(3-Fluoro-phenyl)-ethylamine was used instead of 4-Fluoro-benzylamine. |

Characterising and Analytical Data

The characterising and analytical data for the compounds of Examples 1 to 60 are set out in the table below.

| Ex. No. | Compound Name | Mol. Wt. | NMR (d6-DMSO) | LCMS, conditions | LCMS rt (min) | Mass ion (MH+) |
|---|---|---|---|---|---|---|
| 1 | Benzyl-[6-(1H-pyrazol-4-yl)-quinoxalin-2-yl]-amine | 301.35 | $^1$H NMR (MeOD) 8.26 (s, 1H, —ArH), 8.10-7.98 (brs, d, 2H, —ArH), 7.98 (d, 1H, —ArH), 7.941-7.946 (dd, 1H, —ArH), 7.81-7.84 (dd, 1H, —ArH), 7.63-7.64 (d, 1H, —ArH), 7.41-7.43 (d, 2H, —ArH), 7.31-7.31 (t, 2H, —ArH), 7.23-7.27 (t, 1H, —ArH), 4.69 (s, 2H, —CH$_2$—), and 4.55-4.66 (s, 1H, —NH—). | A | 4.994 | 302.0 |
| 2 | Benzyl-methyl-[6-(1H-pyrazol-4-yl)-quinoxalin-2-yl]-amine hydrochloride | 315.38 | $^1$H NMR (DMSO-d6) 8.65 (s, 1H, —ArH), 8.3 (s, 1H, —ArH), 8.01-8.02 (d, 2H, —ArH), 7.85-7.88 (dd, 1H, —ArH), 7.55-7.58 (d, 1H, —ArH), 7.22-7.34 (m, 5H, —ArH), 4.95 (s, 2H, —CH$_2$), and 3.22 (s, 3H, —CH$_3$) | B | 10.830 | 316.0 |
| 3 | 2-{Benzyl-[6-(1H-pyrazol-4-yl)-quinoxalin-2-yl]-amino}-ethanol | 345.41 | $^1$H NMR (DMSO-d6) 12.9 (s, 1H), 8.63 (s, 1H), 8.31 (br s, 1H), 8.12-7.95 (m, 2H), 7.85 (d, 1H), 7.52 (d, 1H), 7.35-7.20 (m, 4H), 4.99 (s, 2H), 4.87 (t, 1H), 3.76 (t, 2H), 3.63 (t, 2H) | E | 7.716 | 346 |
| 4 | (4-Morpholin-4-yl-benzyl)-[6-(1H-pyrazol-4-yl)-quinoxalin-2-yl]-amine | 386.46 | $^1$H NMR (DMSO-d$_6$) 12.94 (s, 1H), 8.30 (s, 1H), 8.27 (br s, 1H), 7.98 (1H, br s), 7.95 (s, 1H), 7.87 (t, 1H), 7.80 (dd, 1H), 7.50 (d, 1H), 7.24 (d, 2H), 6.90 (d, 2H), 4.46 (d, 2H), 3.69 (t, 4H), 3.03 (t, 4H) | | | 387.2 |

-continued

| Ex. No. | Compound Name | Mol. Wt. | NMR (d6-DMSO) | LCMS, conditions | LCMS rt (min) | Mass ion (MH+) |
|---|---|---|---|---|---|---|
| 5 | [4-(4-Methyl-piperazin-1-yl)-benzyl]-[6-(1H-pyrazol-4-yl)-quinoxalin-2-yl]-amine | 399.50 | $^1$H NMR (DMSO-d$_6$) 12.93 (br s, 1H), 8.29 (s, 1H), 8.26 (br s, 1H), 7.98 (br s, 1H), 7.93 (s, 1H), 7.85 (br t, 1H), 7.80 (d, 1H), 7.50 (d, 1H), 7.23 (d, 2H), 6.97 (d, 2H), 4.46 (d, 2H), 3.11-2.98 (br m, 4H), 2.42-2.33 (br m, 4H), 2.17 (s, 3H) | | | 400.2 |
| 6 | [3-(4-Methyl-piperazin-1-yl)-benzyl]-[6-(1H-pyrazol-4-yl)-quinoxalin-2-yl]-amine hydrochloride | 399.50 | $^1$H NMR (DMSO-d$_6$) 10.43-10.30 (br s, 1H), 8.42 (s, 1H), 8.16 (s, 2H), 8.01 (s, 1H), 7.85 (d, 1H), 7.62 (br d, 1H), 7.23 (t, 1H), 7.08 (s, 1H), 6.92 (d, 2H), 4.62 (br s, 2H), 3.80 (d, 2H), 3.18-2.96 (m, 6H), 2.79 (d, 3H) | | 6.134 | 400 |
| 7 | (3-Morpholin-4-yl-benzyl)-[6-(1H-pyrazol-4-yl)-quinoxalin-2-yl]-amine hydrochloride | 386.46 | $^1$H NMR (DMSO-d$_6$) 8.98 (s, 2H, —HCl•N<u>H</u>), 8.48 (s, 1H, —Ar<u>H</u>), 8.19 (s, 2H, —Py<u>H</u>), 8.06 (s, 1H, -qui<u>H</u>), 7.91-7.89 (d, 1H, -qui<u>H</u>), 7.70-7.68 (d, 1H, -qui<u>H</u>), 7.26-7.22 (t, 1H, -qui<u>H</u>), 7.10 (s, 1H, -qui<u>H</u>), 6.94-6.91 (t, 2H, -qui<u>H</u>), 4.63 (s, 2H, —NH—C<u>H$_2$</u>), 3.74-3.72 (t, 4H, —C<u>H$_2$</u>), 3.14-3.12 (t, 4H, —C<u>H$_2$</u>). | | | 387.1 |
| 8 | (4-Chloro-benzyl)-[6-(1H-pyrazol-4-yl)-quinoxalin-2-yl]-amine | 335.80 | $^1$H NMR (DMSO-d6) 12.95 (br s, 1H), 8.33 (s, 1H), 8.31-8.12 (br s, 2H), 8.07 (t, 1H), 7.97 (d, 1H), 7.81 (dd, 1H), 7.50 (d, 1H), 7.45-7.37 (m, 4H), 4.60 (d, 2H). | C | 7.855 | 336 |
| 9 | (3-Chloro-benzyl)-[6-(1H-pyrazol-4-yl)-quinoxalin-2-yl]-amine | 335.80 | $^1$H NMR (DMSO-d6) 12.96 (s, 1H, —PyN<u>H</u>), 8.40 (s, 1H, -quiN<u>H</u>), 8.34 (s, 2H, —py<u>H</u>), 7.98 (s, 1H, -qui<u>H</u>), 7.82-7.80 (d, 1H, -qui<u>H</u>), 7.54-7.51 (d, 1H, —Ar<u>H</u>), 7.45 (s, 1H, —Ar<u>H</u>), 7.36-7.29 (m, 3H, —Ar<u>H</u>), and 4.6 (s, 2H, —C<u>H$_2$</u>—NH). | | | 336.0 |
| 10 | (2-Chloro-benzyl)-[6-(1H-pyrazol-4-yl)-quinoxalin-2-yl]-amine | 335.80 | $^1$H NMR (DMSO-d$_6$) 12.94 (s, 1H, —<u>H</u>N—Py), 8.39 (s, 1H, -qui<u>H</u>), 8.14 (s, 2H, —py<u>H</u>), 8.05 (s, 1H, —N<u>H</u>), 7.98 (s, 1H, -qui<u>H</u>), 7.82-7.79 (dd, 1H, -qui<u>H</u>), 7.51 (s, 1H, -qui<u>H</u>), 7.49-7.45 (m, 2H, —Ar<u>H</u>), 7.30-7.28 (m, 2H, —Ar<u>H</u>), and 4.68 (s, 2H, —C<u>H$_2$</u>—NH), | | | 336.9 |
| 11 | (4-Fluoro-benzyl)-[6-(1H-pyrazol-4-yl)-quinoxalin-2-yl]-amine hydrochloride | 319.34 | $^1$H NMR (DMSO-d$_6$) 9.21-8.75 (br s, 1H), 8.48 (s, 1H), 8.20 (s, 2H), 8.06 (s, 1H), 7.90 (d, 1H), 7.72 (d, 1H), 7.52-7.44 (m, 2H), 7.18 (t, 2H), 4.69 (br s, 2H). | | | 320.0 |
| 12 | (3-Fluoro-benzyl)-[6-(1H-pyrazol-4-yl)-quinoxalin-2-yl]-amine hydrochloride | 319.34 | $^1$H NMR (DMSO-d6) 8.56 (s, 1H, —<u>H</u>Cl), 8.42 (s, 1H, —Ar<u>H</u>), 8.17 (s, 2H, —Ar<u>H</u>), 8.02 (s, 1H, —Ar<u>H</u>), 7.87-7.84 (d, 1H, —Ar<u>H</u>), 7.60-7.58 (d, 1H, —Ar<u>H</u>), 7.41-7.35 (q, 1H, —Ar<u>H</u>), 7.28-7.24 (d, 2H, —Ar<u>H</u>), 7.11-7.07 (t, 1H, —Ar<u>H</u>), and 4.68 (s, 2H, —C<u>H$_2$</u>—NH), | | | 319.9 |
| 13 | (2-Fluoro-benzyl)-[6-(1H-pyrazol-4-yl)-quinoxalin-2-yl]-amine hydrochloride | 319.34 | $^1$H NMR (DMSO-d6) 8.59 (s, 1H, —<u>H</u>Cl), 8.43 (s, 1H, —Ar<u>H</u>), 8.19 (s, 2H, —Ar<u>H</u>), 8.03 (s, 1H, —Ar<u>H</u>), 7.88-7.86 (d, 1H, —Ar<u>H</u>), 7.63- | D | 5.677 | 320 |

| Ex. No. | Compound Name | Mol. Wt. | NMR (d6-DMSO) | LCMS, conditions | LCMS rt (min) | Mass ion (MH+) |
|---|---|---|---|---|---|---|
| | | | 7.61 (d, 1H, —ArH), 7.52-7.48 (t, 1H, —ArH), 7.36-7.19 (m, 3H, —ArH), and 4.70 (s, 2H, —CH$_2$—NH). | | | |
| 14 | [6-(1H-Pyrazol-4-yl)-quinoxalin-2-yl]-pyridin-4-ylmethyl-amine hydrochloride | 302.34 | $^1$H NMR (MeOD) 8.80 (d, 2H), 8.52 (s, 1H), 8.36 (s, 2H), 8.15 (d, 2H), 8.11 (d, 1H), 7.90 (dd, 1H), 7.60 (d, 1H), 5.08 (s, 2H) | H | 5.485 | 303 |
| 15 | [6-(1H-Pyrazol-4-yl)-quinoxalin-2-yl]-pyridin-3-ylmethyl-amine hydrochloride | 302.34 | $^1$H NMR (DMSO-d$_6$) 8.97 (s, 1H, —ArH), 8.80-8.79 (d, 1H, —ArH), 8.59-8.57 (d, 2H, —AriH, —NH), 8.43 (s, 1H, —ArH), 8.17 (s, 2H, —ArH), 8.02-7.98 (m, 2H, —ArH), 7.86-7.83 (d, 1H, —ArH), 7.55-7.53 (d, 1H, —ArH), 4.83 (s, 2H, —CH$_2$). | D | 4.204 | 302.9 |
| 16 | [6-(1H-Pyrazol-4-yl)-quinoxalin-2-yl]-pyridin-2-ylmethyl-amine hydrochloride | 302.34 | $^1$H NMR (MeOD) 8.73 (d, 1H), 8.55 (t, 1H), 8.49 (s, 1H), 8.26 (s, 2H), 8.14 (d, 1H), 8.07 (d, 1H), 7.93 (t, 1H), 7.87 (dd, 1H), 7.55 (d, 1H), 5.06 (s, 2H). | E | 5.682 | 303 |
| 17 | (4-Methoxy-benzyl)-[6-(1H-pyrazol-4-yl)-quinoxalin-2-yl]-amine | 331.38 | $^1$H NMR (DMSO-d6) 12.94 (s, 1H, —NH), 8.31 (s, 1H, —ArNH), 8.27 (s, 1H, —ArH), 8.00 (s, 1H, —ArH), 7.96-7.95 (d, 1H, —ArH), 7.94-7.91 (t, 1H, —ArH), 7.82-7.81 (dd, 1H, —ArH), 7.52-7.50 (d, 1H, —ArH), 7.31-7.33 (dd, 2H, —ArH), 6.9-6.88 (dd, 2H, ArH) 4.50-4.52 (d, 2H, —CH), 4.43 (s, 1H, —NH) and 3.70 (s, 3H, —CH$_2$) | D | 5.425 | 332.05 |
| 18 | (3-Methoxy-benzyl)-[6-(1H-pyrazol-4-yl)-quinoxalin-2-yl]-amine | 331.38 | $^1$H NMR (DMSO-d6) 8.33 (s, 1H, —ArH), 8.273 (s, 1H, —ArH), 8.00-7.96 (m, 2H, —ArH), 7.82-7.79 (dd, 1H, —ArH), 7.52-7.5 (d, 1H, —ArH), 7.26-7.22 (t, 1H, —ArH), 6.97-6.95 (d, 2H, —ArH), 6.82-6.80 (d, 1H, —ArH), 4.5-4.6 (d, 2H, —CH), and 3.718 (s, 3H, —CH$_3$) | D | 5.546 | 332.1 |
| 19 | (2-Methoxy-benzyl)-[6-(1H-pyrazol-4-yl)-quinoxalin-2-yl]-amine | 331.38 | $^1$H NMR (DMSO-d6) 12.93 (s, 1H, —NH), 8.36 (s, 1H, —ArH), 7.96-7.95 (d, 1H, —ArH), 7.91-7.94 (t, 1H, ArH) 7.83-7.78 (m, 3H, —ArH), 7.51-7.49 (d, 1H, —ArH), 7.31-7.29 (d, 1H, —ArH), 7.26-7.23 (t, 1H, —ArH), 7.02-7.00 (d, 1H, —ArH), 6.9-6.87 (t, 1H ArH) 4.56-4.54 (d, 2H, —CH), and 4.43 (s, 1H, —NH), 3.83(s, 3H, —OCH$_3$) | D | 5.741 | 332.05 |
| 20 | (4-Fluoro-3-trifluoromethyl-benzyl)-[6-(1H-pyrazol-4-yl)-quinoxalin-2-yl]-amine | 387.34 | $^1$H NMR (DMSO-d6) 13.1-12.8 (br s, 1H), 8.33 (s, 1H), 8.28-8.09 (s, 2H), 8.00 (s, 1H), 7.91-7.72 (m, 3H), 7.59-7.42 (m, 2H), 4.65 (d, 2H), 4.48 (br s, 1H). | G | 5.584 | 388 |
| 21 | (4-Fluoro-benzyl)-methyl-[6-(1H-pyrazol-4-yl)-quinoxalin-2-yl]-amine | 333.37 | $^1$H NMR (DMSO-d6) 8.67 (s, 1H), 8.18 (s, 2H), 8.03 (s, 1H), 7.87 (d, 1H), 7.56 (d, 1H), 7.40-7.29 (m, 2H), 7.14 (m, 2H), 4.93 (s, 2H), 3.20 (s, 3H). | E | 6.888 | 334 |
| 22 | Benzyl-methyl-(6-pyridin-4-yl-quinoxalin-2-yl)-amine | 326.40 | $^1$H NMR (DMSO-d6) 8.76 (s, 1H), 8.62 (br s, 2H), 8.26 (s, 1H), 8.03 (dd, 1H), 7.83 (d, 2H), 7.70 (d, 1H), 7.38-7.20 (m, 5H), 5.00 (d, 2H), 3.26 (s, 3H). | | | 327.1 |

-continued

| Ex. No. | Compound Name | Mol. Wt. | NMR (d6-DMSO) | LCMS, conditions | LCMS rt (min) | Mass ion (MH+) |
|---|---|---|---|---|---|---|
| 23 | Benzyl-methyl-(6-pyrimidin-4-yl-quinoxalin-2-yl)-amine | 327.39 | $^1$H NMR (DMSO-d6) 9.27 (s, 1H), 8.85 (d, 1H), 8.80 (s, 1H), 8.69 (s, 1H), 8.49-8.38 (m, 1H), 8.28-8.20 (m, 1H), 7.72 (d, 1H), 7.41-7.19 (m, 5H), 5.03 (s, 2H). | E | 7.258 | 328 |
| 24 | ((S)-1-Phenyl-ethyl)-[6-(1H-pyrazol-4-yl)-quinoxalin-2-yl]-amine hydrochloride | 315.38 | $^1$H NMR (DMSO-d6) 8.34 (s, 1H), 8.28 (br s, 1H), 8.02 (d, 2H), 7.99 (br s, 1H), 7.94 (d, 1H), 7.78 (dd, 2H), 7.43 (d, 2H), 7.31 (t, 5H), 7.2 (t, 1H), 5.28-5.18 (m, 1H), 1.48 (d, 3H). | E | 6.740 | 316 |
| 25 | Phenethyl-[6-(1H-pyrazol-4-yl)-quinoxalin-2-yl]-amine hydrochloride | 315.38 | $^1$H NMR (DMSO-d6) 8.44 (br s, 1H), 8.2 (s, 2H), 8.08 (s, 1H), 7.92 (d, 1H), 7.72 (d, 1H), 7.38-7.28 (m, 3H), 7.32-7.28 (m, 1H), 3.66-3.72 (m, 2H), 2.95 (t, 2H) | E | 6.725 | 316 |
| 26 | Benzyl-ethyl-[6-(1H-pyrazol-4-yl)-quinoxalin-2-yl]-amine | 329.41 | $^1$H NMR (DMSO-d6) 12.9 (s, 1H), 8.58 (s, 1H), 8.3 (s, 1H), 8.05-7.98 (m, 2H), 7.91 (d, 1H), 7.55 (d, 1H), 7.22-7.36 (m, 5H), 4.92 (s, 2H), 3.72 (q, 2H), 1.27 (t, 3H) | | | 330.1 |
| 27 | (3-Methoxy-benzyl)-methyl-[6-(1H-pyrazol-4-yl)-quinoxalin-2-yl]-amine | 345.41 | $^1$H NMR (DMSO-d6) 12.98 (s, 1H), 8.63 (s, 1H), 8.3 (s, 1H), 8.04 (s, 2H), 7.88 (d, 1H), 7.57 (d, 1H), 7.21 (t, 1H), 6.86-6.78 (m, 3H), 4.91 (s, 2H), 3.69 (s, 3H), 3.21 (s, 3H) | | 8.14 | 346.1 |
| 28 | (3-Fluoro-benzyl)-methyl-[6-(1H-pyrazol-4-yl)-quinoxalin-2-yl]-amine | 333.37 | 1HNMR (DMSO-d6) 12.95 (br s, 1H), 8.65 (s, 1H), 8.30 (br s, 1H), 8.05 (s, 2H), 7.90 (dd, 1H), 7.55 (d, 1H), 7.35 (q, 1H), 7.10 (m, 3H), 4.95 (s, 2H), 3.25 (s, 3H). | | | 334 |
| 29 | (4-Fluoro-3-trifluoromethyl-benzyl)-methyl-[6-(1H-pyrazol-4-yl)-quinoxalin-2-yl]-amine | 401.37 | 1HNMR (DMSO-d6) 13.0 (br s, 1H), 8.68 (s, 1H), 8.30 (brs, 1H), 8.05 (br s, 2H), 7.88 (dd, 1H), 7.77 (d, 1H), 7.68-7.62 (m, 1H), 7.57 (d, 1H), 7.45 (t, 1H), 4.98 (s, 2H), 3.25 (s, 3H). | H | 7.06 | 402.05 |
| 30 | [6-(1H-Pyrazol-4-yl)-quinoxalin-2-yl]-(3-trifluoromethoxy-benzyl)-amine | 385.35 | 1HNMR (DMSO-d6) 12.95 (br s, 1H), 8.35 (s, 1H), 8.28 (br s, 1H), 8.12 (t, 1H), 8.01 (br s, 1H), 7.97 (d, 1H), 7.82 (dd, 1H), 7.51-7.39 (m, 4H), 7.23 (d, 1H), 4.65 (d, 2H). | | | 386.0 |
| 31 | [3-(2-Dimethylamino-ethoxy)-benzyl]-[6-(1H-pyrazol-4-yl)-quinoxalin-2-yl]-amine hydrochloride | 388.48 | 1HNMR (DMSO-d6) 10.0 (br s, 1H), 8.42 (s, 1H), 8.35 (br s, 1H), 8.18 (d, 2H), 8.02 (d, 1H), 7.85 (dd, 1H), 7.57 (d, 1H), 7.31 (t, 1H), 7.09-7.03 (m, 2H), 6.91 (dd, 1H), 4.62 (d, 2H), 4.30 (t, 2H), 3.45 (t, 2H), 2.82 (s, 6H). | E | 5.72 | 389 |
| 32 | (3,4-Difluoro-benzyl)-[6-(1H-pyrazol-4-yl)-quinoxalin-2-yl]-amine | 337.33 | 1HNMR (DMSO-d6) 12.96 (br s, 1H), 8.33 (s, 1H), 8.29 (br s, 1H), 8.08 (t, 1H), 8.01 (br s, 1H), 7.99 (d, 1H), 7.82 (dd, 1H), 7.52-7.35 (m, 3H), 7.25 (br s, 1H), 4.59 (d, 2H). | | | 338 |
| 33 | ((R)-1-Phenyl-ethyl)-[6-(1H-pyrazol-4-yl)-quinoxalin-2-yl]-amine | 315.38 | 1HNMR (DMSO-d6) 12.95 (br s, 1H), 8.33 (s, 1H), 8.13 (br s, 1H), 8.01 (d, 1H), 7.94 (d, 1H), 7.78 (dd, 1H), 7.43 (d, 2H), 7.32 (t, 2H), 7.20 (t, 1H), 5.26-5.22 (m, 1H), 1.50 (d, 3H) | | | 316 |
| 34 | Benzyl-methyl-[1-oxy-7-(1H-pyrazol- | 332.37 | 1HNMR (DMSO-d6) 13.1 (brs, 1H), 8.31 (d, 1H), | | | 333.1 |

-continued

| Ex. No. | Compound Name | Mol. Wt. | NMR (d6-DMSO) | LCMS, conditions | LCMS rt (min) | Mass ion (MH+) |
|---|---|---|---|---|---|---|
|  | 4-yl)-benzo[1,2 4]triazin-3-yl]-amine |  | 8.25 (brs, 2H), 8.13 (dd, 1H), 7.63 (d, 1H), 7.37-7.23 (m, 5H), 4.90 (s, 2H), 3.13 (s, 3H). |  |  |  |
| 35 | Benzyl-methyl-[7-(1H-pyrazol-4-yl)-benzo[1,2,4]triazin-3-yl]-amine | 316.37 | 1HNMR (DMSO-d6) 13.07 (brs, 1H), 8.44 (d, 1H), 8.30 (brs, 2H), 8.16 (dd, 1H), 7.63 (d, 1H), 7.35-7.23 (m, 5H), 5.10 (brs, 2H), 3.31 (s, 3H). | G | 5.84 | 317 |
| 36 | (3-Methoxy-benzyl)-[1-oxy-7-(1H-pyrazol-4-yl)-benzo[1,2,4]triazin-3-yl]-amine | 348.37 | 1HNMR (DMSO-d6) 13.08 (br s, 1H), 8.45-8.25 (m, 3H), 8.09 (d, 2H), 7.57 (d, 1H), 7.22 (t, 1H), 6.98-6.91 (m, 2H), 6.80 (s, 1H), 4.54 (d, 2H), 3.71 (s, 3H). | E | 6.53 | 349 |
| 37 | (3-Methoxy-benzyl)-[7-(1H-pyrazol-4-yl)-benzo[1,2,4]triazin-3-yl]-amine | 332.37 | 1HNMR (DMSO-d6) 13.05 (br s, 1H), 8.84 (br s, 1H), 8.42 (m, 2H), 8.10 (dd, 2H), 7.55 (d, 1H), 7.21 (t, 1H), 6.98-6.94 (m, 2H), 6.80 (dd, 1H), 4.60 (br s, 2H), 3.70 (s, 3H) |  |  | 332.9 |
| 38 | [6-(1H-Pyrazol-4-yl)-quinoxalin-2-yl]-thiophen-3-ylmethyl-amine | 307.38 | 1HNMR(DMSO-d6) 12.94 (brs, 1H, —NH), 8.34 (s, 1H, —ArH), 8.16 (s, 2H, —ArH), 7.99-7.98 (d, 1H, —ArH), 7.94-7.96 (t, 1H, —ArH), 7.82-7.85 (dd, 1H, —ArH), 7.54-7.57 (d, 1H, —ArH), 7.50-7.52 (m, 1H, —ArH), 7.44-7.45 (m, 1H, —ArH), 7.16-7.17 (dd, 1H, —ArH), and 4.60-4.61 (s, 2H, —CH2). |  |  | 308 |
| 39 | Naphthalen-2-ylmethyl-[6-(1H-pyrazol-4-yl)-quinoxalin-2-yl]-amine hydrochloride | 351.41 | 1HNMR (DMSO-d6) 8.43 (s, 1H, —ArH), 8.13 (s, 2H, —ArH), 8.00 (s, 1H, —ArH), 7.85-7.90 (m, 5H, —ArH), 7.54-7.59 (t, 2H, —ArH), 7.45-7.51 (q, 2H, —ArH), 4.80 (s, 2H, —CH2). |  |  | 352 |
| 40 | [6-(1H-Pyrazol-4-yl)-quinoxalin-2-yl]-(4-trifluoromethyl-benzyl)-amine | 369.35 | 1H NMR (DMSO-d6)12.96 (s, 1H), 8.38 (brs, 1H, —ArH), 8.30 (t, 1H, —ArH), 8.15-8.18 (t, 1H, —ArH), 8.0-8.02 (m, 2H, —ArH), 7.82-7.84 (dd, 1H, —ArH), 7.70-7.72 (d, 2H, —ArH), 7.61-7.63 (d, 2H, —ArH), 7.49-7.51 (d, 1H, —ArH) and 4.71-4.73 (s, 2H, —CH2—), | E | 6.94 | 370 |
| 41 | (3-Methyl-benzyl)-[6-(1H-pyrazol-4-yl)-quinoxalin-2-yl]-amine | 315.38 | 1H NMR (DMSO-d6)12.96 (brs, 1H, —ArH), 8.35 (s, 1H, —ArH), 8.29 (brs, 1H, —ArH), 7.98-8.02 (m, 3H, —ArH), 7.81-7.84 (d, 1H, —ArH), 7.52-7.54 (d, 1H, —ArH), 7.25-7.08 (m, 3H, —ArH), 7.07-7.08 (d, 1H, —ArH), 4.57-4.59 (d, 1H, —CH2) and 2.29 (s, 3H, —CH2—), | H | 7.51 | 316 |
| 42 | (2-Methyl-benzyl)-[6-(1H-pyrazol-4-yl)-quinoxalin-2-yl]-amine | 327.39 | 1HNMR(DMSO-d6) 9.282 (s, 2H, —ArH), 9.191 (s, 1H, —ArH), 8.783 (s, 1H, —ArH), 8.314-8.308 (d, 1H, —ArH), 8.074-8.047 (dd, 1H, —ArH), 7.745-7.723 (d, 1H, —ArH), 7.370-7.255 (m, 5H, —ArH), 5.022(s, 2H, —CH2), 3.289(s, 3H, —CH3). | E | 7.06 | 328 |
| 43 | Benzyl-methyl-(6-pyrimidin-5-yl-quinoxalin-2-yl)-amine | 315.38 | 1HNMR(DMSO-d6) 8.37 (s, 1H, —ArH), 8.15 (s, 2H, —ArH), 7.98-7.99 (d, 1H, —ArH), 7.89-7.92 (t, 1H, —ArH), 7.81-7.84 (dd, 1H, | E | 6.86 | 316 |

-continued

| Ex. No. | Compound Name | Mol. Wt. | NMR (d6-DMSO) | LCMS, conditions | LCMS rt (min) | Mass ion (MH+) |
|---|---|---|---|---|---|---|
| | | | —ArH), 7.52-7.54 (d, 1H, —ArH), and 7.35-7.37 (dd, 1H, —ArH), 7.15-7.22(m, 3H, —ArH), 4.56-4.58(s, 2H, —CH2), 4.47(brs, 1H, —NH—), 2.37(s, 3H, —CH3). | | | |
| 44 | (4-Methyl-benzyl)-[6-(1H-pyrazol-4-yl)-quinoxalin-2-yl]-amine | 315.38 | 1HNMR(DMSO-d6) 12.96 (s, 1H, —NH), 8.345 (s, 1H, —ArH), 8.293 (s, 1H, —ArH), 8.022-7.970 (d, 3H, —ArH), 7.840-7.813 (dd, 1H, —ArH), 7.536-7.514 (d, 1H, —ArH), 7.310-7.290 (d, 2H, —ArH), 7.16-7.143 (d, 2H, —ArH), 4.576-4.562(s, 2H, —CH2), 2.280(s, 3H, —CH3). | E | 6.93 | 316 |
| 45 | (2-Chloro-benzyl)-methyl-[6-(1H-pyrazol-4-yl)-quinoxalin-2-yl]-amine hydrochloride | 349.83 | 1H NMR (DMSO-d6) 8.708 (s, 1H, —ArH), 8.240 (s, 2H, —ArH), 8.089-8.085 (S, 1H, —ArH), 7.919-7.982 (dd, 1H, —ArH), 7.625-7.604 (d, 1H, —ArH), 7.534-7.511 (d, 1H, —ArH), 7.346-7.305(m, 2H, —ArH), 7.291-7.196(d, 1H, —ArH), 5.039 (s, 2H, —CH)and 3.219 (s, 3H, —CH$_2$) | H | 7.25 | 350 |
| 46 | Benzyl-[6-(5-methyl-1H-pyrazol-4-yl)-quinoxalin-2-yl]-amine hydrochloride | 315.38 | 1HNMR(DMSO-d6) 8.41 (s, 1H, —ArH), 7.92 (s, 1H, —ArH), 7.818-7.814 (d, 1H, —ArH), 7.72-7.69 (dd, 1H, —ArH), 7.62-7.60 (d, 1H, —ArH), 7.42-7.41 (d, 2H, —ArH), 7.36-7.32 (t, 2H, —ArH), 7.28-7.25 (t, 1H, —ArH), 4.64(s, 2H, —CH2), 2.41(s, 2H, —CH2). | E | 6.79 | 316 |
| 47 | {(R)-1-[3-(4-Methyl-piperazin-1-yl)-phenyl]-ethyl}-[6-(1H-pyrazol-4-yl)-quinoxalin-2-yl]-amine hydrochloride | 413.53 | 1HNMR(DMSO-d6) 10.58 (brs, 1H, —NH), 8.49 (s, 1H, —ArH), 8.19 (s, 2H, —ArH), 8.02 (s, 1H, —ArH), 7.86-7.88 (d, 1H, —ArH), 7.67 (s, 1H, —ArH), 7.19-7.25 (m, 2H, —ArH), 6.99-7.01 (d, 1H, —ArH), 6.88-6.90 (d, 1H, —CH), 5.76 (q, 1H, —CH2), 3.83-3.86 (d, 2H, —CH2), 3.03-3.17 (m, 6H, —CH2), 2.81-2.82 (d, 3H, —2(CH3)), 1.53-1.55(d, 3H, —CH3). | | | 414 |
| 48 | Methyl-[3-(4-methyl-piperazin-1-yl)-benzyl]-[6-(1H-pyrazol-4-yl)-quinoxalin-2-yl]-amine | 413.53 | 1HNMR(DMSO-d6) 12.93 (brs, 1H, —NH), 8.63 (s, 1H, —ArH), 8.16 (brs, 2H, —ArH), 8.01 (d, 1H, —ArH), 7.85-7.87 (dd, 1H, —ArH), 7.55-7.58 (d, 1H, —ArH), 7.10-7.14 (t, 1H, —ArH), 6.89 (s, 1H, —ArH), 6.79-6.81 (dd, 1H, —ArH), 6.63-6.64 (d, 1H, —ArH), 4.87 (s, 2H, —CH2), 3.22 (s, 3H, —CH2), 3.06-3.09 (t, 4H, —CH2), 2.38-2.40 (t, 4H, —CH2) and 2.17 (s, 3H, —CH2). | | | 414 |
| 49 | [(R)-1-(3-Fluoro-phenyl)-ethyl]-[6-(1H-pyrazol-4-yl)-quinoxalin-2-yl]-amine hydrochloride | 333.37 | 1H NMR(DMSO-d6) 8.42 (s, 2H, —ArH), 8.18 (s, 2H, —ArH), 8.00 (s, 1H, —ArH), 7.82-7.85 (dd, 1H, —ArH), 7.52-7.54 (d, 1H, —ArH), 7.37-7.41 (q, 1H, —ArH), 7.29-7.36 (m, 2H, —ArH), 7.04-7.08 (t, 1H, —ArH), 5.30-5.33 (q, 1H, —CH), and 1.52-1.54 (d, 3H, —CH3). | | | 334 |
| 50 | [(R)-1-(3-Methoxy-phenyl)-ethyl]-[6-(1H-pyrazol-4-yl)- | 345.41 | 1HNMR(DMSO-d6) 8.34 (s, 1H, —ArH), 8.13 (s, 3H, —ArH), 7.95 (d, 1H, —ArH), | | | 346 |

-continued

| Ex. No. | Compound Name | Mol. Wt. | NMR (d6-DMSO) | LCMS, conditions | LCMS rt (min) | Mass ion (MH+) |
|---|---|---|---|---|---|---|
| | quinoxalin-2-yl]-amine hydrochloride | | 7.78-7.80 (dd, 1H, —ArH), 7.45-7.47 (d, 1H, —ArH), 7.20-7.241 (t, 1H, —ArH), 6.99 (d, 2H, —ArH), 6.76-6.78 (dd, 1H, —ArH), 5.19-5.21 (t, 1H, —CH2), 3.71 (s, 3H, —CH2), and 1.48 (d, 3H, —CH3). | | | |
| 51 | Methyl-((R)-1-phenyl-ethyl)-[6-(1H-pyrazol-4-yl)-quinoxalin-2-yl]-amine | 329.41 | 1HNMR(DMSO-d6) 12.99 (brs, 1H, —ArH), 8.72 (s, 1H, —ArH), 8.19 (s, 2H, —ArH), 8.05-8.06 (d, 1H, —ArH), 7.88-7.91 (dd, 1H, —ArH), 7.59-7.60 (d, 1H, —ArH), 7.36-7.37 (d, 4H, —ArH), 7.26-7.30 (m, 1H, —ArH), 6.18-6.20 (q, 1H, —ArH), 2.95 (s, 3H, —CH2), and 1.60-1.62 (d, 3H, —CH3). | | | 330 |
| 52 | [(R)-1-(3-Fluoro-phenyl)-ethyl]-methyl-[6-(1H-pyrazol-4-yl)-quinoxalin-2-yl]-amine hydrochloride | 347.40 | 1HNMR(DMSO-d6) 8.75 (s, 1H, —ArH), 8.25 (s, 2H, —ArH), 8.08 (s, 1H, —ArH), 7.90-7.93 (dd, 1H, —ArH), 7.62-7.64 (d, 1H, —ArH), 7.38-7.43 (q, 1H, —ArH), 7.20-7.22 (m, 2H, —ArH), 7.10-7.14 (t, 1H, —ArH), 6.19-6.21 (q, 1H, —CH), 2.98 (s, 3H, —CH3) and 1.60-1.62 (d, 3H, —CH3). | | | 348 |
| 53 | [(R)-1-(3-Methoxy-phenyl)-ethyl]-methyl-[6-(1H-pyrazol-4-yl)-quinoxalin-2-yl]-amine hydrochloride | 359.43 | 1HNMR(DMSO-d6) 8.749 (s, 1H, —ArH), 8.22 (s, 2H, —ArH), 8.07 (d, 1H, —ArH), 7.90-7.92 (dd, 1H, —ArH), 7.62-7.64 (d, 1H, —ArH), 7.26-7.30 (t, 1H, —ArH), 6.85-6.95 (m, 3H, —ArH), 6.13-6.14 (q, 1H, —ArH), 3.73 (s, 3H, —CH2), 2.97 (s, 3H, —CH2), and 1.59-1.60 (d, 3H, —CH2). | | | 360 |
| 54 | 3-{[6-(1H-Pyrazol-4-yl)-quinoxalin-2-ylamino]-methyl}-phenol | 317.35 | 1HNMR(ACN) 11.1 (s, 1H, —ArH), 8.28 (s, 1H, —ArH), 7.99-7.98 (s, 2H, —ArH), 7.79-7.77 (d, 1H, —ArH), 7.57-7.55 (d, 1H, —ArH), 7.19-7.15 (t, 1H, —ArH), 6.90-6.92 (d, 1H, —ArH), 6.86 (s, 1H, —ArH), 6.70-6.68 (dd, 1H, —ArH), 6.34 (t, 1H, —ArH), and 4.63-4.62 (s, 2H, —CH2). | E | 5.93 | 318 |
| 55 | [(R)-1-(3-Chloro-phenyl)-ethyl]-[6-(1H-pyrazol-4-yl)-quinoxalin-2-yl]-amine hydrochloride | 349.83 | 1HNMR(DMSO-d6) 8.39 (s, 1H, —ArH), 8.17 (s, 1H, —ArH), 7.99 (s, 2H, —ArH), 7.84-7.82 (d, 1H, —ArH), 7.52-7.50 (dd, 1H, —ArH), 7.48 (t, 2H, —ArH), 7.44-7.42 (d, 1H, —ArH), 7.39-7.35 (t, 1H, —ArH), 7.30-7.28 (d, 1H, —ArH), 5.27 (q, 1H, —CH2), 1.53-1.51 (d, 3H, —CH2). | E | 7.15 | 350 |
| 56 | [(R)-1-(3-Chloro-phenyl)-ethyl]-methyl-[6-(1H-pyrazol-4-yl)-quinoxalin-2-yl]-amine | 363.85 | 1HNMR(DMSO-d6) 8.73 (s, 1H, —ArH), 8.35 (s, 1H, —ArH), 8.07 (s, 2H, —ArH), 7.89-7.92 (dd, 1H, —ArH), 7.59-7.61 (d, 1H, —ArH), 7.32-7.41 (m, 4H, —ArH), 6.19-6.21 (q, 1H, —CH2), 2.98 (s, 3H, —CH3), 1.60-1.61 (d, 3H, —CH2). | | 7.54 | 364 |
| 57 | Methyl-((S)-1-phenyl-ethyl)-[6-(1H-pyrazol-4-yl)-quinoxalin-2-yl]- | 329.41 | 1HNMR(DMSO-d6) 8.76 (s, 1H, —ArH), 8.22 (s, 2H, —ArH), 8.07-8.08 (d, 1H, —ArH), 7.90-7.93 (dd, 1H, | | | 330 |

| Ex. No. | Compound Name | Mol. Wt. | NMR (d6-DMSO) | LCMS, conditions | LCMS rt (min) | Mass ion (MH+) |
|---|---|---|---|---|---|---|
| | amine | | —ArH), 7.62-7.65 (d, 1H, —ArH), 7.36-7.38 (d, 4H, —ArH), 7.28-7.30 (m, 1H, —ArH), 6.18-6.20 (q, 1H, —ArH), 2.96 (s, 3H, —CH2), and 1.61-1.62 (d, 3H, —CH3). | | | |
| 58 | [6-(1H-Pyrazol-4-yl)-quinoxalin-2-yl]-((R)-1-m-tolyl-ethyl)-amine hydrochloride | 329.41 | 1HNMR(DMSO-d6) 9.02(s, 1H, —NH), 8.51 (s, 1H, —ArH), 8.22 (s, 2H, —ArH), 8.05(s, 1H, —ArH), 7.91-7.89 (d, 1H, —ArH), 7.70 (d, 1H, —ArH), 7.32-7.23 (m, 3H, —ArH), 7.09-7.07 (d, 1H, —ArH), 5.38(brs, 1H, —CH), 2.31(s, 3H, —CH3), 1.56-1.54(d, 3H, —CH3). | | | 330 |
| 59 | [(S)-1-(3-Fluoro-phenyl)-ethyl]-[6-(1H-pyrazol-4-yl)-quinoxalin-2-yl]-amine hydrochloride | 333.37 | 1HNMR(DMSO-d6) 8.37 (s, 1H, —ArH), 8.29 (s, 1H, —ArH), 8.14 (s, 2H, —ArH), 7.97 (s, 1H, —ArH), 7.79-7.81 (d, 1H, —ArH), 7.47-7.49 (d, 1H, —ArH), 7.27-7.38 (m, 3H, —ArH), 7.01-7.05 (m, 1H, —ArH), 5.25-5.28 (t, 1H, —CH2), and 1.49-1.51 (d, 3H, —CH2). | | | 334 |
| 60 | [(S)-1-(3-Fluoro-phenyl)-ethyl]-methyl-[6-(1H-pyrazol-4-yl)-quinoxalin-2-yl]-amine | 347.40 | 1HNMR(DMSO-d6) 13.001 (s, 1H, —ArH), 8.725 (s, 1H, —ArH), 8.344 (s, 1H, —ArH), 8.073-8.069 (s, 2H, —ArH), 7.913-7.891 (d, 1H, —ArH), 7.612-7.591 (d, 1H, —ArH), 7.433-7.377 (q, 1H, —ArH), 7.216-7.187 (t, 2H, —ArH), 7.138-7.098 (t, 1H, —ArH), 6.234-6.182 (q, 1H, —CH2), 2.977 (s, 3H, —CH2) and 1.619-1.601 (d, 3H, —CH2). | | | 348 |

Example 61

Benzyl-[1-oxy-7-(1H-pyrazol-4-yl)-benzo[1,2,4]triazin-3-yl]-amine

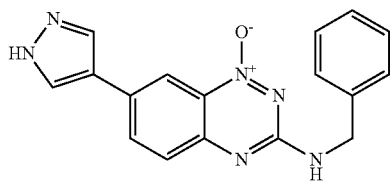 [SMILES: [O-][n+]1nc(NCc2ccccc2)nc2ccc(-c3cn[nH]c3)cc21]

The sequence of reactions described in this example follows the synthetic route set out in Scheme 1 above.

Step A

A mixture of 4-chloro-2-nitro-phenylamine (72.4 mmol) and cyanamide (476 mmol) was heated at 100° C. for 5 min. The mixture was cooled, 25 mL of conc. HCl was carefully added and the mixture heated to 70° C. The mixture was vigorously stirred and after gas evolution has ceased, the mixture was cooled to room temperature. A solution of 50% NaOH (50 mL) was added dropwise to the mixture and the mixture was heated at 100° C. for 30 min. The resulting precipitate was filtered, the filter cake washed with hot acetic acid, and then dried to give [7-chloro-1-oxy-benzo[1,2,4]triazin-3-yl]amine as a yellow solid.

Step B

The product of Step A (61.1 mmol) was dissolved in 2 M HCl (300 mL). The mixture was cooled to 5° C. and a solution of NaNO$_2$ (10 g, 145 mmol) in water (100 mL) was added dropwise. The resulting precipitate was removed by filtration. The filter cake was dissolved in dilute NH$_3$ and acidified with conc. HCl. The precipitate was filtered, washed with water and dried to give 7-chloro-3-hydroxy-1-oxy-benzo[1,2,4]triazine as a yellow solid.

Step C

A mixture of the product of Step B (17.2 mmol), N,N-dimethylbenzenamine (5.5 ml, 37.4 mmol) and POCl$_3$ (11.5 ml, (0.1234 mol) was heated to reflux for 1 h. The mixture was then poured into ice. The resulting solid was filtered and washed with water to give a crude product which may be crystallized with ethyl acetate to give 3,7-dichloro-1-oxy-benzo[1,2,4]triazine as a pale yellow solid.

Step D 3,7-dichloro-1-oxy-benzo[1,2,4]triazine (1.0 mmol) from Step C was dissolved in DMF (5 ml) and K$_2$CO$_3$ (1.1 mmol) was added followed by addition of benzylamine (1.1 mmol).

The mixture was stirred at room temperature overnight. The product was precipitated from water and filtered, washed with water and dried to give 3-benzylamino-7-dichloro-1-oxy-benzo[1,2,4]triazine.

Step E—Benzyl-[1-oxy-7-(1H-pyrazol-4-yl)-benzo[1,2,4]triazin-3-yl]-amine

3-Benzylamino-7-dichloro-1-oxy-benzo[1,2,4]triazine (1.0 mmol) was suspended in 5 ml DMF. To this was added $Cs_2CO_3$ (1.1 mmol) and Fu's catalyst (10% by mol), followed by addition of 1-tert-butyloxycarbonyl-(4-(4,4,5,5-tetramethyl-1,3,2-dioxaborolan-2-yl)-1H-pyrazole (1.0 mmol). The mixture was degassed three times by evacuation/$N_2$ filling and heated at 80° C. overnight. The mixture was concentrated and loaded onto a silica gel column and purified by column chromatography using a gradient of 0-10% 7N $NH_3$/MeOH and DCM to give the title compound.

$^1$H NMR: δ 13.10 (br s, 1H), 8.44 (br s, 1H), 8.39 (br t, 1H), 8.30 (d, 1H), 8.14-8.07 (m, 2H), 7.58 (d, 1H), 7.39 (br d, 2H), 7.33 (br t, 2H), 7.25 (br t, 1H), 4.60 (br d, 2H)
LCMS: RT 2.41, m/z 319.3

Example 62

(4-Chloro-benzyl)-[1-oxy-7-(1H-pyrazol-4-yl)-benzo[1,2,4]triazin-3-yl]-amine

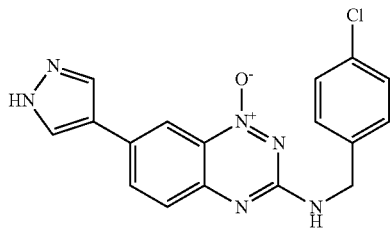 [SMILES: [O-][n+]1nc(NCc2ccc(Cl)cc2)nc2ccc(-c3cn[nH]c3)cc21]

The title compound was prepared using the same methods and conditions as described in Example 61 except that 4-chlorobenzylamine was used in Step D instead of benzylamine.

$^1$H NMR δ 8.48-8.36 (m, 1H), 8.31 (s, 1H), 8.10 (d, 2H), 7.58 (d, 1H), 7.42-7.39 (m, 4H), 4.58 (d, 2H)
LCMS: RT 2.65, m/z 353.4

Example 63

(3-Chloro-benzyl)-[1-oxy-7-(1H-pyrazol-4-yl)-benzo[1,2,4]triazin-3-yl]-amine

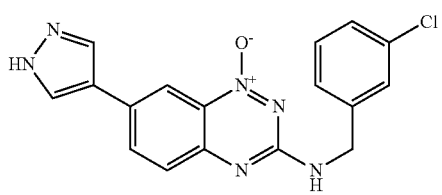 [SMILES: [O-][n+]1nc(NCc2cccc(Cl)c2)nc2ccc(-c3cn[nH]c3)cc21]

The title compound was prepared using the same methods and conditions as described in Example 61 except that 3-chlorobenzylamine was used in Step D instead of benzylamine. In this case, Step E gave rise to the N-Boc protected compound (3-chloro-benzyl)-[1-oxy-7-(1-tert-butoxycarbonyl-1H-pyrazol-4-yl)-benzo[1,2,4]triazin-3-yl]-amine. A further Step F was therefore required in order to remove the Boc group.

Step F (3-Chloro-benzyl)[1-oxy-7-(1-tert-butoxycarbonyl-1H-pyrazol-4-yl)-benzo[1,2,4]triazin-3-yl]-amine (100 mg) was suspended in 4 N HCl in dioxane (5 ml) and stirred overnight. The precipitate was filtered and washed with diethyl ether and dried to obtain (3-chloro-benzyl)-[1-oxy-7-(1H-pyrazol-4-yl)-benzo[1,2,4]triazin-3-yl]-amine (60 mg, 61% yield).

$^1$H NMR δ 13.10 (br s, 1H), 8.44 (br s, 1H), 8.39 (br m, 1H), 8.31 (s, 1H), 8.16-8.06 (m, 2H), 7.58 (d, 1H), 7.45 (s, 1H), 7.39-7.24 (m, 4H), 4.60 (d, 2H)
LCMS: RT 2.66, m/z 353.4

Example 64

Benzyl-[7-(1H-pyrazol-4-yl)-benzo[1,2,4]triazin-3-yl]-amine

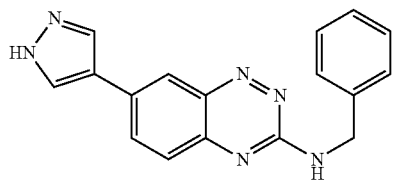 [SMILES: c1ccc(CNc2nnc3cc(-c4cn[nH]c4)ccc3n2)cc1]

Benzyl-[1-oxy-7-(1H-pyrazol-4-yl)-benzo[1,2,4]triazin-3-yl]-amine (200 mg, 0.628 mmol) from Example 61 was dissolved in 70% ethanol/water (10 ml) and $Na_2S_2O_4$ (3.14 mmol) was added. The mixture was heated at reflux for 2 hours. The reaction mixture was then diluted with water, filtered and washed with water. The crude solid material was purified by column using 0-100% 7N $NH_3$/MeOH in DCM. The product was triturated with diethyl ether, filtered and dried to afford the title compound as a yellow solid.

$^1$H NMR δ 13.07 (br s, 1H), 8.98-8.78 (br s, 1H), 8.44 (br s, 2H), 8.20-8.09 (m, 2H), 7.57 (d, 1H), 7.41 (d, 2H), 7.33 (t, 2H), 7.24 (t, 1H), 4.71-4.60 (br m, 2H)
LCMS: RT 2.43, m/z 303.4

Example 65

Alternative synthesis of Benzyl-[4-oxy-6-(1H-pyrazol-4-yl)-quinoxalin-2-yl]-amine

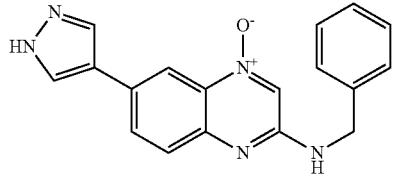 [SMILES: [O-][n+]1cc(NCc2ccccc2)nc2ccc(-c3cn[nH]c3)cc21]

The sequence of reactions described in this Example follows the synthetic route set out in Scheme 2 above.

Step A

To a solution of 2,6-dichloroquinoxaline (2.0 g, 10.0 mmol) in DMSO (25 mL) was added benzylamine (5.5 mL, 50.0 mmol). The mixture was stirred at room temperature for 72 h. Water (100 mL) was added to the reaction mixture. The mixture was extracted with EtOAc (3×50 mL) and the organic layer was washed with water (2×50 mL) and dried over Mg$_2$SO$_4$. The organic solution was concentrated and purified by chromatography on silica gel (petroleum ether/EtOAc/NEt$_3$=10/1/0.1) to give benzyl-[4-oxy-6-chloro-quinoxalin-2-yl]-amine as a yellow solid (2.8 g, yield: 100%)

Step B: Preparation of Benzyl-[6-(1H-pyrazol-4-yl)-quinoxalin-2-yl]-amine

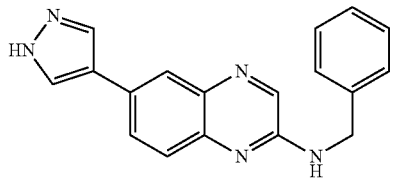 [SMILES: c1ccc(CNc2cnc3cc(-c4cn[nH]c4)ccc3n2)cc1]

A mixture of benzyl-[4-oxy-6-chloro-quinoxalin-2-yl]-amine (270 mg, 1.0 mmol), 1-Boc-pyrazole-4-boronic acid pinacol ester (353 mg, 1.2 mmol), K$_2$CO$_3$ (553 mg, 4 mmol) and bis(tri-t-butylphosphine)palladium (0) (26 mg, 0.05 mmol) in DMF (8 mL) (degassed three times with argon) was irradiated in a microwave to 80° C. for 3 minutes, then to 135° C. for 30 minutes. The reaction mixture was diluted with ethyl acetate (150 mL) and washed with water (20 mL×3) and brine (20 mL). The organic solvent was dried and concentrated to give a residue (280 mg). The residue was dissolved in a mixture of methanol (20 mL) and HCl (36% v/v, 4 mL) and the resulting mixture was stirred at room temperature for 16 h. Water (10 mL) was added and the mixture was neutralized with NaHCO$_3$. The aqueous phase was extracted with ethyl acetate (30 mL×4) and the combined organic phases were washed with brine (20 mL), dried and concentrated under reduced pressure. The crude product was purified by chromatography on silica gel (CH$_2$Cl$_2$/1 M NH$_3$ in CH$_3$OH of a ratio 30:1) to afford the title compound as a pale yellow solid (140 mg, yield: 47%).

$^1$H NMR δ 12.90 (br s, 1H), 8.37 (s, 1H), 8.34-8.24 (br s, 1H), 8.09-8.01 (m, 2H), 8.00 (d, 1H), 7.84 (dd, 1H), 7.53 (d, 1H), 7.42 (br d, 2H), 7.35 (br t, 2H), 7.27 (br t, 1H), 4.63 (br d, 2H)

LCMS: RT 2.36, m/z 302.4

Step C: Preparation of benzyl-[4-oxy-6-(1H-pyrazol-4-yl)-quinoxalin-2-yl]-amine

Hydrogen peroxide (30%, 2 mL) was added dropwise to a solution of benzyl-[6-(1H-pyrazol-4-yl)-quinoxalin-2-yl]-amine (180 mg, 0.6 mmol) in acetic acid (4 mL) and the mixture was stirred at 45-50° C. for 4 h. The solution was diluted with water (10 mL) and carefully neutralized with solid NaHCO$_3$. The solution was then extracted with ethyl acetate (20 mL×30) and ethyl acetate containing 15% n-BuOH (20 mL×5). The combined organic phases were then washed with a saturated aqueous solution of Na$_2$S$_2$O$_4$ (40 mL×3) and brine (40 mL×3). The organic solvent was dried and concentrated under reduced pressure to give a yellow solid (145 mg). The yellow solid was dissolved with small volume of DMSO and purified by chromatography on silica gel eluting with DCM/MeOH (a gradient from 40/1 to 20/1) to give the title compound as a yellow solid (32 mg) which was further purified by recrystallization in ethyl acetate to give a yellow solid (23 mg).

$^1$H NMR δ 12.88 (br s, 1H), 12.08 (br s, 1H), 8.03 (br s, 1H), 7.95 (t, 1H), 7.73 (br s, 1H), 7.34-7.11 (m, 8H), 4.53 (d, 2H)

LCMS: RT 2.27, m/z 318.4

Biological Activity

Example 66

Determination of p70S6 Inhibitory Activity

The ability of compounds of the invention to inhibit P70S6 kinase was determined using the protocol below.
Buffer Composition:
20 mM MOPS, 1 mM EDTA, 0.01% Brij-35, 5% Glycerol, 0.1% b-mercaptoethanol, 1 mg/mL BSA
Method:
p70S6K (h)

In a final reaction volume of 25 µL, p70S6K (h) (5-10 mU) is incubated with 8 mM MOPS pH 7.0, 0.2 mM EDTA, 100 µM KKRNRTLTV, 10 mM Mg acetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction mixture is then spotted onto a P30 filtermat and washed three times for 5 minutes in 75 mM phosphoric acid and once in methanol prior to drying and scintillation counting.

Using Protocol B, the compounds of Examples 1, 2, 3, 8, 9, 11, 12, 18, 21, 25, 26, 27, 28, 32, 33, 34, 35, 36, 38, 41, 43, 44, 48, 50, 51, 53, 54 and 55 were found to have IC$_{50}$ values of less than 0.1 µM. The compounds of Examples 6, 10, 13, 15, 17, 19, 20, 22, 23, 29, 30, 37, 39, 40, 45, 57, 60, 61, 62, 63, 64, 65B and 65C were all found to have IC$_{50}$ values of less than 1 µM. The compounds of Examples 7, 14, 16, 24, 31 and 59 were found to have IC$_{50}$ values of less than 5 µM.

Example 67

Determination of the Selectivity of the Compounds for p70S6 Versus Aurora A, Aurora B and Akt2 kinase The kinase selectivity of compounds of the invention was determined by comparing their inhibitory activity against p70S6 with their inhibitory activities against Aurora A, Aurora B and Akt2 kinases.

The assays set out or referenced below were used to determine the inhibitory activities against Aurora A, Aurora B and Akt2.
Aurora A
Buffer Composition:
20 mM MOPS, 1 mM EDTA, 0.01% Brij-35, 5% Glycerol, 0.1% b-mercaptoethanol, 1 mg/mL BSA
Method:

In a final reaction volume of 25 µL, Aurora-A (h) (5-10 mU) is incubated with 8 mM MOPS pH 7.0, 0.2 mM EDTA, 200 µM LRRASLG (Kemptide), 10 mM MgAcetate and [g-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 50 mM phosphoric acid and once in methanol prior to drying and scintillation counting.

Results:

The results of the assays showed that the compounds of Examples 1, 2, 3, 8, 9, 11, 12, 18, 25, 28, 32, 33, 38, 41, 43, 44, 48, 50, 51, 53 and 55 had a greater than 20 fold selectivity for p70S6 kinase over Aurora A. The compounds of Examples 17, 21 and 59 had a greater than 10 fold selectivity for p70S6 kinase over Aurora A. The compounds of Examples 6 and 9 had a greater than 5 fold selectivity for p70S6 kinase over Aurora A. The compounds of Examples 10, 26, 27, 34, 35 and 60 had a greater than 2 fold selectivity for p70S6 kinase over Aurora A.

Aurora B

Assays to determine the activities of the compounds against Aurora B kinase were carried out at Millipore UK Ltd, Gemini Crescent, Dundee Technology Park (see also http://www.millipore.com/).

The results of the assays showed that the compounds of Examples 1, 2, 3, 9, 11, 12, 25, 26, 28, 32, 33, 43, 50, 51 and 55 had a greater than 20 fold selectivity for p70S6 kinase over Aurora B. The compounds of Examples 18, 34, 38, 41, 48 and 53 had a greater than 10 fold selectivity for p70S6 kinase over Aurora B. The compounds of Examples 8, 21, 24, 35, 44, 59 and 60 had a greater than 5 fold selectivity for p70S6 kinase over Aurora B. The compounds of Examples 6, 10, 17 and 27 had a greater than 2 fold selectivity for p70S6 kinase over Aurora B.

Akt2 Kinase (PKBβ (h))

Buffer Composition:

20 mM MOPS, 1 mM EDTA, 0.01% Brij-35, 5% Glycerol, 0.1% b-mercaptoethanol, 1 mg/mL BSA In a final reaction volume of 25 μL, Akt2 (PKBβ (h)) (5-10 mU) is incubated with 8 mM MOPS pH 7.0, 0.2 mM EDTA, 30 μM GRPRTSSFAEGKK, 10 mM MgAcetate and [g-33P-ATP] (specific activity approx. 500 cpm/μmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

The results of the assays showed that the compounds of Examples 2, 9, 10, 11, 12, 13, 17, 18, 21, 25, 26, 27, 28, 32, 33, 34, 38, 41, 43, 44, 48, 50, 53 and 55 had a greater than 100 fold selectivity for p70S6 kinase over Akt2 kinase. The compounds of Examples 1, 3, 6, 7, 8, 24, 59 and 60 had a greater than 20 fold selectivity for p70S6 kinase over Akt2 kinase.

The results of the above assays demonstrate that many compounds of the invention have excellent selectivity for p70S6 kinase over Aurora A, Aurora B and Akt2 kinases.

Example 68

Investigating the Mechanism of Action of p70S6K Inhibitors in MCF-7 Cells by DS6 ELISA The following assay provides $IC_{50}$ values for inhibition of P70S6K activity in a whole cell assay by determining effects on the phosphorylation of $S6^{Ser235/236}$ in MCF-7 cells by ELISA.

Protocol:

The following protocol was used:

1) MCF-7 cells were seeded in 96-well plates at a density of 7×103 cells per well and allowed to adhere for 6 h in media containing 10% FBS.
2) The full serum media was replaced and cells incubated overnight in media containing 1% FBS, prior to addition of test compounds.
3) Test compounds were prepared from 10 mM or 5 mM (BEZ-235) DMSO stocks to give final concentration ranges as indicated on graphs. DMSO was constant at a final concentration of 1%.
4) Test compounds were incubated with cells in duplicate for 2 h at 37° C./5% CO2 in a humidified atmosphere.
5) The media was removed and cells were lysed by freeze-thawing in cell lysis buffer.
6) Detection of phosphorylated S6Ser235/236 was then carried out using a PathScan ELISA kit (Cell Signaling Technology #7205).
7) Lysates were diluted 1:1 with sample diluent before being applied to wells coated with an antibody against phosphorylated-S6 protein.
8) The ELISA was then performed as stated in the manufacturers' instructions.
9) The raw data were normalised to control values and analysed using a 4-parameter logistic equation in GraphPad Prism.

In the above assay, the compounds of Examples 9, 18, 27, 28, 33, 41, 50, 53, 55 and 58 were found to have $IC_{50}$ values of less than 1 μM. The compounds of Examples 1, 2, 3, 6, 7, 8, 11, 12, 17, 21, 25, 32, 51, 54 and 56 were all found to have $IC_{50}$ values of less than 5 μM. The compounds of Examples 43, 59 and 60 were found to have $IC_{50}$ values of less than 20 μM.

Example 69

MCF-7 Proliferation Assays

The following assay was used to determine the ability of test compounds to inhibit cell growth.

Protocol:

The following protocol was used:

1) MCF-7 cells were seeded in 96-well plates at 5000 cells per well and allowed to adhere overnight prior to addition of compound or vehicle control.
2) Test compounds were prepared from 10 mM DMSO stocks to give a final concentration range of 100 μM, 30 μM, 10 μM, 3 μM, 1 μM, 0.3 μM, 0.1 μM, 0.03 μM, 0.01 μM and vehicle control. The DMSO content was constant at 1%.
3) Test compounds were incubated with the cells for 72 h at 37° C. 5% CO2 in a humidified atmosphere.
4) Alamar blue 10% (v/v) was then added and incubated for a further 6 h, and fluorescent product detected using the BMG FLUOstar plate reader.
5) Data were analysed using a 4-parameter logistic equation in Graph Pad Prism.

Using the above assay, it was found that the compounds of Examples 1, 11, 12, 17, 18, 28, 38, 41 and 50 have $IC_{50}$ values of less than 10 μM. The compounds of Examples 2, 3, 6, 7, 8, 9, 13, 25, 31 and 33 were all found to have $IC_{50}$ values of less than 20 μM. The compounds of Examples 21, 26, 27 and 32 have $IC_{50}$ values of less than 50 μM.

Example 70

Pharmaceutical Formulations (i) Tablet Formulation

A tablet composition containing a compound of the formula (1) as defined in any one of Embodiments 1.1 to 1.31 may be prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) as defined in any one of Embodiments 1.1 to 1.31 with 100 mg lactose and filling the resulting mixture into standard opaque hard gelatin capsules.

(iii) Injectable Formulation I

A parenteral composition for administration by injection can be prepared by dissolving a compound of the formula (1) as defined in any one of Embodiments 1.1 to 1.31 in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) as defined in any one of Embodiments 1.1 to 1.31 (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (1) as defined in any one of Embodiments 1.1 to 1.31 (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of formula (1) as defined in any one of Embodiments 1.1 to 1.31 (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) as defined in any one of Embodiments 1.1 to 1.31 with pharmaceutical grade corn oil to give a concentration of 5 mg/ml. The composition is sterilised and filled into a suitable container.

viii) Lyophilised Formulation

Aliquots of formulated compound of formula (1) as defined in any one of Embodiments 1.1 to 1.31 are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

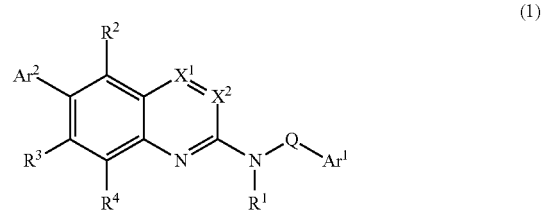

or a salt or tautomer thereof;
wherein:
$X^1$ is N or $N^+(O^-)$;
$X^2$ is N or CH;
Q is a $C_{1-3}$ alkylene group;
$R^1$ is selected from hydrogen, $C_{1-4}$ hydrocarbyl and hydroxy-$C_{2-4}$ hydrocarbyl;
$R^2$, $R^3$ and $R^4$ are the same or different and each is selected from hydrogen, fluorine, chlorine and methyl;
$Ar^1$ is a monocyclic 5 or 6-membered aryl or heteroaryl ring containing 0, 1 or 2 heteroatom ring members selected from O, N and S, or a naphthyl ring, the aryl or heteroaryl or naphthyl ring being optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; hydroxy; cyano; trifluoromethoxy; difluoromethoxy; amino; mono-$C_{1-4}$ hydrocarbylamino; di-$C_{1-4}$ hydrocarbylamino; $C_{1-4}$ hydrocarbyl-C(O)—; $C_{1-4}$ hydrocarbyl-C(O)-amino; $C_{1-4}$ hydrocarbylsulphonylamino; $C_{1-4}$ hydrocarbylureido; sulphamoyl; mono-$C_{1-4}$ hydrocarbylsulphamoyl; di-$C_{1-4}$ hydrocarbylsulphamoyl; carbamoyl; mono-$C_{1-4}$ hydrocarbyl carbamoyl; di-$C_{1-4}$ hydrocarbyl carbamoyl; a group O—$(CH_2)_k$—$OR^5$; and a group $O_m$—$(CH_2)_n$—$NR^6R^7$;
N2 to 4;
m is 0 or 1 and n is 0, 1, 2, 3 or 4 provided that when m is 1 then n is at least 2;
$R^5$ is hydrogen or $C_{1-4}$ hydrocarbyl;
$R^6$ is hydrogen or $C_{1-4}$ hydrocarbyl;
$R^7$ is hydrogen or $C_{1-4}$ hydrocarbyl;
or $NR^6R^7$ forms a saturated five or six membered heterocyclic ring optionally containing a further heteroatom selected from O, N and S or oxidised forms thereof, the heterocyclic ring being optionally substituted with 1 to 4 $C_{1-4}$ hydrocarbyl groups or hydroxy;
$Ar^2$ is a monocyclic 5 or 6-membered heteroaryl ring containing 1, 2 or 3 heteroatom ring members selected from O, N and S and being optionally substituted with 1, 2 or 3 substituents selected from fluorine; chlorine; bromine; $C_{1-4}$ hydrocarbyl; $C_{1-4}$ alkoxy; trifluoromethyl; difluoromethyl; hydroxy; cyano; trifluoromethoxy; difluoromethoxy; amino; mono-$C_{1-4}$ hydrocarbylamino; di-$C_{1-4}$ hydrocarbylamino; $C_{1-4}$ hydrocarbyl-C(O)—; $C_{1-4}$ hydrocarbyl-C(O)-amino; $C_{1-4}$ hydrocarbylsulphonylamino; $C_{1-4}$ hydrocarbylureido; sulphamoyl; mono-$C_{1-4}$ hydrocarbylsulphamoyl; di-$C_{1-4}$ hydrocarbylsulphamoyl; carbamoyl; mono-$C_{1-4}$ hydrocarbyl carbamoyl; and di-$C_{1-4}$ hydrocarbyl carbamoyl;

and wherein, in each substituent consisting of or containing C$_{1-4}$ hydrocarbyl, the C$_{1-4}$ hydrocarbyl is selected from C$_{1-4}$ alkyl, C$_{2-4}$ alkenyl, C$_{2-4}$ alkynyl, cyclopropyl and cyclopropylmethyl.

2. A compound according to claim 1 wherein:
X$^1$ is N or N$^+$(O$^-$);
X$^2$ is N or CH;
Q is a C$_{1-3}$ alkylene group;
R$^1$ is selected from hydrogen, C$_{1-4}$ alkyl and hydroxy-C$_{2-4}$ alkyl;
R$^2$, R$^3$ and R$^4$ are the same or different and each is selected from hydrogen, fluorine, chlorine and methyl;
Ar$^1$ is a monocyclic 5 or 6-membered aryl or heteroaryl ring containing 0, 1 or 2 heteroatom ring members selected from O, N and S and being optionally substituted with 1, 2 or 3 substituents selected from fluorine; chlorine; bromine; C$_{1-4}$ alkyl; C$_{1-4}$ alkoxy; trifluoromethyl; difluoromethyl; hydroxy; cyano; trifluoromethoxy; difluoromethoxy; amino; mono-C$_{1-4}$ alkylamino; di-C$_{1-4}$ alkylamino C$_{1-4}$ alkanoyl; C$_{1-4}$ alkanoylamino; C$_{1-4}$ alkylsulphonylamino; C$_{1-4}$ alkylureido; sulphamoyl; mono-C$_{1-4}$ alkylsulphamoyl; di-C$_{1-4}$ alkylsulphamoyl; carbamoyl; mono-C$_{1-4}$ alkyl carbamoyl; and di-C$_{1-4}$ alkyl carbamoyl; and
Ar$^2$ is a monocyclic 5 or 6-membered heteroaryl ring containing 1, 2 or 3 heteroatom ring members selected from O, N and S and being optionally substituted with 1, 2 or 3 substituents selected from fluorine; chlorine; bromine; C$_{1-4}$ alkyl; C$_{1-4}$ alkoxy; trifluoromethyl; difluoromethyl; hydroxy; cyano; trifluoromethoxy; difluoromethoxy; amino; mono-C$_{1-4}$ alkylamino; di-C$_{1-4}$ alkylamino; C$_{1-4}$ alkanoyl; C$_{1-4}$ alkanoylamino; C$_{1-4}$ alkylsulphonylamino; C$_{1-4}$ alkylureido; sulphamoyl; mono-C$_{1-4}$ alkylsulphamoyl; di-C$_{1-4}$ alkylsulphamoyl; carbamoyl; mono-C$_{1-4}$ alkyl carbamoyl; and di-C$_{1-4}$ alkyl carbamoyl.

3. A compound according to claim 1 wherein Q is C$_{1-2}$ alkylene.

4. A compound according to claim 3 wherein Q is CH$_2$ or CH(CH$_3$).

5. A compound according to claim 1—wherein X$^1$ is N.

6. A compound according to claim 1 wherein X$^1$ is N$^+$(O$^-$).

7. A compound according to claim 1 wherein X$^2$ is N.

8. A compound according to claim 1 wherein X$^2$ is CH.

9. A compound according to claim 1 wherein R$^1$ is hydrogen.

10. A compound according to claim 1 wherein Ar$^1$ is a monocyclic aryl or heteroaryl ring selected from phenyl, thienyl, pyridyl and naphthyl, each optionally substituted as defined in claim 1.

11. A compound according to claim 10 wherein Ar$^1$ is a phenyl ring optionally substituted as defined in claim 1.

12. A compound according to claim 1 wherein Ar$^1$ is unsubstituted or is substituted with 1, 2 or 3 substituents selected from fluorine, chlorine, methyl, hydroxy, methoxy, trifluoromethyl, difluoromethyl, trifluoromethoxy, morpholinyl, piperazinyl, N-methylpiperazinyl and dimethylaminoethoxy.

13. A compound according to claim 12 wherein Ar$^1$ is unsubstituted or is substituted with 1, 2 or 3 substituents selected from fluorine, chlorine, methyl, methoxy, trifluoromethyl and trifluoromethoxy.

14. A compound according to claim 13 wherein Ar$^1$ is unsubstituted or is substituted with one or two substituents.

15. A compound according to claim 1 wherein R$^2$ is hydrogen.

16. A compound according to claim 1 wherein R$^3$ is hydrogen.

17. A compound according to claim 1 wherein R$^4$ is hydrogen.

18. A compound according to claim 1 wherein Ar$^2$ is selected from pyrazole, imidazole, oxazole, isoxazole, thiazole, isothiazole, furan, thiophene, pyridine, pyrimidine, pyrazine, pryidazine, triazole, thiadiazole, furazan and oxadiazole rings each optionally substituted as defined in claim 1.

19. A compound according to claim 18 wherein Ar$^2$ is an optionally substituted pyrazole ring.

20. A compound according to claim 1 wherein Ar$^2$ is unsubstituted.

21. A compound according to claim 1 which is selected from:
Benzyl-[6-(1H-pyrazol-4-yl)-quinoxalin-2-yl]-amine;
Benzyl-methyl-[6-(1H-pyrazol-4-yl)-quinoxalin-2-yl]-amine;
2-{Benzyl-[6-(1H-pyrazol-4-yl)-quinoxalin-2-yl]-amino}-ethanol;
(4-Morpholin-4-yl-benzyl)-[6-(1H-pyrazol-4-yl-quinoxalin-2-yl]-amine;
[4-(4-Methyl-piperazin-1-yl)-benzyl]-[6-(1H-pyrazol-4-yl)-quinoxalin-2-yl]-amine;
[3-(4-Methyl-piperazin-1-yl)-benzyl]-[6-(1H-pyrazol-4-yl)-quinoxalin-2-yl]-amine;
(3-Morpholin-4-yl-benzyl)-[6-(1H-pyrazol-4-yl)-quinoxalin-2-yl]-amine;
(4-Chloro-benzyl)-[6-(1H-pyrazol-4-yl)-quinoxalin-2-yl]-amine;
(3-Chloro-benzyl)-[6-(1H-pyrazol-4-yl)-quinoxalin-2-yl]-amine;
(2-Chloro-benzyl)-[6-(1H-pyrazol-4-yl-quinoxalin-2-yl]-amine;
(4-Fluoro-benzyl)-[6-(1H-pyrazol-4-yl)-quinoxalin-2-yl]-amine;
(3-Fluoro-benzyl)-[6-(1H-pyrazol-4-yl)-quinoxalin-2-yl]-amine;
(2-Fluoro-benzyl)-[6-(1H-pyrazol-4-yl)-quinoxalin-2-yl]-amine;
[6-(1H-Pyrazol-4-yl)-quinoxalin-2-yl]-pyridin-4-ylmethyl-amine;
[6-(1H-Pyrazol-4-yl)-quinoxalin-2-yl]-pyridin-3-ylmethyl-amine;
[6-(1H-Pyrazol-4-yl)-quinoxalin-2-yl]-pyridin-2-ylmethyl-amine;
(4-Methoxy-benzyl)-[6-(1H-pyrazol-4-yl)-quinoxalin-2-yl]-amine;
(3-Methoxy-benzyl)-[6-(1H-pyrazol-4-yl)-quinoxalin-2-yl]-amine;
(2-Methoxy-benzyl)-[6-(1H-pyrazol-4-yl)-quinoxalin-2-yl]-amine;
(4-Fluoro-3-trifluoromethyl-benzyl)-[6-(1H-pyrazol-4-yl)-quinoxalin-2-yl]-amine;
(4-Fluoro-benzyl)-methyl-[6-(1H-pyrazol-4-yl)-quinoxalin-2-yl]-amine;
Benzyl-methyl-(6-pyridin-4-yl-quinoxalin-2-yl)-amine;
Benzyl-methyl-(6-pyrimidin-4-yl-quinoxalin-2-yl)-amine;
((S)-1-Phenyl-ethyl)-[6-(1H-pyrazol-4-yl)-quinoxalin-2-yl]-amine;
Phenethyl-[6-(1H-pyrazol-4-yl)-quinoxalin-2-yl]-amine;
Benzyl-ethyl-[6-(1H-pyrazol-4-yl)-quinoxalin-2-yl]-amine;
(3-Methoxy-benzyl)-methyl-[6(1H-pyrazol-4-yl)-quinoxalin-2-yl]-amine;

(3-Fluoro-benzyl)-methyl-[6-(1H-pyrazol-4-yl)-quinoxalin-2-yl]-amine;
(4-Fluoro-3-trifluoromethyl-benzyl)-methyl-[6-(1H-pyrazol-4-yl)-quinoxalin-2-yl]-amine;
[6-(1H-Pyrazol-4-yl)-quinoxalin-2-yl]-(3-trifluoromethoxy-benzyl)-amine;
[3-(2-Dimethylamino-ethoxy)-benzyl]-[6-(1H-pyrazol-4-yl)-quinoxalin-2-yl]-amine;
(3,4-Difluoro-benzyl)-[6-(1H-pyrazol-4-yl)-quinoxalin-2-yl]-amine;
((R)-1-Phenyl-ethyl)-[6-(1H-pyrazol-4-yl)-quinoxalin-2-yl]-amine;
Benzyl-methyl-[7-(1H-pyrazol-4-yl)-benzo[1,2,4]triazin-3-yl]-amine;
Benzyl-methyl-[1-oxy-7-(1H-pyrazol-4-yl)-benzo[1,2,4]triazin-3-yl]-amine;
(3-Methoxy-benzyl)-[1-oxy-7-(1H-pyrazol-4-yl)-benzo[1,2,4]triazin-3-yl]-amine;
(3-Methoxy-benzyl)-[7-(1H-pyrazol-4-yl)-benzo [1,2,4]triazin-3-yl]amine;
[6-(1H-Pyrazol-4-yl)-quinoxalin-2-yl]-thiophen-3-ylmethyl-amine;
Naphthalen-2-ylmethyl-[6-(1H-pyrazol-4-yl)-quinoxalin-2-yl]-amine;
[6-(1H-Pyrazol-4-yl)-quinoxalin-2-yl]-(4-trifluoromethyl-benzyl)-amine;
(3-Methyl-benzyl)-[6-(1H-pyrazol-4-yl)-quinoxalin-2-yl]-amine;
(2-Methyl-benzyl)-[6-(1H-pyrazol-4-yl)-quinoxalin-2-yl]-amine;
Benzyl-methyl-(6-pyrimidin-5-yl-quinoxalin-2-yl)-amine;
(4-Methyl-benzyl)-[6-(1H-pyrazol-4-yl)-quinoxalin-2-yl]-amine;
(2-Chloro-benzyl)-methyl-[6-(1H-pyrazol-4-yl)-quinoxalin-2-yl]-amine;
Benzyl-[6-(5-methyl-1H-pyrazol-4-yl)-quinoxalin-2-yl]-amine;
{(R)-1-[3-(4-Methyl-piperazin-1-yl)-phenyl]-ethyl}-[6-(1H-pyrazol-4-yl)-quinoxalin-2-yl]-amine;
Methyl-[3-(4-methyl-piperazin-1-yl)-benzyl]-[6-(1H-pyrazol-4-yl)-quinoxalin-2-yl]-amine;
[(R)-1-(3-Fluoro-phenyl)-ethyl]-[6-(1H-pyrazol-4-yl)-quinoxalin-2-yl]-amine;
[(R)-1-(3-Methoxy-phenyl)-ethyl]-[6-(1H-pyrazol-4-yl)-quinoxalin-2-yl]-amine;
(3-Piperazin-1-yl-benzyl)-[6-(1H-pyrazol-4-yl)-quinoxalin-2-yl]-amine;
Methyl-((R)-1-phenyl-ethyl)-[6-(1H-pyrazol-4-yl)-quinoxalin-2-yl]-amine;
[(R)-1-(3-Fluoro-phenyl)-ethyl]-methyl-[6-(1H-pyrazol-4-yl)-quinoxalin-2-yl]-amine;
[(R)-1-(3-Methoxy-phenyl)-ethyl]-methyl-[6-(1 H-pyrazol-4-yl)-quinoxalin-2-yl]-amine;
3-{[6-(1H-Pyrazol-4-yl)-quinoxalin-2-ylamino]-methyl}-phenol;
[(R)-1-(3-Chloro-phenyl)-ethyl]-[6-(1H-pyrazol-4-yl)-quinoxalin-2-yl]-amine;
[(R)-1-(3-Chloro-phenyl)-ethyl]-methyl-[6-(1H-pyrazol-4-yl)-quinoxalin-2-yl]-amine;
Methyl-((S)-1-phenyl-ethyl)-[6-(1H-pyrazol-4-yl)-quinoxalin-2-yl]-amine;
[6-(1H-Pyrazol-4-yl)-quinoxalin-2-yl]-((R)-1-m-tolyl-ethyl)-amine;
[(S)-1-(3-Fluoro-phenyl)-ethyl]-[6-(1H-pyrazol-4-yl)-quinoxalin-2-yl]amine; and
[(S)-1-(3-Fluoro-phenyl)-ethyl]-methyl-[6-(1 H-pyrazol-4-yl)-quinoxalin-2-yl]-amine;
and salts and tautomers thereof.

22. A pharmaceutical composition .comprising a compound as defined in claim 1 together with a pharmaceutically acceptable excipient.

* * * * *